United States Patent
Hjorth et al.

(10) Patent No.: US 12,110,562 B2
(45) Date of Patent: Oct. 8, 2024

(54) COMPOSITIONS AND METHODS FOR PREDICTING AND PROMOTING WEIGHT LOSS

(71) Applicant: University of Copenhagen, Copenhagen (DK)

(72) Inventors: Mads Fiil Hjorth, Rødovre (DK); Arne Vernon Astrup, Klampenborg (DK); Yishai Zohar, Brookline, MA (US)

(73) Assignee: University of Copenhagen, Copenhagen (DK)

( * ) Notice: Subject to any disclaimer, the term of this patent is extended or adjusted under 35 U.S.C. 154(b) by 395 days.

(21) Appl. No.: 15/992,496

(22) Filed: May 30, 2018

(65) Prior Publication Data

US 2019/0062811 A1 Feb. 28, 2019

Related U.S. Application Data

(60) Provisional application No. 62/646,884, filed on Mar. 22, 2018, provisional application No. 62/594,172, (Continued)

(51) Int. Cl.
*C12Q 1/689* (2018.01)
*A23L 33/00* (2016.01)
(Continued)

(52) U.S. Cl.
CPC .............. *C12Q 1/689* (2013.01); *A23L 33/21* (2016.08); *A23L 33/30* (2016.08); *A23L 33/40* (2016.08);
(Continued)

(58) Field of Classification Search
CPC ...... C12Q 1/689; A61K 35/74; A61K 35/741; A61K 2300/00; A23L 33/21;
(Continued)

(56) References Cited

U.S. PATENT DOCUMENTS

| | | |
|---|---|---|
| 2003/0007996 A1 | 1/2003 | Graham et al. |
| 2008/0193603 A1 | 8/2008 | Hayes et al. |

(Continued)

FOREIGN PATENT DOCUMENTS

| | | |
|---|---|---|
| WO | 0211562 A2 | 2/2002 |
| WO | 2016/020119 A1 | 2/2016 |
| WO | 2016/078944 A1 | 5/2016 |

OTHER PUBLICATIONS

Roager et al., (Appl Environ Microbiol. Feb. 2014; 80(3): 1142-1149). (Year: 2014).*

(Continued)

*Primary Examiner* — Jana A Hines
(74) *Attorney, Agent, or Firm* — Elmore Patent Law Group, P.C.; Carolyn S. Elmore; Edgar W. Harlan

(57) ABSTRACT

The invention provides methods for identifying biomarkers in a patient's microbiota to predict a patient's response to a predetermined diet to promote weight loss and methods of promoting weight loss in the patient by optimizing the patient's diet in accordance with the biomarkers identified in the patient's gut microbiota. The methods of the invention can also be used to manage or maintain weight, i.e., prevent or inhibit weight gain, in a patient who is of normal weight or is overweight or obese.

3 Claims, 15 Drawing Sheets

Related U.S. Application Data filed on Dec. 4, 2017, provisional application No. 62/550,925, filed on Aug. 28, 2017, provisional application No. 62/513,743, filed on Jun. 1, 2017.

(51) Int. Cl.

| | |
|---|---|
| *A23L 33/21* | (2016.01) |
| *A61K 35/74* | (2015.01) |
| *A61K 35/741* | (2015.01) |
| *A61P 3/04* | (2006.01) |
| *A61P 3/06* | (2006.01) |

(52) U.S. Cl.
CPC ............ *A61K 35/74* (2013.01); *A61K 35/741* (2013.01); *A61P 3/04* (2018.01); *A61P 3/06* (2018.01); *A23V 2002/00* (2013.01); *A23V 2200/332* (2013.01)

(58) Field of Classification Search
CPC ........ A23L 33/135; A23L 33/40; A23L 33/30; A61P 3/04; A61P 3/06; A23V 2200/332; A23V 2002/00
See application file for complete search history.

(56) References Cited

U.S. PATENT DOCUMENTS

| | | |
|---|---|---|
| 2008/0275728 A1 | 11/2008 | Ordovas et al. |
| 2012/0058094 A1 | 3/2012 | Blaser et al. |
| 2013/0079612 A1 | 3/2013 | Hunt et al. |
| 2014/0052722 A1 | 2/2014 | Bertsimas et al. |
| 2014/0128289 A1 | 5/2014 | Gordon et al. |
| 2015/0284779 A1 | 10/2015 | Le Chatelier et al. |
| 2015/0366898 A1 | 12/2015 | Ron et al. |
| 2019/0062811 A1 | 2/2019 | Hjorth et al. |

OTHER PUBLICATIONS

Poulsen et al., (The American Journal of Clinical Nutrition, vol. 99, Issue 1, Jan. 2014, pp. 35-45. Published Nov. 20, 2013). (Year: 2013).*
Panagiotakos, et al. "The Relationship between Dietary Habits, Blood Glucose and Insulin Levels among People without Cardiovascular Disease and Type 2 Diabetes," Rev. Diabetic Stud., 2: 208-215 (2005).
Egshatyan, L., et al., "Gut microbiota and diet in patients with different glucose tolerance," Endocrine Connections, 5: 1-9 (2016).
Roager, H. M., et al., "Microbial Enterotypes, Inferred by the Prevotella-to-Bacteroides Ratio, Remained Stable during a 6-Month Randomized Controlled Diet Intervention with the New Nordic Diet," Applied and Environmental Microbiology, 80(3): 1142-1149 (2014).
Roager, H. M., et al., Supplemental Material for "Microbial Enterotypes, Inferred by the Prevotella to Bacteroides Ratio, Remain Stable during a 6-Month Randomized Controlled Diet Intervention with the New Nordic Diet," pp. 1-13 (2014).
Kovatcheva-Datchary, P., et al., "Dietary Fiber-Induced Improvement in Glucose Metabolism Is Associated with Increased Abundance of Prevotella," Cell Metabolism 22: 971-982 (2015).
Menni, C., et al., "Gut microbiome diversity and high-fibre intake are related to lower long-term weight gain," International Journal of Obesity, pp. 1-7 (2017).
Kang, C. et al., "Healthy Subjects Differentially Respond to Dietary Capsaicin Correlating with Specific Gut Enterotypes," J Clin Endocrinol Metab, 101(12): 4681-4689 (2016).
F. de Moraes, A. C., et al., "Enterotype May Drive the Dietary-Associated Cardiometabolic Risk Factors," Frontiers in Cellular and Infection Microbiology, 7(47): 1-9 (2017).
Kjølboek, L., et al., "Protein supplements after weight loss do not improve weight maintenance compared with recommended dietary protein intake despite beneficial effects on appetite sensation and energy expenditure: a randomized, controlled, double-blinded trial," Am J Clin Nutr., pp. 1-14 (2017).
Arumugam, M., et al., "Enterotypes of the human gut microbiome," Nature, 473: 174-180 (2011).
Gorvitovskaia, A., et al., "Interpreting Prevotella and Bacteroides as biomarkers of diet and lifestyle," Microbiome, 4(15): 1-12 (2016).
Hong, P.-Y., et al., "Relative Abundance of *Bacteroides* spp. in Stools and Wastewaters as Determined by Hierarchical Oligonucleotide Primer Extension," Applied and Environmental Microbiology, 74(9): 2882-2893 (2008).
Due, A., et al., "Comparison of 3 ad libitum diets for weight-loss maintenance, risk of cardiovascular disease, and diabetes: a 6-mo randomized, controlled trial," Am J Clin Nutr., 88: 1232-1241 (2008).
Wikipedia, Hyperglycemia, May 27, 2016; p. 1/5, para 1; Retrieved on Aug. 2, 2017, from https://en.wikipedia.org/wiki/Hyperglycemia.
Wikipedia, Nordic race, May 23, 2016; p. 1/18, para 1; Retrieved on Aug. 2, 2017, from <https:1/en. wikipedia .org/wiki/Nordic_race>.
Anonymous, , "Understanding Pre-Diabetes", Retrieved from the Internet: Diseases & Conditions Diabetes -Prevention Retrieved from: URL:https://web.archive.org/web/2014110923 2149/http://my.clevelandclinic.org/health/diseases conditions/hie Diabetes Basics/hic Understanding Pre-Diabetes, [retrieved on Aug. 10, 2017], Jan. 1, 2013.
Fujioka, K. et al., "Weight loss with sibutramine improves glycaemic control and other metabolic parameters in obese patients with type 2 diabetes mellitus", Diabetes, Obesity and Metabolism, vol. 2, No. 3, 2000, 175-187.
Greenberg, R., "Glycemic Load and Glycemic Index: What's the Difference and Why Does it Matter?", HuffPost, Aug. 29, 2011; p. 3/6, highlight; Retrieved on Aug. 2, 2017, from <http://www.huffingtonpost.com/riva-greenberg/g1-and-gi_b_863126.html>.
Racette, S. B. et al., "Modest weight loss improves insulin action in obese African Americans", Metabolism Clinical and Experimental, vol. 54, No. 7, 2005, 960-965.
Wu, G. D. et al., "Linking long-term dietary patterns with gut microbial enterotypes", Science, vol. 334, No. 605, Oct. 7, 2011, 105-108.
Mithril, C., et al., "Dietary Composition and Nutrient Content of the New Nordic Diet," Public Health Nutrition, 16(5): pp. 777-785 (2012).

\* cited by examiner

COMPOSITIONS AND METHODS FOR PREDICTING AND PROMOTING WEIGHT LOSS

RELATED APPLICATIONS

This application claims the benefit of U.S. Provisional Application No. 62/513,743, filed on Jun. 1, 2017, U.S. Provisional Application No. 62/550,925, filed on Aug. 28, 2017, U.S. Provisional Application No. 62/594,172, filed on Dec. 4, 2017 and U.S. Provisional Application No. 62/646,884, filed on Mar. 22, 2018. The entire teachings of the above applications are incorporated herein by reference.

BACKGROUND OF THE INVENTION

Public health efforts and current anti-obesity agents have not controlled the obesity epidemic. This disorder is increasingly prevalent in industrialized nations because of the abundance of food and the reduced activity levels that accompany the movement of populations from rural to urban settings. Obesity is loosely defined as an excess of body fat over that needed to maintain health.

Obesity is a condition in which excess body fat has accumulated to such an extent that health may be negatively affected. (World Health Organization (2000)). (Technical report series 894: Obesity: Preventing and managing the global epidemic). It is commonly defined as a Body Mass Index (BMI=weight divided by height squared) of 30 kg/m$^2$ or higher. Overweight is distinguished and defined as a BMI between 25-29.9 kg/m$^2$ (*Obes. Res.* 1998 September; 6 Suppl. 2:51S-209S). (Clinical Guidelines on the Identification, Evaluation, and Treatment of Overweight and Obesity in Adults—The Evidence Report. National Institutes of Health).

Excessive body weight is associated with various diseases, particularly cardiovascular diseases, diabetes mellitus type 2, obstructive sleep apnea, certain types of cancer, and osteoarthritis (National Heart, Lung, and Blood Institute. Clinical Guidelines on the Identification, Evaluation, and Treatment of Overweight and Obesity in Adults NIH Publication No. 98-4083 September 1998 National Institutes of Health). As a result, obesity has been found to reduce life expectancy. The primary treatment for obesity is dieting and physical exercise. If diet and exercise fail, anti-obesity drugs and bariatric surgery may be recommended in severe cases (National Institute for Health and Clinical Excellence. Clinical Guideline 43: Obesity: The prevention, identification, assessment and management of overweight and obesity in adults and children. London, 2006).

The pathogenesis of obesity is multi-factorial and includes the control of feeding behavior, mechanisms of fat storage, the components of energy intake and expenditure, and genetic and psychological influences. Likewise, the treatment of obesity is generally multi-factorial. Unfortunately, the mechanisms of fat storage and genetic influences that leads to excessive fat storage and obesity are not easy to treat. The control of feeding behavior and psychological influences require prolonged treatment. Although the components of energy intake and expenditure are treatable, many obese individuals are resistant to or incapable of engaging in activities that significantly increase their energy expenditure. There is a need for new methods for managing weight and preventing or treating overweight and obesity.

One possibility for promoting weight loss in a patient is to tailor the weight loss program to the individual in need of weight loss. Recently, the existence of a limited number of well-balanced, defined host-microbial symbiotic states in the gut has been demonstrated (M. Arumugam, et al., (2011) *Nature* 473:174-80). These states have been referred to as "enterotypes". These enterotypes have been shown to be very robust and were detected in data spanning many nations and several continents. Thus, people can be characterized by their gut microbiota and can be assigned either enterotype 1 (E1), enterotype 2 (E2), or enterotype 3 (E3). It is known that gut microbiota are quite stable in individuals and can even be restored after perturbations such as antibiotic use (Zoetendal et al. (2008) *Gut* 57:1605-15). This implies that enterotypes are stable over time. Diseases known to be associated with aberrations in microbiota include but are not limited to, obesity and related comorbidities including metabolic syndrome and various types of diabetes such as type I diabetes and type II diabetes, Autistic Spectrum Disorder (ASD) related diseases, celiac disease and some forms of cancer (Zoetendal et al., 2008, supra). The present invention leverages an individual's specific enterotype to identify a personalized diet and nutrition program for that individual to promote weight loss and treat obesity.

SUMMARY OF THE INVENTION

The invention provides methods for identifying biomarkers in a patient's microbiota to predict a patient's response to a predetermined diet to promote weight loss and methods of promoting weight loss in the patient by optimizing the patient's diet in accordance with the biomarkers identified in the patient's gut microbiota. The methods of the invention can also be used to manage or maintain weight, i.e., prevent or inhibit weight gain, in a patient who is of normal weight or is overweight or obese.

Provided are methods for predicting dietary weight loss in a patient comprising the steps of identifying a patient has at least one of certain preferred gut microbiota characteristics selected from: i) patients with the *Prevotella* spp. enterotype (E2); (ii) patients with a relative abundance of log 10(*Prevotella* spp.) of greater than −3 in their microbiota; (iii) patients with a relative abundance of log 10(*Prevotella* spp./*Bacteriodes* spp.) of greater than −2 in their microbiota and preferably greater than about −0.5 in their microbiota, and preferably greater than about −0.48 in their microbiota and preferably from about −0.48 to −0.15 in their microbiota; (iv) patients with a relative abundance of Log 10(*Prevotella* spp/*Bacteroidetes* all) of greater than −2 in their microbiota; or (v) or patients with a relative abundance of Log 10(*Bacteroidetes* all/*Bacteroides* spp.) of greater than 0 in their microbiota (collectively referred to herein as "preferred gut microbiota characteristic(s)" or PGMC") and predicting dietary weight loss success of the patient on a predetermined diet such as a diet that is high in fiber and whole grain, based on whether the patient has at least one PGMC.

Also provided are methods of promoting weight loss in a patient having at least one PGMC comprising administering to the patient a diet that is high in fiber and whole grain.

Also provided are methods of predicting dietary weight loss in a patient comprising the steps of identifying a patient having at least one PGMC in combination with determining if a patient has one or more of (i) elevated fasting blood glucose levels and (ii) low fasting blood insulin levels and predicting dietary weight loss success of the patient on a predetermined diet such as a diet that is high in fiber and whole grain, based on whether the patient has certain preferred microbiota characteristics in combination with one or more of (i) elevated fasting blood glucose levels and (ii) low fasting blood insulin levels.

Also provided are methods of promoting weight loss in a patient on a high fiber/high whole grain diet comprising the step of altering the gut microbiota population such that the patient has at least one PGMC, for example by increasing the relative abundance of *Prevotella* spp. and/or by reducing the relative abundance of *Bacteriodes* spp.

Also provided are methods for predicting weight loss and promoting weight loss using predetermined diets in patients having the *Prevotella* spp. enterotype optionally including individuals of the *Bacteriodes* spp. enterotype wherein their relative abundance of *Prevotella* spp. is less than about 0.000001 and is preferably less than about 0.0000005.

Also provided are methods for predicting weight loss and promoting weight loss using predetermined diets in patients having low relative abundance of *Prevotella* spp. Preferably excluding individuals having very low relative abundance of *Prevotella* spp. such as having a relative abundance of *Prevotella* spp. that is less than about 0.000001 and preferably having a relative abundance of *Prevotella* spp. is less than about 0.0000005. The invention also provides methods for predicting a patient's ability to maintain weight loss on a predetermined diet based on determining whether the patient has low relative abundance of *Prevotella* or high relative abundance of *Prevotella* in combination with determining whether the patient has low fasting insulin (FI) or high FI.

DETAILED DESCRIPTION OF THE INVENTION

Figure 1A:
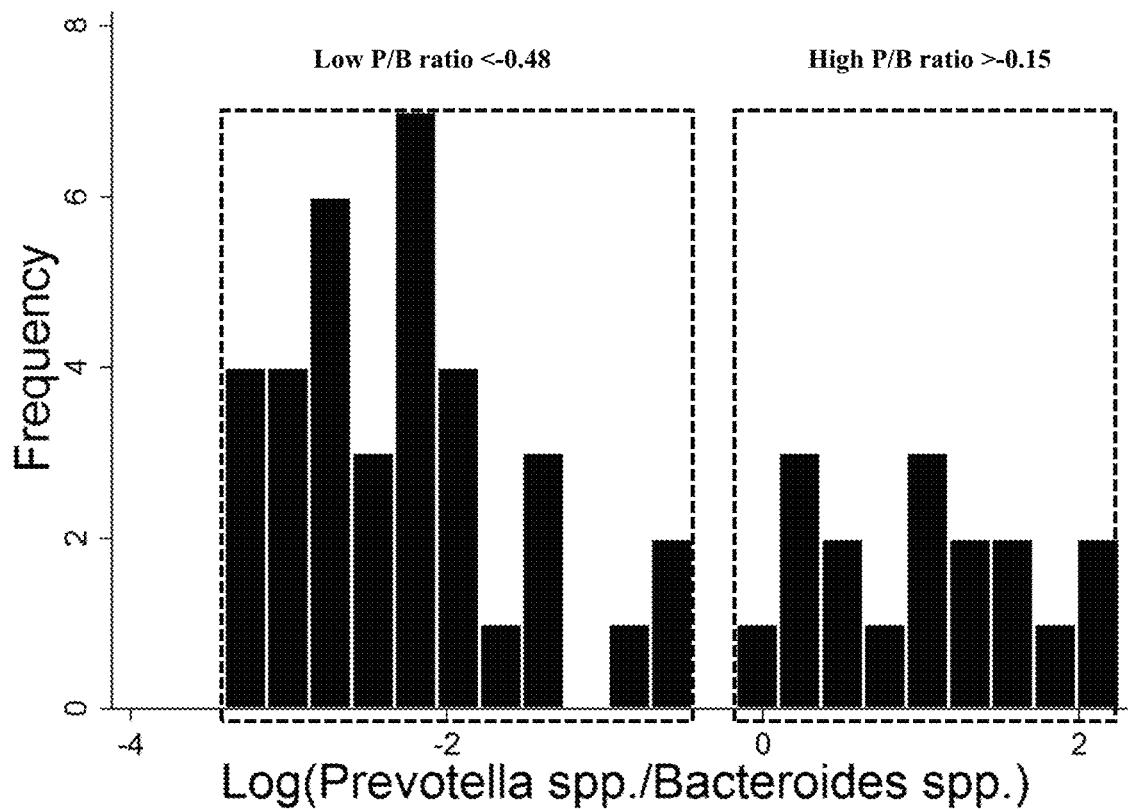
FIG. 1A is a bar graph showing two distinct groups of participants that were observed prior to intervention based on the log-transformed relative abundance of *Bacteroides* spp. and the log-transformed relative abundance of *Prevotella* spp.—referred to as low (n=27) and high (n=17) *Prevotella*-to-*Bacteriodes* (P/B) groups. Participants with no detectable *Prevotella* spp., referred to as the 0-*Prevotella* group, constitute the third group (n=8) but was excluded from this figure.

The term "enterotype" is well known from the publication by Arumugam et al. (2011), supra. It refers to a characteristic gastrointestinal microbial community of which only a limited number exist across individuals. The enterotype is characteristic for an individual, in line with gut microbiota being quite stable in individuals and capable of being restored even after perturbation. Presently, three of such enterotypes have been identified. Enterotype 1 (E1) is enriched in *Bacteroides* spp. Enterotype 2 (E2) is enriched in *Prevotella* spp. Enterotype 3 (E3) is enriched in *Ruminococcus* spp.

As used herein a "subject" may be an animal or a human.

"Relative abundance" as used herein is the proportion of a bacteria of a particular kind relative to the total number of bacteria in the area. The sum of the relative abundance of all bacteria in the area will be 1.

As used herein a "patient" is preferably a human patient. The patient may be of normal weight but at risk for unhealthy risk increase. The patient may be overweight or the patient may be obese.

As used herein a patient of "normal weight" has a body mass index of about 18.5 $kg/mg^2$ to 24.9 $kg/m^2$. As used herein an "overweight" is a human having a body mass index above about 25 $kg/m^2$ to about 29.9 $kg/m^2$. An "obese" patient has a body mass index of 30 or higher. The body mass index is defined as the individual's body mass divided by the square of his or her height. The formulae universally used in medicine produce a unit of measure of $kg/m^2$.

The term "sample" is preferably a biological sample. As used herein, a "biological sample" refers to a biological tissue or biological fluid from a patient. A variety of samples can be useful in practicing the invention including, for example, feces (a "fecal sample"), an intestinal sample, blood, serum, plasma, urine, breath (exhaled air), DNA, salivary fluid, ascite fluid, and the like. For example, microbial metabolites may be found in the urine, blood, fecal water or extracts of fecal material or exhaled air. It is known that specific host-microbe interactions occur in the human body and hence it is feasible that host genomic sequences may be correlated with specific enterotypes. The term "intestinal sample" refers to all samples that originate from the intestinal tract, including, without limitation, feces samples, rectal swap samples, but also samples obtained from other sites in the intestinal tract, such as mucosal biopsies, cecal samples, and ileum samples. The test sample may have been processed; for example, DNA and/or RNA and/or protein may have been isolated from feces samples, rectal swap samples, or samples obtained from other sites in the intestinal tract.

By "microbiota", it is herein referred to microflora and microfauna in an ecosystem such as intestines, mouth, vagina, or lungs. In microbiology, flora (plural: floras or florae) refers to the collective bacteria and other microorganisms in an ecosystem (e.g., some part of the body of an animal host).

The "gut microbiota" as used herein refers to the microorganisms that inhabit the digestive tract (also referred to as "gut" or "gastrointestinal tract (GI)").

The term "cecal microbiota" refers to microbiota derived from cecum, which in mammals is the beginning region of the large intestine in the form of a pouch connecting the ileum with the ascending colon of the large intestine; it is separated from the ileum by the ileocecal valve (ICV), and joins the colon at the cecocolic junction.

The term "ileal microbiota" refers to microbiota derived from ileum, which in mammals is the final section of the small intestine and follows the duodenum and jejunum; ileum is separated from the cecum by the ileocecal valve (ICV).

As used herein, the term "probiotic" refers to a single substantially pure bacterium (i.e., a single isolate), or a mixture of desired bacteria, and may also include any additional components that can be administered to a mammal for restoring microbiota. Such compositions are also referred to herein as a "bacterial inoculant." Probiotics or bacterial inoculant compositions of the invention are preferably administered with a buffering agent to allow the bacteria to survive in the acidic environment of the stomach, i.e., to resist low pH and to grow in the intestinal environment. Such buffering agents include sodium bicarbonate, juice, milk, yogurt, infant formula, and other dairy products.

The terms "treat" or "treatment" of a state, disorder or condition include: (1) preventing or delaying the appearance of at least one clinical or sub-clinical symptom of the state, disorder or condition developing in a patient that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a patient to be treated is either statistically significant or at least perceptible to the patient or to the physician.

As used herein the "New Nordic Diet" (NND) is a high fiber diet developed in 2004 by food professionals to define a new regional cuisine which is primarily plant-based and is high in vegetables, fruits and whole grains. The New Nordic Diet comprises about 35% less meat than the Average Danish Diet. Compared with Average Danish Diet, the NND is higher in absolute intake of fruits, berries, vegetables, root vegetables, potatoes, legumes, vegetable fats and oils (primarily rapeseed oil), fish and eggs, but lower in meat products and poultry, dairy products, sweets and desserts and alcoholic beverages as compared to the ADD.

The Average Danish Diet includes the Danish Dietary guidelines that are endorsed by the Ministry of Food, Agriculture and Fisheries prior to 2011.

The "Mediterranean Diet (MD)" is another popular diet that is higher in fiber but does not include as much fiber as the NND. The MD features olive oil instead of the rapeseed/canola oil primarily used in the New Nordic Diet. The MD is also higher in fat as compared to the NND.

As used herein the term "preferred gut microbiota characteristics" or "PGMC" refers to the characteristics of a patient's microbiota that enhance the patient's susceptibility to weight loss on a high fiber/high whole grain diet in accordance with the invention and includes one or more of the following PGMC: (i) patients with the *Prevotella* spp. enterotype (E2); (ii) patients with a relative abundance of log 10(*Prevotella* spp.) of greater than −3 in their microbiota; (iii) patients with a relative abundance of log 10(*Prevotella* spp./*Bacteriodes* spp.) of greater than −2 in their microbiota and preferably greater than about −0.50 in their microbiota and preferably greater than about −0.48 in their microbiota and preferably from about −0.48 to about −0.15 in their microbiota; (iv) patients with a relative abundance of Log 10(*Prevotella* spp/*Bacteroidetes* all) of greater than −2 in their microbiota; or (v) or patients with a relative abundance of Log 10(*Bacteroidetes* all/*Bacteroides* spp.) of greater than 0 in their microbiota.

As used herein the phrase "identifying a patient having at least one PGMC" includes testing a sample of the patient's microbiota to determine if a patient has at last one PGMC. The phrase "identifying a patient having at least one PGMC" also includes preexisting knowledge of whether the patient possesses at least one PGMC and therefore, obtaining and testing a sample of the patient's gut microbiota, is not necessary.

The term "high fiber diet" is used interchangeably herein with "fiber rich diet" and "diet rich in fiber and wholegrains" and refers to a diet comprising, for example, at least about 15 g of fiber per day for a man or woman. Preferably a high fiber diet comprises at least about 25 g of fiber per day for a woman or at least 38 g of fiber per day for a man. Preferably a high fiber diet comprises at about 35 g of fiber per day for a man or a woman. Preferably, the fiber in the high fiber diet is a combination of soluble and non-soluble fiber, and is preferably predominately soluble fiber. Preferably, a high fiber diet comprises at least 40 g or at least 50 g of fiber per day. Preferably a high fiber diet comprises from about 30 to about 50 or about 40 to about 55 g of fiber per day.

The term "weight loss" as used herein refers to a reduction of the total body mass, due to a mean loss of fluid, body fat or adipose tissue and/or lean mass, namely bone mineral deposits, muscle, tendon, and other connective tissue. In the context of the present disclosure, weight loss is at least partly due to a "loss of fat mass" also called "reduction of body fat".

The terms "f-BG" or "fasting blood glucose" or "fasting blood sugar" or "fasting plasma glucose" or "FPG" are all equivalent and as used herein they refer to the amount of glucose (sugar) present in the blood of a human or animal. The fasting blood glucose level may be measured, for example, after a fast of approximately 8 hours.

The term "determining" as it is used with regard to determining a patient's glucose levels including fasting plasma glucose and/or fasting insulin of a subject includes testing a sample from the patient and measuring the glucose levels using standard techniques known in the art including but not limited to drawing blood samples from a fasting patient, using finger prick tests. Other non-invasive tests may also be used to determine glucose levels of a patient. The term "determining" also covers those instances where the subject's fasting plasma glucose and/or fasting insulin is already known and additional testing of a sample from the subject is not required.

The term "low GL/low GI diet" or "low CHO/low GI diet" as used herein refers to a low-glycemic diet, which is a diet based on food selected because of their minimal alteration of circulating glucose levels. Such diets in principle also include various specific diets characterized by a reduction of total carbohydrate load, for example low-carb diets and Atkin's diets. The reduction of carbohydrates load may be achieved by increasing the fat content, for example in the low-carbohydrate high fat (LCHF) diet, or by increasing the protein content, for example high-protein diets and Paleolithic diets, or by increasing both the fat content and the protein content. In addition, all low-GI diets are examples of low GL/low GI diet. Similarly, the term "high GL/high GI diet" or "high CHO/high GI diet" as used herein refers to high-glycemic diet, which is a diet comprising food that causes a substantial alteration of circulating glucose levels.

Glycemic index (GI) and glycemic load (GL) are measures of the effect on blood glucose level after a food containing carbohydrates is consumed. Glucose has a glycemic index of 100 units, and all foods are indexed against that number. Low GI foods affect blood glucose and insulin levels less and have a slower rate of digestion and absorption. A food's GI value can be determined experimentally. For example, a measured portion of the food containing 50 grams of available carbohydrate (or 25 grams of available carbohydrate for foods that contain lower amounts of carbohydrate) is fed to 10 healthy people after an overnight fast. Finger-prick blood samples are taken at 15-30 minute intervals over the next two hours. These blood samples are used to construct a blood sugar response curve for the two-hour period. The incremental area under the curve (iAUC) is calculated to reflect the total rise in blood glucose levels after eating the test food. The GI value is calculated by dividing the iAUC for the test food by the iAUC for the reference food (same amount of glucose) and multiplying by 100 (see FIG. 1). The use of a standard food is essential for reducing the confounding influence of differences in the physical characteristics of the subjects. The average of the GI ratings from all ten subjects is published as the GI for that food.

The glycemic load (GL) of food is a number that estimates how much the food will raise a person's blood glucose level after eating it. One unit of glycemic load approximates the effect of consuming one gram of glucose. Glycemic load accounts for how much carbohydrate is in the food and how much each gram of carbohydrate in the food raises blood glucose levels. Glycemic load is based on the glycemic index (GI), and is calculated by multiplying the grams of available carbohydrate in the food times the food's GI and then dividing by 100. Throughout the present application, the glycemic load is indicated as grams/day.

The term "f-insulin" or "fasting insulin (FI)" or "fasting plasma insulin (FPI)" t as used interchangeably herein refers to the amount of insulin present in the blood of a human or animal. The fasting insulin level is measured after a fast of 8 hours and can be measured at the same time as the FPG is measured.

The term "30-minutes insulin response" as used herein refers to the insulin levels measured during an Oral Glucose Tolerance Testing (OGTT), 30 minutes after the subject intakes a dose of a simple sugar, for example glucose or dextrose.

The term "ad libitum diet" as used herein refers to a diet where the amount of daily calories intake of a subject is not restricted to a particular value. A subject following an ad libitum diet is free to eat till satiety.

As used herein a calorie restricted (CR) diet provides about 1200 to about 2000 kcal per day.

As used herein a low calorie diet (LCD) provides from about 800 to 1200 kcal per day.

As used herein a very low calorie diet (VLCD) provides about 800 or fewer kcal per day.

The present invention is based in part on the discovery that the relative abundance of certain gut microbiota are an important biomarker associated with dietary weight change on ad libitum high fiber diets such as the NND. The inventors found that individuals with at least one PGMC selected from (i) patients with the *Prevotella* spp. enterotype (E2); (ii) patients with a relative abundance of log 10(*Prevotella* spp.) of greater than −3 in their microbiota; (iii) patients with a relative abundance of log 10(*Prevotella* spp./*Bacteriodes* spp.) of greater than −2 in their microbiota and preferably greater than about −0.50 in their microbiota and preferably greater than about −0.48 in their microbiota and preferably from about −0.48 to about −0.15 in their microbiota; or (iv) patients with a relative abundance of Log 10(*Prevotella* spp/*Bacteroidetes* all) of greater than −2 in their microbiota; are extremely susceptible to weight loss on a diet rich in fiber and whole grain as compared to "western" diets having lower dietary fiber.

Preferably, the invention provides methods for predicting dietary weight loss in a patient comprising the steps of: (a) identifying a patient having at least one preferred gut microbiota characteristic (PGMC) selected from: i) patients with the *Prevotella* spp. enterotype (E2), (ii) patients with a relative abundance of log 10(*Prevotella* spp.) of greater than −3 in their microbiota, (iii) patients with a relative abundance of log 10(*Prevotella* spp./*Bacteriodes* spp.) of greater than −2 in their microbiota and preferably greater than about −0.50 in their microbiota and preferably greater than about −0.48 in their microbiota, and preferably from about −0.48 to about −0.15 in their microbiota, (iv) patients with a relative abundance of Log 10(*Prevotella* spp/*Bacteroidetes* all) of greater than −2 in their microbiota, and (v) patients with a relative abundance of Log 10(*Bacteroidetes* all/*Bacteroides* spp.) of greater than 0 in their microbiota; and (b) predicting dietary weight loss success of the patient on a predetermined diet. Preferably, the predetermined diet is a high fiber and wholegrain diet. Preferably, the high fiber/high wholegrain diet is the New Nordic Diet (NND). Preferably, the predetermined diet is selected from Diets 1-10 of Table 1. Preferably the patient or patient being treated is obese or overweight. Preferably the patient being treated is Caucasian. Preferably the patient is of Nordic ethnicity. Preferably the predictability of weight loss in a patient on a predetermined diet is further improved by determining the patient's FI and FPG. Preferably the patient also has at least one or more of (i) elevated fasting blood glucose levels or (ii) low fasting blood insulin levels.

A patient having at least one PGMC may be identified based on samples taken of the patient's gut microbiota. There are several ways to obtain samples of the said patient's gut microbial DNA. For example, it is possible to prepare mucosal specimens, or biopsies, obtained by colonoscopy. However, a preferred method for obtaining a sample is fecal analysis, a procedure which has been reliably used in the art. Feces contain about 1011 bacterial cells per gram (wet weight) and bacterial cells comprise about 50% of fecal mass. The microbiota of the feces represents primarily the microbiology of the distal large bowel. It is thus possible to isolate and analyze large quantities of microbial DNA from the feces of an individual. By "gut microbial DNA", it is herein understood the DNA from any of the resident bacterial communities of the human gut. The term "gut microbial DNA" encompasses both coding and non-coding sequences; it is, in particular, not restricted to complete genes, but also comprises fragments of coding sequences. Fecal analysis is thus a non-invasive procedure, which yields consistent and directly-comparable results from patient to patient.

The enterotype and/or relative abundance of one or more gut microbiota species may be determined in various ways which have been set out in Arumugam et al. 2011, supra. For example, the enterotype may be determined by determining the level of bacteria belonging to the enterotype genera. One of the most researched microbial nucleic acids is that of the 16S rRNA. This 16S rRNA, also known as small subunit (SSU) RNA, is encoded by an approximately 1500 bp gene that is present in a variable number of copies, usually 1-10 per microbial genome. The nucleotide sequence of the 16S rRNA genes is frequently used in diagnostics as it shows differences between microbial species. The level of bacteria belonging to E1, E2 and/or E3 may be measured by determining the level of specific nucleic acid sequences in said test sample, which nucleic acid sequences are preferably 16S rRNA gene sequences of said one or more bacteria, more preferably one or more variable regions of said 16S rRNA gene sequences, e.g., one or more of the variable regions V1 and/or V6 of said 16S rRNA gene sequences.

Preferably, the assignment of the gut microbiota of a patient as enterotype 2 (E2) which has a relative abundance of *Prevotella* spp. bacteria is predictive of the patient's enhanced susceptibility to weight loss on a diet rich in fiber and whole grain as compared to a diet that is not high in fiber and wholegrains. Preferably, the gut microbiota of a patient having a relative abundance of *Prevotella* spp. bacteria is predictive of the patient's enhanced susceptibility to weight loss on a diet rich in fiber and whole grain as compared to a diet that is not high in fiber and wholegrains.

Preferably the assignment of the gut microbiota of a patient as having a relative abundance of log 10(*Prevotella* spp.) of greater than −3 is predictive of the patient's enhanced susceptibility to weight loss on a diet rich in fiber and whole grain as compared to a diet that is not high in fiber and wholegrains.

Preferably the assignment of the gut microbiota of a patient as having a relative abundance of log 10(*Prevotella* spp./*Bacteriodes* spp.) of greater than −2, preferably greater than about −0.50, and preferably greater than about −0.48 and preferably from about −0.48 to −0.15, is predictive of the patient's enhanced susceptibility to weight loss on a diet rich in fiber and whole grain as compared to a diet that is not high in fiber and wholegrains.

Preferably the assignment of the gut microbiota of a patient as having a relative abundance of log 10(*Prevotella* spp./*Bacteroidetes* all) of greater than −2 is predictive of the patient's enhanced susceptibility to weight loss on a diet rich in fiber and whole grain as compared to a diet that is not high in fiber and wholegrains.

Preferably the assignment of the gut microbiota of a patient as having a relative abundance of Log 10(*Bacteroidetes* all/*Bacteroides* spp.) of greater than 0 is predictive of the patient's enhanced susceptibility to weight loss on a diet rich in fiber and whole grain as compared to a diet that is not high in fiber and wholegrains.

Therefore, the invention also preferably provides methods of promoting weight loss in a patient identified as having at least one or more PGMC comprising the steps of administering to the patient a diet that is high in fiber and whole grain. Preferably the high fiber/high wholegrain diet is the New Nordic Diet (NND). Preferably the predetermined diet is selected from Diets 1-10 of Table 1. Preferably the patient is overweight or obese. The above-described methods of the invention as described above can also be used to manage or maintain weight, i.e., prevent or inhibit weight gain, in a patient who is of normal weight or is overweight. Preferably the patient is Caucasian. Preferably the patient is of Nordic ethnicity.

Preferably, the invention further provides methods of predicting dietary weight loss in a patient comprising the steps of identifying a patient having at least one PGMC in combination with determining the patient's FI or FPG and including determining if a patient has one or more of (i) elevated fasting blood glucose levels and (ii) low fasting blood insulin levels and predicting dietary weight loss success of the patient on a predetermined diet such as a diet that is high in fiber and whole grain, based on whether the patient has at least one PGMC in combination with the patient's FPG and FI including if a patient has one or more of (i) elevated fasting blood glucose levels and (ii) the patient is not insulin resistant.

An elevated baseline fasting blood glucose level in a patient is, for example, about 90 mg/dL or higher or about 93 or 95 mg/dL or higher. Patients with fasting blood glucose levels in this range include those with fasting blood glucose levels at the high end of the normal range (90 to under 100 mg/dL), prediabetics (blood glucose levels of 100-125.9 mg/dL) and diabetics (blood glucose levels of 126 mg/dL or higher).

Preferably, determining a patient's FPG includes classifying a patient's FPG into one of the following levels of FPG: i) a patient having an FPG of less than about 90 mg/dL; (ii) a patient having an FPG of between about 90-100 mg/dL; (iii) a patient having an FPG of between about 100 mg/dL-115 mg/dL; (iv) a patient having an FPG between about 115-125 mg/dL; and (v) a patient having greater than about 125 mg/dL.

Preferably, determining the patient's FI includes classifying the patient's FI into one of the following levels of FI: i) a patient having an FI of below about 9.5 uU/ml; (ii) a patient having an FI above about 13 uU/ml; and (iii) a patient having an FI between about 9.5 to 13 uU.

The absence of insulin resistance may be determined using any test used to identify insulin resistance, such as determining the patient's fasting blood insulin level or a 2-hour oral glucose tolerance test. In one embodiment, the absence of insulin resistance is determined by measuring the patient's fasting blood insulin level. The patient preferably has a normal baseline fasting blood insulin level, for example, a fasting insulin level of about 24 µIU/mL or less. Preferably the patient has a fasting blood insulin level of about 20 µIU/mL or less, about 15 µIU/mL or less or about 10 µIU/mL or less. More preferably, the patient has a fasting blood insulin level of less than 10 µIU/mL.

Preferably, the absence of insulin resistance is determined by a 2-hour oral glucose tolerance test. Preferably, the patient has a normal 2-hour glucose tolerance test result, for example a result of less than about 140 mg/dL.

Preferably, the patient has a fasting blood glucose level of about 90 mg/mL or higher, about 93 or 95 mg/dL or higher or about 100 mg/mL or higher, and a fasting blood insulin level of about 24 µIU/mL or less, about 20 µIU/mL or less, about 15 µIU/mL or less or about 10 µIU/mL or less. Preferably, the patient has a fasting blood glucose level of about 90 mg/mL or higher and a fasting blood insulin level of about 24 µIU/mL or less, about 20 µIU/mL or less, about 15 µIU/mL or less or about 10 µIU/mL or less. Preferably, the patient has a fasting blood glucose level of about 93 mg/mL or higher and a fasting blood insulin level of about 24 µIU/mL or less, about 20 µIU/mL or less, about 15 µIU/mL or less, or about 10 µIU/mL or less. Preferably, the patient has a fasting blood glucose level of about 95 mg/mL or higher and a fasting blood insulin level of about 24 µIU/mL or less, about 20 µIU/mL or less, about 15 µIU/mL or less, or about 10 µIU/mL or less. Preferably, the patient has a fasting blood glucose level of about 100 mg/mL or higher and a fasting blood insulin level of about 24 µIU/mL or less, about 20 µIU/mL or less, about 15 µIU/mL or less, or about 10 μIU/mL or less. Preferably, the patient has a fasting blood glucose level of about 90 mg/mL or higher, about 93 or 95 mg/dL or higher or about 100 mg/mL or higher, and a fasting blood insulin level of less than 10 μIU/mL.

The fasting blood glucose, fasting blood insulin and glucose tolerance test measurements described herein are preferably baseline measurements, that is, the values of the disclosed physiological parameters prior to initiating a method of treatment as described herein. More preferably, such measurements are made in the absence of therapy intended to lower fasting blood glucose levels.

Without being limited to any theory, previous research by the inventors has indicated that simple fasting glucose (FPG) and/or fasting insulin (FI) measurements can be a predictor of dietary weight loss success of a subject on certain diets (U.S. Provisional Application No. 62/403,946 entitled Methods of Inducing Weight Loss, Treating Obesity and Preventing Weight Gain). It was previously found that non-diabetic overweight or obese people with high FPG lose more weight than non-diabetic overweight or obese people with a low FPG who are on a low glycemic index (GI)/low glycemic load (GL) diet, such as on a high fiber diet rich in whole grain. Therefore, the combination of identifying whether a patient has at least one PGMC in combination with one or more of (i) measurements of FPG and (ii) FI and/or 30 minute insulin response may improve the predictive power of the methods of the invention.

Table 1 provides recommended Diets 1-10 based on fasting glucose (FPG) and fasting insulin (FI) for individuals with the *Prevotella* enterotype and optionally including individuals of the *Bacteroides* enterotype if their relative abundance of *Prevotella* is below 0.000001 and is preferably below 0.0000005.

TABLE 1

| | Below FI of 9.5 uU/mL or if FI is between 9.5 to 13 uU/mL* | Above FI of 13 uU/mL or if FI is between 9.5 to 13 uU/mL* |
|---|---|---|
| **FPG >125 mg/dL | Carbohydrate: 34 (32-36)%<br>Protein: 21 (19-23)%<br>Fat: 45 (43-47)%<br>Fiber: >25 g/10 MJ (preferably >35)<br>Added sugar: <5E %<br>DIET 9 | Carbohydrate: 30 (28-32)%<br>Protein: 25 (23-27)%<br>Fat: 45 (43-47)%<br>Fiber: >20 g/10 MJ (preferably >25)<br>Added sugar: <5E %<br>DIET 10 |
| FPG 115-125 mg/dL | Carbohydrate: 39 (37-41)%<br>Protein: 21 (19-23)%<br>Fat: 40 (38-42)%<br>Fiber: >30 g/10 MJ (preferably >40)<br>Added sugar: <10E % (preferably <5E %)<br>DIET 7 | Carbohydrate: 33 (31-35)%<br>Protein: 25 (23-27)%<br>Fat: 42 (40-44)%<br>Fiber: >20 g/10 MJ (preferably >30)<br>Added sugar: <5E %<br>DIET 8 |
| FPG 100-115 mg/dL | Carbohydrate: 44 (42-46)%<br>Protein: 21 (19-23)%<br>Fat: 35 (33-37)%<br>Fiber: >30 g/10 MJ (preferably >40)<br>Added sugar: <15E % (preferably <5E %)<br>DIET 5 | Carbohydrate: 37 (35-39)%<br>Protein: 25 (23-27)%<br>Fat: 38 (36-40)%<br>Fiber: >25 g/10 MJ (preferably >35)<br>Added sugar: <10E % (preferably <5E %)<br>DIET 6 |
| FPG 90-100 mg/dL | Carbohydrate: 49 (47-51)%<br>Protein: 21 (19-23)%<br>Fat: 30 (28-32)%<br>Fiber: >30 g/10 MJ (preferably >40)<br>Added sugar: <15E % (preferably <5E %)<br>DIET 3 | Carbohydrate: 40 (38-42)%<br>Protein: 25 (23-27)%<br>Fat: 35 (33-37)%<br>Fiber: >25 g/10 MJ (preferably >35)<br>Added sugar: <10E % (preferably <5E %)<br>DIET 4 |
| FPG <90 mg/dL | Carbohydrate: 54 (52-56)%<br>Protein: 21 (19-23)%<br>Fat: 25 (23-27)%<br>Fiber: >30 g/10 MJ (preferably >40)<br>Added sugar: <15E % (preferably <5E %)<br>DIET 1 | Carbohydrate: 30 (28-32)%<br>Protein: 25 (23-27)%<br>Fat: 45 (43-47)%<br>Fiber: >20 g/10 MJ (preferably >25)<br>Added sugar: <5E %<br>DIET 2 |

*For individuals having FI between 9.5 to 13 uU/mL there are two optional diets as described above. For example, an individual having FPG of 130 mg/dL and FI of 10 uU/mL could be assigned to different diet combinations with a range of carbohydrate between 28% and 36%, which is the combined range of the diets on the two FI ranges.
**Individuals treated with diabetes medication such as Metformin or others should be treated as if their FPG is greater than 125 mg/dL, regardless of what their tested FPG is due to normalization of FPG by the medication.
Note:
The energy percentage from carbohydrates is available carbohydrates and therefore do not include fibers. For example: an individual consumes 10 MJ. If consuming 40, 40, and 20E % from available carbohydrates, fats and proteins, respectively you would immediately think that 4, 4, and 2 MJ of energy comes from these macronutrients. However, if fibers contribute with 0.5 MJ these is only 9.5 MJ to split between the three macronutrients.

Therefore, the invention provides methods predicting dietary weight loss in a subject comprising the steps of:
(a) identifying a subject with at least one preferred gut microbiota characteristic (PGMC) selected from: i) patients with the *Prevotella* spp. enterotype (E2), (ii) patients with a relative abundance of log 10(*Prevotella* spp.) of greater than −3 in their microbiota, (iii) patients with a relative abundance of log 10(*Prevotella* spp./*Bacteriodes* spp.) of greater than −2 in their microbiota and preferably greater than about −0.50 in their microbiota and preferably greater than about −0.48 in their microbiota and preferably from about −0.48 to about −0.15 in their microbiota, (iv) patients with a relative abundance of Log 10(*Prevotella* spp./*Bacteroidetes* all) of greater than −2 in their microbiota, and (v) patients with a relative abundance of Log 10(*Bacteroidetes* all/*Bacteroides* spp.) of greater than 0 in their microbiota.

(b) predicting the dietary weight loss success of the patient having at least one PGMC on a predetermined diet wherein the predetermined diet is selected based on the patient's FPG and FI wherein the predetermined diet is selected from the group consisting of:

when the subject's FPG is less than about 90 mg/dL and the subject's FI is below about 9.5 uU/mL or optionally the subject's FI is between about 9.5 to about 13 uU/mL, the predetermined diet comprises Diet 1;

when the subject's FPG is less than about 90 mg/dL and the subject's FI is above about 13 uU/mL or optionally the subject's FI is between about 9.5 to about 13 uU/mL, the predetermined diet comprises Diet 2;

when the subject's FPG is between about 90-100 mg/dL and the subject's FI is below about 9.5 uU/mL or optionally the subject's FI is between about 9.5 to about 13 uU/mL, the predetermined diet comprises Diet 3;

when the subject's FPG is between about 90-100 mg/dL and the subject's FI is above about 13 uU/mL or optionally the subject's FI is between about 9.5 to about 13 uU/mL, the predetermined diet comprises Diet 4;

when the subject's FPG is between about 100-115 mg/dL and the subject's FI is below about 9.5 uU/mL or optionally the subject's FI is between about 9.5 to about 13 uU/mL, the predetermined diet comprises Diet 5;

when the subject's FPG is between about 100-115 mg/dL and the subject's FI is above about 13 uU/mL or optionally the subject's FI is between about 9.5 to about 13 uU/mL, the predetermined diet comprises Diet 6;

when the subject's FPG is between about 115-125 mg/dL and the subject's FI is below about 9.5 uU/mL or optionally the subject's FI is between about 9.5 to about 13 uU/mL, the predetermined diet comprises Diet 7;

when the subject's FPG is between about 115-125 mg/dL and the subject's FI is above about 13 uU/mL or optionally the subject's FI is between 9.5 to 13 uU/mL, the predetermined diet comprises Diet 8;

when the subject's FPG is greater than about 125 mg/dL and the subject's FI is below about 9.5 uU/mL or optionally the subject's FI is between about 9.5 to about 13 uU/mL, the predetermined diet comprises Diet 9; and when the subject's FPG is greater than about 125 mg/dL and the subject's FI is above about 13 uU/mL or optionally the subject's FI is between about 9.5 to about 13 uU/mL, the predetermined diet comprises Diet 10.

The invention further provides methods of promoting weight loss in a patient comprising, administering a predetermined diet to a patient wherein the patient has at least one PGMC selected from: i) patients with the *Prevotella* spp. enterotype (E2), (ii) patients with a relative abundance of log 10(*Prevotella* spp.) of greater than −3 in their microbiota, (iii) patients with a relative abundance of log 10(*Prevotella* spp./*Bacteriodes* spp.) of greater than −2 in their microbiota and preferably greater than about −0.50 in their microbiota and preferably greater than about −0.48 in their microbiota and preferably from about −0.48 to about −0.15 in their microbiota, (iv) patients with a relative abundance of Log 10(*Prevotella* spp./*Bacteroidetes* all) of greater than −2 in their microbiota, and (v) patients with a relative abundance of Log 10(*Bacteroidetes* all/*Bacteroides* spp.) of greater than 0 in their microbiota and wherein the predetermined diet selected for promoting weight loss in the patient is further based on the patient's FPG and FI and is selected from the group consisting of:

when the subject's FPG is less than about 90 mg/dL and the subject's FI is below about 9.5 uU/mL or optionally the subject's FI is between about 9.5 to about 13 uU/mL, the predetermined diet comprises Diet 1;

when the subject's FPG is less than about 90 mg/dL and the subject's FI is above about 13 uU/mL or optionally the subject's FI is between about 9.5 to about 13 uU/mL, the predetermined diet comprises Diet 2;

when the subject's FPG is between about 90-100 mg/dL and the subject's FI is below about 9.5 uU/mL or optionally the subject's FI is between about 9.5 to about 13 uU/mL, the predetermined diet comprises Diet 3;

when the subject's FPG is between about 90-100 mg/dL and the subject's FI is above about 13 uU/mL or optionally the subject's FI is between about 9.5 to about 13 uU/mL, the predetermined diet comprises Diet 4;

when the subject's FPG is between about 100-115 mg/dL and the subject's FI is below about 9.5 uU/mL or optionally the subject's FI is between about 9.5 to about 13 uU/mL, the predetermined diet comprises Diet 5;

when the subject's FPG is between about 100-115 mg/dL and the subject's FI is above about 13 uU/mL or optionally the subject's FI is between about 9.5 to about 13 uU/mL, the predetermined diet comprises Diet 6;

when the subject's FPG is between about 115-125 mg/dL and the subject's FI is below about 9.5 uU/mL or optionally the subject's FI is between about 9.5 to about 13 uU/mL, the predetermined diet comprises Diet 7;

when the subject's FPG is between about 115-125 mg/dL and the subject's FI is above about 13 uU/mL or optionally the subject's FI is between 9.5 to 13 uU/mL, the predetermined diet comprises Diet 8;

when the subject's FPG is greater than about 125 mg/dL and the subject's FI is below about 9.5 uU/mL or optionally the subject's FI is between about 9.5 to about 13 uU/mL, the predetermined diet comprises Diet 9; and when the subject's FPG is greater than about 125 mg/dL and the subject's FI is above about 13 uU/mL or optionally the subject's FI is between about 9.5 to about 13 uU/mL, the predetermined diet comprises Diet 10.

The invention also provides changing a subject's predetermined diet based on fluctuations or improvements in the patient's FPG and FI for to optimize weight loss in the patient. For example, if a patient's original FPG is greater than about 125 mg/dL and after following predetermined Diet 10 for a period of time (e.g. days, weeks or months) the patient's FPG is determined to be less than about 9.5, the patient may be moved to predetermined Diet 1 or Diet 2 depending on the patient's FI.

Preferably, for those patients whom the fiber intake before the treatment was the same or above the amount which is recommended based on Table 1, the recommended carbohydrate intake should be reduced by 10 to 20%, and the protein and fat intake should be increased instead in equal amounts to balance the diet for at least a period of at least 1 week, preferably at least 2 weeks, preferably at least 3 weeks, preferably at least 4 weeks preferably at least 5 weeks, preferably at least 6 weeks preferably at least 7 weeks preferably at least 8 weeks or more prior to commencing a diet of Table 1.

Preferably, patients who receive a prediction for optimized weight loss and a recommendation to follow a particular diet in accordance with Table 1 are Caucasian patients.

Also provided are methods for predicting weight loss and promoting weight loss in patients having low relative abundance of *Prevotella* spp. preferably excluding individuals having very low relative abundance of *Prevotella* spp. For example, below 0.000001 and preferably below about 0.0000005. Table 2 provides recommended Diets 11-20 based on fasting glucose (FPG) and fasting insulin (FI) for individuals with the low relative abundance of *Prevotella* and preferably excluding individuals having very low relative abundance of *Prevotella*, for example, is below 0.000001 or preferably below 0.0000005.

TABLE 2

| For individuals with the following FI: | Below FI of 9.5 uU/mL or if FI is between 9.5 to 13 uU/mL* | Above FI of 13 uU/mL or if FI is between 9.5 to 13 uU/mL* |
|---|---|---|
| **FPG >125 mg/dL | Carbohydrate: 30 (28-32)%<br>Protein: 30 (28-32)%<br>Fat: 40 (38-42)%<br>Fiber: >12 g/10 MJ (preferably >16)<br>Added sugar: <5E %<br>Diet 19 | Carbohydrate: 25 (23-27)%<br>Protein: 30 (28-32)%<br>Fat: 45 (43-47)%<br>Fiber: >12 g/10 MJ (preferably >16)<br>Added sugar: <5E %<br>Diet 20 |
| FPG 115-125 mg/dL | Carbohydrate: 35 (33-37)%<br>Protein: 30 (28-32)%<br>Fat: 35 (33-37)%<br>Fiber: >12 g/10 MJ (preferably >16)<br>Added sugar: <10E %<br>(preferably <5E %)<br>Diet 17 | Carbohydrate: 30 (28-32)%<br>Protein: 30 (28-32)%<br>Fat: 40 (38-42)%<br>Fiber: >12 g/10 MJ (preferably >16)<br>Added sugar: <5E %<br>Diet 18 |
| FPG 100-115 mg/dL | Carbohydrate: 40 (38-42)%<br>Protein: 30 (28-32)%<br>Fat: 30 (28-32)%<br>Fiber: >12 g/10 MJ (preferably >16)<br>Added sugar: <10E %<br>(preferably <5E %)<br>Diet 15 | Carbohydrate: 35 (33-37)%<br>Protein: 30 (28-32)%<br>Fat: 35 (33-37)%<br>Fiber: >12 g/10 MJ (preferably >16)<br>Added sugar: <10E %<br>(preferably <5E %)<br>Diet 16 |
| FPG 90-100 mg/dL | Carbohydrate: 40 (38-42)%<br>Protein: 30 (28-32)%<br>Fat: 30 (28-32)%<br>Fiber: >12 g/10 MJ (preferably >16)<br>Added sugar: <10E %<br>(preferably <5E %)<br>Diet 13 | Carbohydrate: 35 (33-37)%<br>Protein: 30 (28-32)%<br>Fat: 35 (33-37)%<br>Fiber: >12 g/10 MJ (preferably >16)<br>Added sugar: <10E %<br>(preferably <5E %)<br>Diet 14 |
| FPG <90 mg/dL | Carbohydrate: 40 (38-42)%<br>Protein: 30 (28-32)%<br>Fat: 30 (28-32)%<br>Fiber: >12 g/10 MJ (preferably >16)<br>Added sugar: <10E %<br>(preferably <5E %)<br>Diet 11 | Carbohydrate: 25 (23-27)%<br>Protein: 30 (28-32)%<br>Fat: 45 (43-47)%<br>Fiber: >12 g/10 MJ (preferably >16)<br>Added sugar: <5E %<br>Diet 12 |

*For individuals having FI between 9.5 to 13 uU/mL there are two optional diets as described above. For example, an individual having FPG of 130 mg/dL and FI of 10 uU/mL could be assigned to different diet combinations with a range of carbohydrate between 23% and 32%, which is the combined range of the diets on the two FI ranges.
**Individuals treated with diabetes medication such as Metformin or others should be treated as if their FPG is greater than 125 mg/dL, regardless of what their tested FPG is due to normalization of FPG by the medication.
Note:
The energy percentage from carbohydrates is available carbohydrates and therefore do not include fibers. For example: an individual consumes 10 MJ. If consuming 40, 40, and 20E % from available carbohydrates, fats and proteins, respectively you would immediately think that 4, 4, and 2 MJ of energy comes from these macronutrients. However, if fibers contribute with 0.5 MJ these is only 9.5 MJ to split between the three macronutrients.

Therefore, the invention provides methods predicting dietary weight loss in a subject comprising the steps of:
(a) identifying a subject with low relative abundance of *Prevotella* spp. optionally wherein the relative abundance of *Prevotella* spp.is less than about 0.000001 and preferably less than about 0.0000005.
(b) predicting the dietary weight loss success of the patient low relative abundance of *Prevotella* spp on a predetermined diet wherein the predetermined diet is selected based on the patient's FPG and FI and wherein the predetermined diet is selected from the group consisting of:

when the subject's FPG is less than about 90 mg/dL and the subject's FI is below about 9.5 uU/mL or optionally the subject's FI is between about 9.5 to about 13 uU/mL, the predetermined diet comprises Diet 11;

when the subject's FPG is less than about 90 mg/dL and the subject's FI is above about 13 uU/mL or optionally the subject's FI is between about 9.5 to about 13 uU/mL, the predetermined diet comprises Diet 12;

when the subject's FPG is between about 90-100 mg/dL and the subject's FI is below about 9.5 uU/mL or optionally the subject's FI is between about 9.5 to about 13 uU/mL, the predetermined diet comprises Diet 13;

when the subject's FPG is between about 90-100 mg/dL and the subject's FI is above about 13 uU/mL or optionally the subject's FI is between about 9.5 to about 13 uU/mL, the predetermined diet comprises Diet 14;

when the subject's FPG is between about 100-115 mg/dL and the subject's FI is below about 9.5 uU/mL or optionally the subject's FI is between about 9.5 to about 13 uU/mL, the predetermined diet comprises Diet 15;

when the subject's FPG is between about 100-115 mg/dL and the subject's FI is above about 13 uU/mL or optionally the subject's FI is between about 9.5 to about 13 uU/mL, the predetermined diet comprises Diet 16;

when the subject's FPG is between about 115-125 mg/dL and the subject's FI is below about 9.5 uU/mL or optionally the subject's FI is between about 9.5 to about 13 uU/mL, the predetermined diet comprises Diet 17;

when the subject's FPG is between about 115-125 mg/dL and the subject's FI is above about 13 uU/mL or optionally the subject's FI is between 9.5 to 13 uU/mL, the predetermined diet comprises Diet 18;

when the subject's FPG is greater than about 125 mg/dL and the subject's FI is below about 9.5 uU/mL or optionally the subject's FI is between about 9.5 to about 13 uU/mL, the predetermined diet comprises Diet 19; and when the subject's FPG is greater than about 125 mg/dL and the subject's FI is above about 13 uU/mL or optionally the subject's FI is between about 9.5 to about 13 uU/mL, the predetermined diet comprises Diet 20.

The invention further provides methods of promoting weight loss in a patient comprising, administering a predetermined diet to a patient wherein the patient has a low relative abundance of *Prevotella* spp. optionally wherein the relative abundance of *Prevotella* spp.is less than about 0.000001 and preferably less than about 0.0000005, wherein the predetermined diet is selected based on the patient's FPG and FI and wherein the predetermined diet is selected from the group consisting of:

when the subject's FPG is less than about 90 mg/dL and the subject's FI is below about 9.5 uU/mL or optionally the subject's FI is between about 9.5 to about 13 uU/mL, the predetermined diet comprises Diet 11;

when the subject's FPG is less than about 90 mg/dL and the subject's FI is above about 13 uU/mL or optionally the subject's FI is between about 9.5 to about 13 uU/mL, the predetermined diet comprises Diet 12;

when the subject's FPG is between about 90-100 mg/dL and the subject's FI is below about 9.5 uU/mL or optionally the subject's FI is between about 9.5 to about 13 uU/mL, the predetermined diet comprises Diet 13;

when the subject's FPG is between about 90-100 mg/dL and the subject's FI is above about 13 uU/mL or optionally the subject's FI is between about 9.5 to about 13 uU/mL, the predetermined diet comprises Diet 14;

when the subject's FPG is between about 100-115 mg/dL and the subject's FI is below about 9.5 uU/mL or optionally the subject's FI is between about 9.5 to about 13 uU/mL, the predetermined diet comprises Diet 15;

when the subject's FPG is between about 100-115 mg/dL and the subject's FI is above about 13 uU/mL or optionally the subject's FI is between about 9.5 to about 13 uU/mL, the predetermined diet comprises Diet 16;

when the subject's FPG is between about 115-125 mg/dL and the subject's FI is below about 9.5 uU/mL or optionally the subject's FI is between about 9.5 to about 13 uU/mL, the predetermined diet comprises Diet 17;

when the subject's FPG is between about 115-125 mg/dL and the subject's FI is above about 13 uU/mL or optionally the subject's FI is between 9.5 to 13 uU/mL, the predetermined diet comprises Diet 18;

when the subject's FPG is greater than about 125 mg/dL and the subject's FI is below about 9.5 uU/mL or optionally the subject's FI is between about 9.5 to about 13 uU/mL, the predetermined diet comprises Diet 19; and when the subject's FPG is greater than about 125 mg/dL and the subject's FI is above about 13 uU/mL or optionally the subject's FI is between about 9.5 to about 13 uU/mL, the predetermined diet comprises Diet 20.

The invention also provides changing a subject's predetermined diet based on fluctuations or improvements in the patient's FPG and FI for to optimize weight loss in the patient. For example, if a patient's original FPG is greater than about 125 mg/dL and after following predetermined Diet 20 for a period of time (e.g., days, weeks or months) the patient's FPG is determined to be less than about 9.5, the patient may be moved to predetermined Diet 11 or Diet 12 depending on the patient's FI.

Preferably, for those patients whom the fiber intake before the treatment was the same or above the amount which is recommended based on Table 1, the recommended carbohydrate intake should be reduced by 10 to 20%, and the protein and fat intake should be increased instead in equal amounts to balance the diet for at least a period of at least 1 week, preferably at least 2 weeks, preferably at least 3 weeks, preferably at least 4 weeks preferably at least 5 weeks, preferably at least 6 weeks preferably at least 7 weeks preferably at least 8 weeks or more prior to commencing a diet of Table 2.

The invention also provides methods for predicting a patient's ability to maintain weight loss on a predetermined diet based on determining whether the patient has low relative abundance of *Prevotella* or high relative abundance of *Prevotella* in combination with determining whether the patient has low fasting insulin (FI) or high FI.

In conjunction with the diagnostic and predictive methods of the invention based on the discovery that the presence of at least one PGMC in a patient's gut microbiota is predictive of whether the patient will be highly susceptible to weight loss on a high fiber/high whole grain diet, the invention also provides therapeutic methods for promoting weight loss and treating obesity. Preferably the invention provides methods of promoting weight loss on a high fiber/high whole grain diet comprising the step of altering the microbiota population in the patient to achieve at least one PGMC. Preferably the patient's microbiota is altered by increasing the relative abundance of *Prevotella* spp. Preferably the patient's microbiota is altered by decreasing the relative abundance of *Bacteriodes* spp. Preferably the patient's microbiota is altered to increase the relative abundance of *Prevotella* spp. by administering to the patient a probiotic comprising *Prevotella* spp. Probiotics useful in the methods of the present invention can comprise live bacterial strains and/or spores. In a preferred embodiment, such live bacterial strains and/or spores are from the genus *Prevotella* spp.

One or several different bacterial inoculants can be administered simultaneously or sequentially (including administering at different times). Such bacteria can be isolated from microbiota and grown in culture using known techniques.

Preferably, the bacterial inoculant used in the methods of the invention further comprises a buffering agent. Examples of useful buffering agents include sodium bicarbonate, juice, milk, yogurt, infant formula, and other dairy products.

Administration of a bacterial inoculant can be accomplished by any method likely to introduce the organisms into the desired location. In a preferred embodiment, bacteria are administered orally. Alternatively, bacteria can be administered rectally, by enema, by esophagogastroduodenoscopy, colonoscopy, nasogastric tube, or orogastric tube.

The bacteria can be mixed with an excipient, diluent or carrier selected with regard to the intended route of administration and standard pharmaceutical practice. For easier delivery to the digestive tract, bacteria can be applied to liquid or solid food, or feed or to drinking water. For oral administration, bacteria can be also formulated in a capsule. The capsule can be coated so that it is not dissolved before it enters the lower part of the gut so a larger proportion of the bacteria survive into the large intestine. The excipient, diluent and/or carrier must be "acceptable" in the sense of being compatible with the other ingredients of the formulation and should be non-toxic to the bacteria and the patient/patient. Preferably, the excipient, diluent and/or carrier contains an ingredient that promotes viability of the bacteria during storage.

The formulation can include added ingredients to improve palatability, improve shelf-life, impart nutritional benefits, and the like. Acceptable excipients, diluents, and carriers for therapeutic use are well known in the pharmaceutical art. The choice of pharmaceutical excipient, diluent, and carrier can be selected with regards to the intended route of administration and standard pharmaceutical practice.

The dosage of the bacterial inoculant or compound of the invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization of the intestinal tract with the desired bacterial inoculant, e.g. $10^6$, $10^7$, $10^8$, $10^9$, and $10^{10}$ CFU for example, can be administered in a single dose. Lower doses can also be effective, e.g., $10^4$, and $10^5$ CFU.

Preferably, the relative abundance of gut *Prevotella* spp. within an individual patient may be increased by about 1% to about 100%. Preferably, the relative abundance of *Prevotella* spp. may be altered by an increase of from about 20% to about 100%, from about 30% to about 100%, from about 40% to about 100%, from about 50% to about 100%, from about 60% to about 100%, from about 70% to about 100%, from about 80% to about 100%, or from about 90% to about 100%. Preferably, the relative abundance of *Prevotella* spp. may be altered by an increase of from about 10% to about 90%, from about 20% to about 80%, or from about 40% to about 60%.

Preferably, the relative abundance of gut *Bacteriodes* spp. within an individual may be reduced by about 1% to about 100%. Preferably, the relative abundance of *Bacteriodes* spp. may be reduced by about 20%, by about 30%, by about 40%, by about 50%, by about 60%, by about 70%, by about 100%, by about 80%, by about 90% or by about 100%. Decreased relative abundance of *Bacteroides* spp. in the gut may be accomplished by several suitable means generally known in the art. In one embodiment, an antibiotic having efficacy against *Bacteroides* spp. may be administered to the patient by any suitable means including, but not limited to orally and intravenously. Generally speaking, antimicrobial agents may target several areas of bacterial physiology: protein translation, nucleic acid synthesis, folic acid metabolism, or cell wall synthesis. In an exemplary embodiment, the antibiotic will have efficacy against *Bacteroides* spp. but not against *Prevotella* spp. The susceptibility of the targeted species to the selected antibiotics may be determined based on culture methods or genome screening.

The following non-limiting examples further describe the invention.

Example 1: Pre-Treatment Microbial Enterotype, Inferred from the *Prevotella*-to-*Bacteroides* Ratio, Determines Weight Loss Success During a 6-Month Randomized Controlled Diet Intervention Abstract Based on the abundance of specific bacterial genera, the human gut microbiota can be divided into two relatively stable groups that might play a role in personalized nutrition. We studied these simplified enterotypes as prognostic markers for successful body fat loss on two different diets. A total of 62 participants with increased waist circumference were randomly assigned to receive an ad libitum New Nordic Diet (NND) high in fiber/wholegrain or an Average Danish Diet (ADD) for 26 weeks. Participants were grouped into two discrete enterotypes by their relative abundance of *Prevotella* spp. divided by *Bacteroides* spp. (P/B ratio) obtained by quantitative PCR analysis. Modifications of dietary effects of pre-treatment P/B group were examined by linear mixed models. Among individuals with high P/B the NND resulted in a 3.15 kg (95% CI 1.55;4.76, P<0.001) larger body fat loss compared to ADD whereas no differences were observed among individuals with low P/B (0.88 kg [95% CI −0.61;2.37, P=0.25]). Consequently, a 2.27 kg (95% CI 0.09;4.45, P=0.041) difference in responsiveness to the diets were found between the two groups. In summary, subjects with high P/B-ratio appeared more susceptible to lose body fat on diets high in fiber and wholegrain than subjects with a low P/B-ratio.

Introduction

The composition of the gut microbiota in rodents has been shown to affect the efficacy of energy harvest from feed (1) and to influence the secretion of gastrointestinal hormones affecting appetite (2). Therefore, it seems as if the human gut microbiota has the potential to play a pivotal role in personalized nutrition (3, 4).

Clustering of the human gut microbiota, designated enterotypes, was first described in 2011 (5). The *Bacteroides*-driven enterotype is reported to be predominant in individuals consuming more protein and animal fat (western diet), whereas the *Prevotella*-driven enterotype appears predominant in subjects consuming more carbohydrate and fiber (6-8). That said, the enterotype of an individual has been shown to remain rather stable (6, 7, 9). A limited number of studies have related microbial enterotypes to health markers (8-10); however, body fat change during a randomized clinical trial is not one of them.

Therefore, as a proxy for enterotypes, we studied pre-treatment *Prevotella/Bacteroides* (P/B) ratio as a prognostic marker for successful body fat loss on two diets differing greatly in dietary fiber and wholegrain content.

Methods

In total 181 participants with increased waist circumference were randomly assigned to receive an ad libitum New Nordic Diet (NND) or a control diet for 26 weeks of which a subgroup of 62 subjects were randomized to collect fecal samples. The macronutrient composition of the NND was based on Nordic Nutrition Recommendations, whereas the control diet was designed to match the macronutrient composition of an Average Danish Diet (ADD) (11) as seen in Table A below.

TABLE A

| Diet | NND (n = 91) | Control diet (n = 54) |
|---|---|---|
| Protein (Energy %) | 17.9 (17.2; 18.6) | 16.5 (15.7; 17.3) |
| Carbohydrate (Energy %) | 54.3 (52.7; 56.0)[6] | 50.8 (48.7; 52.1)[6] |
| Added sugar (Energy %) | 5.3 (4.0; 6.5) | 11.8 (10.3; 13.1) |
| Fibre (Energy %) | 3.5 (3.3; 3.7) | 2.3 (2.1; 2.4) |
| Total fat (Energy %) | 30.0 (28.7; 31.1) | 33.9 (32.8; 35.1) |
| SFA (Energy %) | 7.8 (7.0; 8.6) | 13.2 (12.6; 13.9) |
| MUFA (Energy %) | 12.0 (11.0; 12.5) | 12.6 (12.2; 13.7) |
| PUFA (Energy %) | 7.8 (6.7; 8.7) | 5.1 (4.7; 5.7) |
| Alcohol (Energy %) | 1.1 (0.5; 2.4) | 1.3 (0.5; 2.2) |
| Dietary fibre (g/10 MJ) | 44 (41; 46) | 28 (26; 30) |
| Wholegrain (g/10 MJ) | 157 (138; 175) | 43 (38; 51) |
| Fruit (g/10 MJ) | 408 (356; 447) | 190 (173; 215) |
| Berries (g/10 MJ) | 87 (74; 101) | 6 (4; 8) |
| Vegetable (g/10 MJ) | 755 (662; 845) | 239 (210; 262) |
| Potato (g/10 MJ) | 118 (104; 143) | 79 (54; 97) |

TABLE A-continued

| Diet | NND (n = 91) | Control diet (n = 54) |
|---|---|---|
| Milk products (g/10 MJ) | 338 (263; 429) | 379 (335; 468) |
| Meat and fish (g/10 MJ) | 199 (177; 219) | 181 (162; 204) |
| Nuts (g/10 MJ) | 35 (31; 39) | 8 (6; 10) |
| Salt (g/10 MJ) | 3.1 (2.8; 3.7) | 3.5 (2.9; 4.1) |
| Energy density (kJ/g) | 4.7 (4.5; 5.0) | 5.8 (5.3; 6.1) |

Abbreviations:
MUFA, Mono unsaturated fatty acids;
NND, New Nordic diet;
PUFA, Poly unsaturated fatty acids;
SFA, Saturated fatty acids;
FPG, Fasting plasma glucose.
Median (IQR) intake during the 26 week intervention period. Intake was calculated as foods collected in the shop subtracted by the foods not consumed plus consumption of foods from elsewhere.
[6] Available carbohydrates (not including fibre) were 47.1 (45.1; 48.7) and 45.8 (44.2; 47.2) Energy %, respectively.

The NND is a whole food approach characterized by being very high in dietary fiber, wholegrain, fruit, and vegetables (12). For both groups, food and beverages were provided from a study shop free of charge throughout the intervention period (12). Pre-intervention fasting blood samples were drawn from where fasting glucose and insulin were analyzed. Height was measured at baseline and body weight was measured at randomization and week 2, 4, 8, 12, 16, 20, 24, and 26. Furthermore, waist circumference and fat mass (using DEXA) were measured at randomization, week 12 and 26. Fecal samples were collected at baseline and the relative abundance of *Prevotella* spp. and *Bacteroides* spp. was determined using genera-specific quantitative PCR targeting the bacterial 16S ribosomal gene regions as previously described (9). As previously reported by Roager et al. (9), this resulted in a clear bi-modal separation of subjects based on the log *Prevotella* spp. to *Bacteroides* spp. ratio, in the following designated low P/B (<0.01) or high P/B (>0.01). In eight samples, *Prevotella* spp. was below the detection limit and were classified as low P/B in the main analysis and excluded in a sensitivity analysis. Regardless of randomization status, after the completion of the first 26 weeks all participants were instructed to follow the NND for an additional year (weight measured after 52 and 78 weeks) without any provision of food (13) to investigate the diets in a real life setting. The study was approved by the ethical committee of the Capital Region of Denmark (reference H-3-2010-058) and registered at clinicaltrials.gov as NCT01195610.

Statistics

Baseline characteristics were summarized as mean±standard deviation, median (interquartile range) or proportions (%) and differences between P/B groups as well as dietary groups were tested using a parametric (variables possibly transformed before analysis) or non-parametric two-sample test or Pearson's chi-squared test.

The differences in body fat (as well as weight and waist circumference) change from baseline between enterotypes on the two diets were analyzed by means of linear mixed models using all available measurements. The linear mixed models included the three-way interaction between diet×time×P/B group strata as well as all nested two-way interactions and main effects and comprised additional fixed effects including age, gender, baseline BMI, baseline fasting glucose and insulin as well as random effects for subjects. Results are shown as mean change from baseline with 95% confidence interval (CI). The level of significance was set at P<0.05 and statistical analyses were conducted using STATA/SE 14.1 (Houston, Texas USA).

Results

The NND compared to ADD was higher in dietary fibre (43.3 vs. 28.6 g/10 MJ), higher in protein (18.1 vs. 16.4%), lower in fat (30.4 vs. 33.8%) (all P<0.001) without differing in available carbohydrates (46.4 vs. 45.3%; P=0.081).

No differences in baseline characteristics were found between individuals characterized as high and low P/B (all P≥0.09) (Table 3). Among individuals with a high P/B ratio, the NND diet resulted in a 3.15 kg (95% CI 1.55;4.76, P<0.001) larger body fat loss compared to ADD after 26 weeks while no difference in body fat loss was observed between NND and ADD among individuals with low P/B (0.88 kg [95% CI −0.61;2.37, P=0.25]).

TABLE 3

Baseline characteristics of the study populations stratified by enterotype (n = 62)

| | High P/B group (n = 28) | Low P/B group (n = 34) | P-value |
|---|---|---|---|
| Age (year) | 41.9 (30.4; 56.7) | 47.5 (33.0; 55.6) | 0.33 |
| Gender (% female/male) | 64.3/35.7 | 69.2/30.8 | 0.70 |
| Body weight (kg) | 91.6 ± 17.6 | 84.8 ± 16.0 | 0.12 |
| Body mass index (kg/m$^2$) | 31.0 ± 4.7 | 29.0 ± 4.4 | 0.09 |
| Body fat (%) | 40.5 ± 6.4 | 38.9 ± 7.1 | 0.36 |
| Fasting glucose (mmol/L) | 5.34 ± 0.51 | 5.19 ± 0.40 | 0.20 |
| Fasting insulin (pmol/L) | 54.5 (41; 78) | 47.5 (35; 74) | 0.14 |
| *Prevotella* spp (relative abundance) | 0.016 (0.008; 0.063) | 0.00002 (0.000003; 0.00005) | <0.001[1] |
| *Bacteroides* (relative abundance) | 0.07 (0.05; 0.11) | 0.17 (0.10; 0.26) | <0.001[1] |
| *Prevotella*-to-*Bacteroides* ratio | 0.28 (0.11; 7.50) | 0.00007 (0.00001; 0.00026) | |

Abbreviation:
P/B, *Prevotella*-to-*Bacteroides* ratio.
Data are presented as mean ± standard deviation, median (interquartile range) or proportions (%) and differences between enterotypes were tested using a two-sample t-test (variables possibly transformed before analysis) or Pearson's chi-squared test.
[1] Using the non-parametric two-sample Wilcoxon rank-sum (Mann-Whitney) test.

Consequently, a 2.27 kg (95% CI 0.09;4.45, P=0.041) difference in responsiveness to the diets was found between the P/B groups which came from difference in response to NND (P=0.04) and not ADD (P=0.41) between the P/B groups (Table 4). Similar differences in responsiveness to the diets were found for waist circumference (3.95 cm [95% CI 0.34;7.55, P=0.032]) and were borderline significant for body weight (2.33 kg [95% CI −0.15;4.80, P=0.065]) (Table 4). The sensitivity analysis revealed larger differences (Table 4).

TABLE 4

Changes in body fat, body weight and waist circumference after 26 weeks on NND and ADD among high P/B and low P/B groups.

| All Subjects | High P/B group | | Low P/B group | | $P^1$ | $P^2$ | $P^3$ | $P^4$ | Δ(NND-ADD) in high P/B − Δ(NND-ADD) in low P/B | $P^5$ |
|---|---|---|---|---|---|---|---|---|---|---|
| | NND (n = 15) | ADD (n = 13) | NND (n = 21) | ADD (n = 13) | | | | | | |
| ΔBody fat (kg) | −4.97 (−6.06; −3.88) | −1.82 (−3.01; −0.63) | −3.41 (−4.35; −2.48) | −2.53 (−3.69; −1.37) | <0.001 | 0.25 | 0.04 | 0.41 | −2.27 (−4.45; −0.09) | 0.041 |
| ΔWeight (kg) | −4.58 (−5.82; −3.34) | −1.09 (−2.43; 0.25) | −3.27 (−4.33; −2.22) | −2.11 (−3.43; −0.79) | <0.001 | 0.18 | 0.12 | 0.29 | −2.33 (−4.80; 0.15) | 0.065 |
| ΔWC (cm) | −5.19 (−6.99; −3.38) | −0.44 (−2.41; 1.52) | −3.09 (−4.64; −1.55) | −2.29 (−4.22; −0.37) | <0.001 | 0.53 | 0.09 | 0.19 | −3.95 (−7.55; −0.34) | 0.032 |
| Sensitivity[6] | NND (n = 15) | ADD (n = 13) | NND (n = 16) | ADD (n = 10) | $P^1$ | $P^2$ | $P^3$ | $P^4$ | | $P^5$ |
| ΔBody fat (kg) | −4.96 (−5.95; −3.97) | −1.79 (−2.87; −0.71) | −2.94 (−3.93; −1.94) | −2.71 (−3.92; −1.50) | <0.001 | 0.78 | 0.01 | 0.27 | −2.94 (−5.05; −0.85) | 0.006 |
| ΔWeight (kg) | −4.57 (−5.70; −3.45) | −1.07 (−2.29; 0.15) | −2.52 (−3.64; −1.40) | −2.56 (−3.93; −1.18) | <0.001 | 0.97 | 0.01 | 0.12 | −3.53 (−5.92; −1.15) | 0.004 |
| ΔWC (cm) | −5.14 (−6.91; −3.36) | −0.54 (−2.47; 1.39) | −2.29 (−4.07; −0.52) | −3.60 (−5.76; −1.43) | <0.001 | 0.36 | 0.03 | 0.04 | −5.90 (−9.65; −2.14) | 0.002 |

Abbreviations: ADD, Average Danish Diet; New Nordic Diet; P/B, *Prevotella*-to-*Bacteroides* ratio; WC, Waist circumference. Data are presented as estimated mean body fat, body weight and waist circumference change from baseline and 95% confidence intervals for each combination of the diet-enterotype strata interaction after 26 weeks in the linear mixed models, which were additionally adjusted for age, gender, baseline BMI, fasting glucose and insulin as well as random effects for subjects.
[1]P-value representing the difference in dietary response within the high P/B group.
[2]P-value representing the difference in dietary response within the low P/B group.
[3]P-value representing the difference in response to NND between the P/B groups.
[4]P-value representing the difference in response to ADD between the P/B groups.
[5]P-value representing the following pairwise comparison using post hoc t-tests: Δ(NND-ADD) among subjects with high P/B minus Δ(NND-ADD) among subjects with low P/B.
[6]Sensitivity analyses excluding the eight subjects with *Prevotella* spp. below the detection limit.

During the one-year follow-up period, subjects with the high P/B ratio changing from ADD to being recommended NND maintained their weight [−1.23 (95% CI −2.81;0.36, n=9, P=0.13)], whereas subjects with the low P/B ratio changing from ADD to being recommended NND regained 2.76 kg (95% CI 1.27;4.24, n=11, P<0.001). Consequently, a 3.99 kg (95% CI, 1.82;6.15, P<0.001) difference in responsiveness to the NND were found between P/B groups during the one year follow-up. This difference was 5.41 kg (95% CI 3.12;7.69, P<0.001) in the sensitivity analysis.

Discussion

We identified pre-treatment P/B ratio as an important biomarker associated with body fat loss in subjects consuming an ad libitum diet rich in fiber and wholegrain. Thus, overweight and obese participants with high P/B ratio appeared more responsive to fiber and wholegrain than individuals with low P/B ratio. This was further supported by similar findings for waist circumference and body weight.

Using the entire sample of 181 subjects, we have previously reported the overall weight loss difference between the NND and ADD to be 3.2 kg (12). Interestingly, this difference between diets could mainly be attributed to subjects with the high P/B ratio, and the health promoting aspects of the NND in terms of body weight regulation therefore mainly seems to apply in a subset of the population.

Previously, baseline total cholesterol has been found to be borderline higher (P=0.08) (9) and LDL cholesterol to be lower (8) among the *Prevotella*-driven enterotype. Furthermore, the enterotypes have been found to impact in vitro fermentation profiles of short chain fatty acids from the same carbohydrate substrates differentially, with the *Prevotella*-driven enterotype having higher total short chain fatty acid production (3). In vitro, some of these short chain fatty acids have been shown to stimulate the secretions of gastrointestinal hormones affecting appetite (2). Finally, in an observational study of 1632 women, the abundance of *Bacteroides* spp. was associated with weight gain, while dietary fiber intake was found partly to modify the association between microbiome diversity and weight gain (14).

The distinction of enterotypes as discrete clusters has recently been challenged by studies suggesting that enterotype distribution is continuous and that further information may be masked within these enterotype clusters (15, 16). From our analysis we cannot determine specific bacterial species responsible for the dietary effects that we observe but only highlight the relative abundance of *Prevotella* spp. (genus) as important in the classification of microbiota profiles. Nevertheless, our sensitivity analysis indicates that subjects with *Prevotella* spp. below the detection limit behave different than subjects in the low P/B ratio group.

The increased responsiveness of the high P/B group to the NND, rich in fruits, vegetables and whole grains, is supported by previous studies showing an association between the *Prevotella*-driven enterotype and a carbohydrate-based diet more typical of agrarian societies (6). However, only two individuals switched P/B ratio group during this 6 month dietary intervention with NND or ADD (9), which is consistent with the literature indicating that intestinal microbial communities are resilient and difficult to change through dietary interventions (6, 7, 9) unless extreme changes, such as complete removal of carbohydrates from the diet, are introduced (17).

Mechanisms involved could be efficacy of energy harvest from different foods (1), differences in fibre-utilization capacity (3), gut-brain signalling of behaviour (18), and the secretion of gastrointestinal hormones affecting appetite (2, 10). Recently, dietary fiber-induced improvements in postprandial blood glucose and insulin were found to be positively associated with the abundance of *Prevotella* (19). Therefore, the recent breakthrough in personalized nutrition, showing the importance of pre-treatment fasting glucose and insulin to determine the optimal diet for weight management (20), might also be linked to gut microbiota profiles. We therefore adjusted for a number of potential confounders including fasting glucose and insulin. However, independent of the mechanisms, the P/B ratio may serve as a biomarker to predict future weight loss success on specific diets.

In summary, we identified pre-treatment P/B ratio as an important biomarker associated with dietary body fat change on ad libitum high fiber diets. Thus, individuals with a high P/B ratio were more susceptible to body fat loss on a diet rich in fiber and whole grain compared to an average Danish diet, whereas no difference in body fat loss was observed in individuals with a low P/B ratio.

REFERENCES

1. Turnbaugh P J, Ley R E, Mahowald M A, Magrini V, Mardis E R, Gordon J I. An obesity-associated gut microbiome with increased capacity for energy harvest. Nature. 2006; 444(7122):1027-131.
2. Tolhurst G, Heffron H, Lam Y S, Parker H E, Habib A M, Diakogiannaki E, et al. Short-chain fatty acids stimulate glucagon-like peptide-1 secretion via the G-protein-coupled receptor FFAR2. Diabetes. 2012 February; 61(2): 364-71.
3. Chen T, Long W, Zhang C, Liu S, Zhao L, Hamaker B R. Fiber-utilizing capacity varies in *Prevotella-* versus *Bacteroides*-dominated gut microbiota. Sci Rep. 2017 Jun. 1; 7(1):2594,017-02995-4.
4. Zeevi D, Korem T, Zmora N, Israeli D, Rothschild D, Weinberger A, et al. Personalized nutrition by prediction of glycemic responses. Cell. 2015; 163(5):1079-94.
5. Arumugam M, Raes J, Pelletier E, Le Paslier D, Yamada T, Mende D R, et al. Enterotypes of the human gut microbiome. Nature. 2011; 473(7346):174-80.
6. Wu G D, Chen J, Hoffmann C, Bittinger K, Chen Y Y, Keilbaugh S A, et al. Linking long-term dietary patterns with gut microbial enterotypes. Science. 2011 Oct. 7; 334(6052):105-8.
7. Lim M Y, Rho M, Song Y, Lee K, Sung J, Ko G. Stability of gut enterotypes in Korean monozygotic twins and their association with biomarkers and diet. Scientific reports. 2014; 4:7348.
8. de Moraes A C, Fernandes G R, da Silva I T, Almeida-Pititto B, Gomes E P, da Costa Pereira A, et al. Enterotype may drive the dietary-associated cardiometabolic risk factors. Frontiers in Cellular and Infection Microbiology. 2017; 7.
9. Roager H M, Licht T R, Poulsen S K, Larsen T M, Bahl M I. Microbial enterotypes, inferred by the *prevotella*-to-*bacteroides* ratio, remained stable during a 6-month randomized controlled diet intervention with the new nordic diet. Appl Environ Microbiol. 2014 February; 80(3):1142-9.
10. Kang C, Zhang Y, Zhu X, Liu K, Wang X, Chen M, et al. Healthy subjects differentially respond to dietary capsaicin correlating with specific gut enterotypes. The Journal of Clinical Endocrinology & Metabolism. 2016;101(12):4681-9.
11. Pedersen A N, Fagt S, Groth M V, Christensen T, Biltoft-Jensen A P, Matthiessen J, et al. Danskernes kostvaner 2003-2008: hovedresultater. DTU Fødevareinstituttet; 2010.
12. Poulsen S K, Due A, Jordy A B, Kiens B, Stark K D, Stender S, et al. Health effect of the New Nordic Diet in adults with increased waist circumference: a 6-mo randomized controlled trial. Am J Clin Nutr. 2014 January; 99(1):35-45.
13. Poulsen S K, Crone C, Astrup A, Larsen T M. Long-term adherence to the New Nordic Diet and the effects on body weight, anthropometry and blood pressure: a 12-month follow-up study. Eur J Nutr. 2015; 54(1):67-76.
14. Menni C, Jackson M, Pallister T, Steves C, Spector T, Valdes A. Gut microbiome diversity and high-fibre intake are related to lower long-term weight gain. Int J Obes. 2017.
15. Knights D, Ward T L, McKinlay C E, Miller H, Gonzalez A, McDonald D, et al. Rethinking "enterotypes". Cell host & microbe. 2014; 16(4):433-7.
16. Gorvitovskaia A, Holmes S P, Huse S M. Interpreting *Prevotella* and *Bacteroides* as biomarkers of diet and lifestyle. Microbiome. 2016; 4(1):15.
17. Andrés M, Ana D, Juan José A, Amparo L. Effect of dietary carbohydrate restriction on an obesity-related *Prevotella*-dominated human faecal microbiota. Metagenomics. 2013; 2013.
18. Mayer E A, Tillisch K, Gupta A. Gut/brain axis and the microbiota. J Clin Invest. 2015; 125(3):926-38.
19. Kovatcheva-Datchary P, Nilsson A, Akrami R, Lee Y S, De Vadder F, Arora T, et al. Dietary fiber-induced improvement in glucose metabolism is associated with increased abundance of *Prevotella*. Cell metabolism. 2015; 22(6):971-82.
20. Hjorth M F, Ritz C, Blaak E E, Saris W H M, Langin D, Poulsen S K, et al. Pre-treatment fasting plasma glucose and insulin modify dietary weight loss success: results from three randomized clinical trials. Am Clin Nutr. 2017 (DOI: 10.3945/ajcn.117.155200).

Example 2: Exploration of Associations Between Gut Microbiota and Weight Loss on Two Different Diets Using the data and information from Example 1, several options were considered for predicting responsiveness in weight change (in Kg) to the New Nordic Diet (NND) and Average Danish Diet (ADD). These different options exclusively use the bacteria found in Table 3. In total, we had 62 samples where *Bacteroidetes* all and *Bacteroides* spp. were detected in all of them and *Prevotella* spp. was detected in 54 of the samples. Therefore, some of the below options only include 54 out of the 62 participants. You will be able to find additional information about how the 62 samples were analyses using 16S and qPCR as well as information about the categorization of enterotypes in Roager et al. Appl Environ Microbiol. 2014 February; 80(3):1142-9 (including supplementary material).

In addition to considering weight loss based on enterotype, also considered were other ways to express single bacteria's or ratios of bacteria's essentially to describe the same phenomenon. This ended up with several combinations of the three bacteria's in Table 5.

TABLE 5

Taxonomy of the microbial bacteria used in the following either alone or as ratios.

| Phylum | Genus | Species |
| --- | --- | --- |
| Bacteroidetes | Bacteroidetes | All |
| Bacteroidetes | *Bacteroides* | spp. |

TABLE 5-continued

Taxonomy of the microbial bacteria used in the following either alone or as ratios.

| Phylum | Genus | Species |
| --- | --- | --- |
| Bacteroidetes | *Prevotella* | spp. |

Option 1

Figure 3:
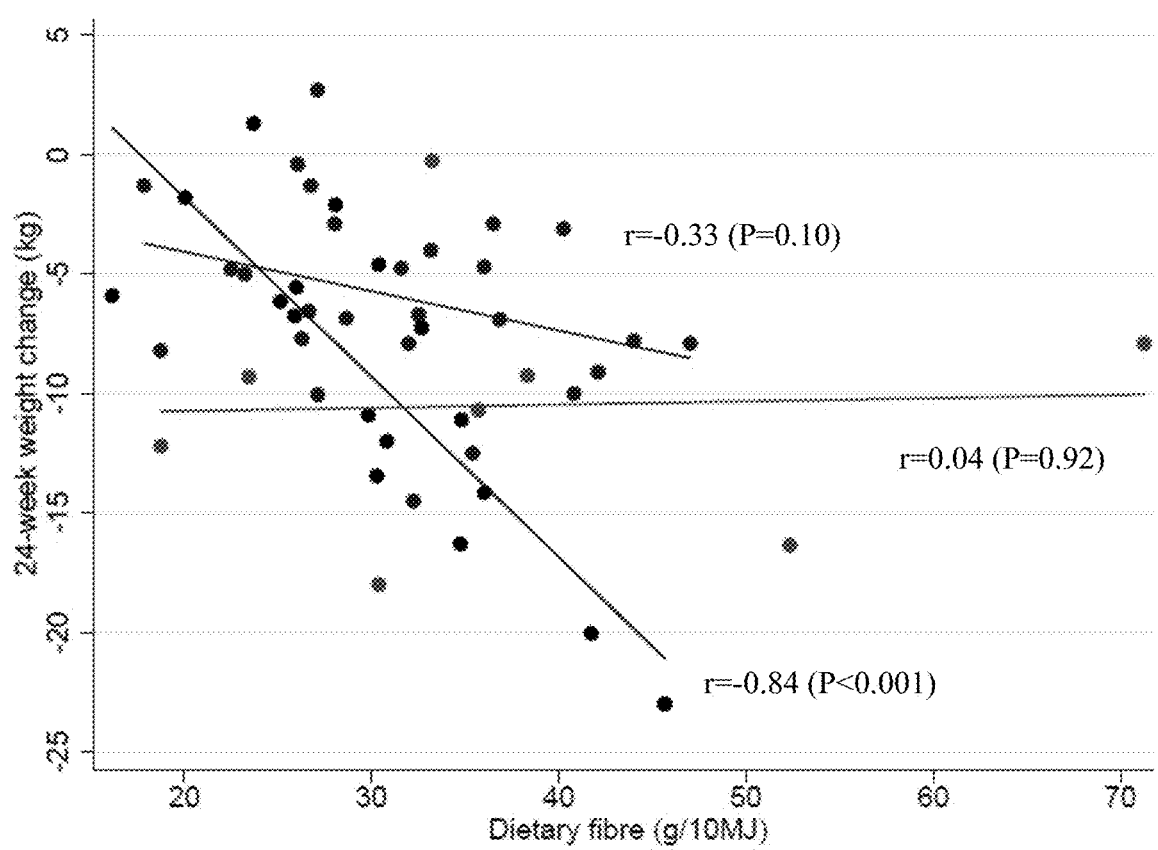
FIG. 3 is a scatter plot between dietary fiber and 24-week weight loss stratified by three *Prevotella/Bacteroides* groups. Blue: Low P/B-ratio (n=26); Black: High P/B-ratio (n=17); Red: 0-*prevotella* (n–8). Pearson's correlation coefficients are presented on the figure.
Figure 4:
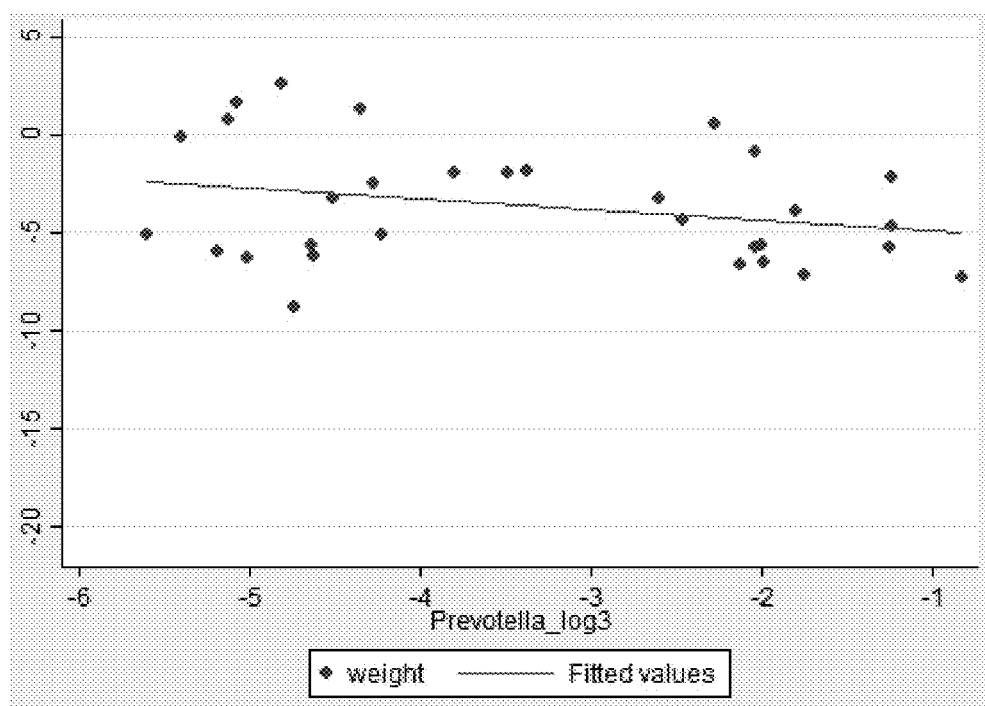
FIG. 4 is line graph showing the correlation between the relative abundance of log 10(*Prevotella* spp.) and weight loss of patients on the NND (r=−0.28, p=0.12).
Figure 5:
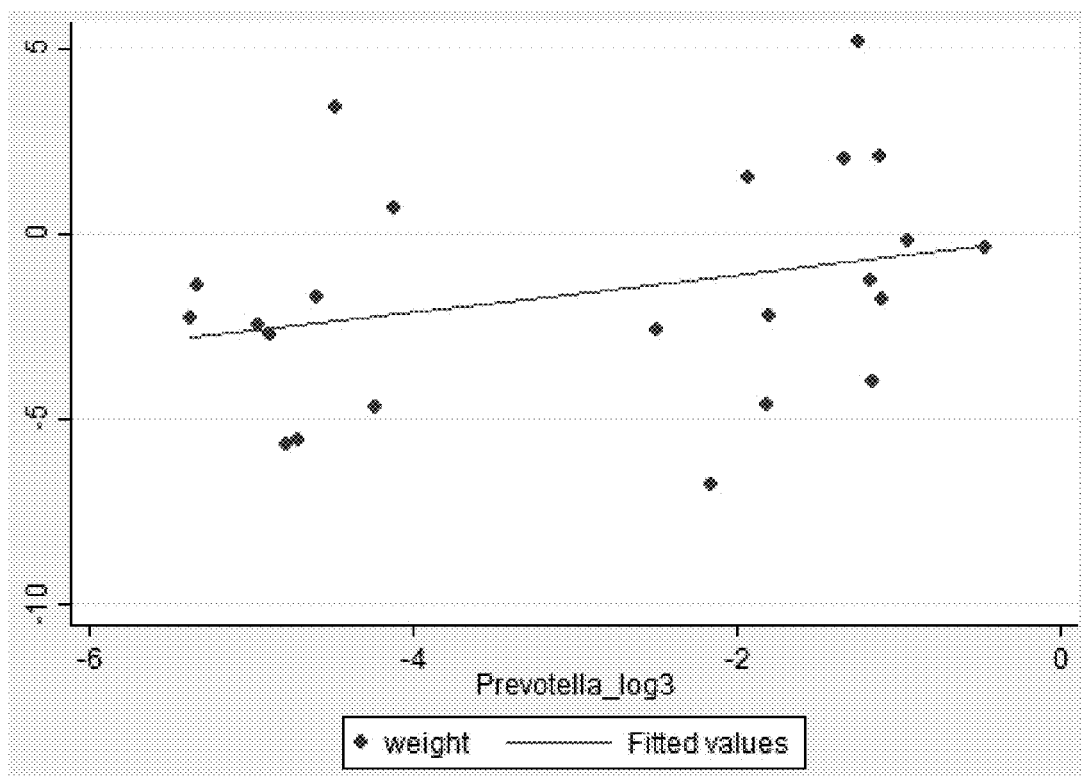
FIG. 5 is a line graph showing the correlation between the relative abundance of log 10(*Prevotella* spp.) and weight loss of patients on the ADD (r=0.29, p=0.18).

The abundance of_log 10(*Prevotella* spp.) is characterized by two distinct groups using a cutoff of −3 (FIGS. 3, 4, and 5).

A. Log 10(*Prevotella* spp)>−3 & ADD: −1.07 (−2.31; 0.17), P=0.089 (n=13)
    B. Log 10(*Prevotella* spp)>−3 & NND: −4.49 ('5.68;−3.30), P<0.001 (n=14)
    C. Log 10(*Prevotella* spp)<−3 & ADD: −2.54 (−3.93;−1.15), P<0.001 (n=10)
    D. Log 10(*Prevotella* spp)<−3 & NND: −2.72 (−3.83;−1.61), P<0.001 (n=17)
    A vs. B: −3.41 (−5.11;−1.72), P<0.001
    C vs. D: −0.18 (−1.95;1.59), P=0.84
    AB vs. CD: −3.24 (−5.66;−0.82), P=0.009

Option 1a

Option 1a is the same as Option 1 but with the 8 subjects where no *Prevotella* spp. was detected being classified as having Log 10(*Prevotella* spp.)<−3. See Figures A. Log 10(*Prevotella* spp)>−3 & ADD: −1.09 (−2.44; 0.26), P=0.11 (n=13)
    B. Log 10(*Prevotella* spp)>−3 & NND: −4.50 (−5.80;−3.20), P<0.001 (n=14)
    C. Log 10(*Prevotella* spp)<−3 & ADD: −2.11 (−3.44;−0.78), P=0.002 (n=13)
    D. Log 10(*Prevotella* spp)<−3 & NND: −3.39 (−4.43;−2.34), P<0.001 (n=22)
    A vs. B: −3.41 (−5.26;−1.55), P<0.001
    C vs. D: −1.28 (−2.96;0.40), P=0.14
    AB vs. CD: −2.13 (−4.63;0.38), P=0.096

It appears from this calculation that the 8 individuals who have no detectaable *Prevotella* spp. behave as if they do not have a low relative abundance of *Prevotella* spp.

Option 1b:

Option 1b is the same as option 1 but with the 8 subjects where no *Prevotella* spp. was detected being classified as having Log 10(*Prevotella* spp)>−3.

A. Log 10(*Prevotella* spp)>−3 & ADD: −1.09 (−2.27; 0.09), P=0.070 (n=16)
    B. Log 10(*Prevotella* spp)>−3 & NND: −4.80 (−5.89;−3.72), P<0.001 (n=19)
    C. Log 10(*Prevotella* spp)<−3 & ADD: −2.48 (−3.97;−1.00), P=0.001 (n=10)
    D. Log 10(*Prevotella* spp)<−3 & NND: −2.67 (−3.86;−1.48), P<0.001 (n=17)
    A vs. B: −3.71 (−5.29;−2.13), P<0.001
    C vs. D: −0.19 (−2.07;1.70), P=0.85
    AB vs. CD: −3.52 (−5.98;−1.07), P=0.005

It appears from this calculation that the 8 subjects not having any *Prevotella* spp. behave as if they have a high relative abundance of *Prevotella* spp, as these subjects benefit from the NND diet in the same way as people with high amount of *Prevotella* spp.

Option 2

Figure 6:
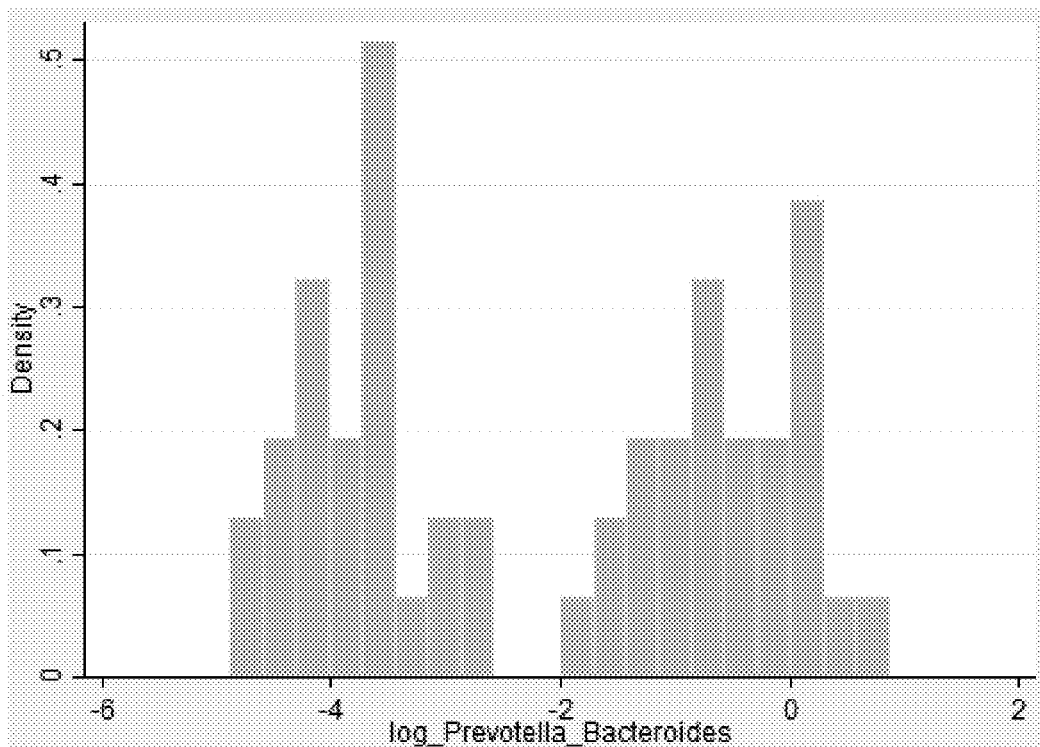
FIG. 6 is a bar graph showing the relative abundance of log 10(*Prevotella* spp./*Bacteroides* spp.) using a cutoff of −2.
Figure 7:
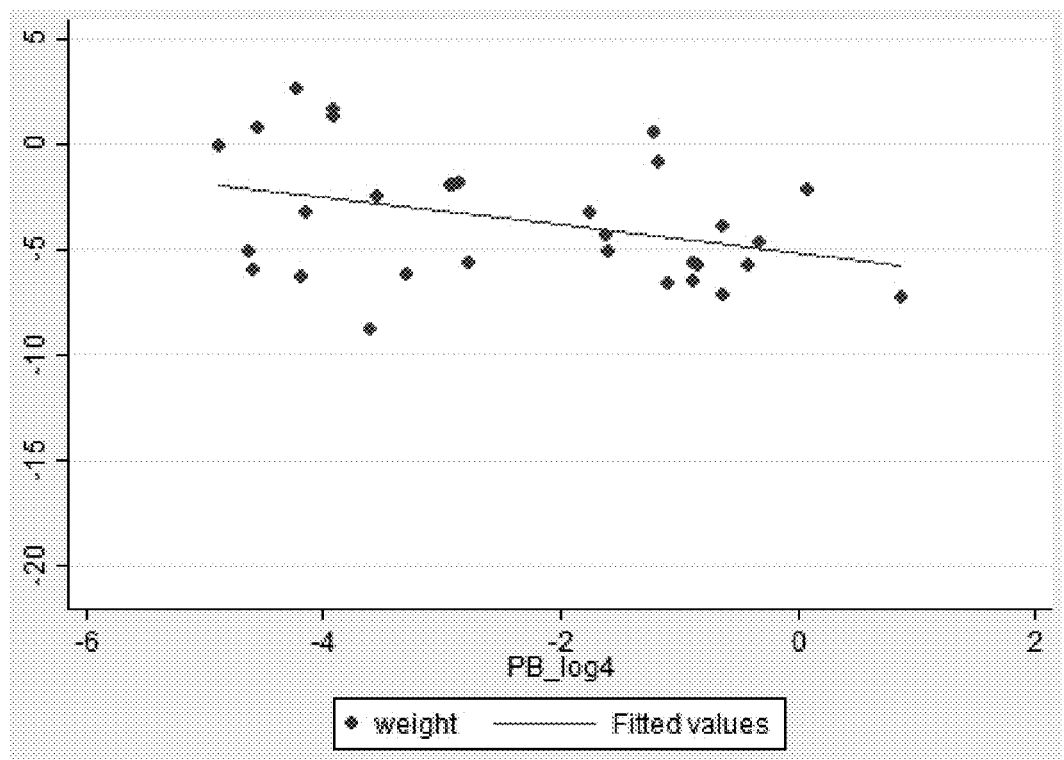
FIG. 7 is line graph showing the correlation between the relative abundance of log 10(*Prevotella* spp./*Bacteroides* spp.) and weight loss of patients on the NND (r=−0.37, p=0.04).
Figure 8:
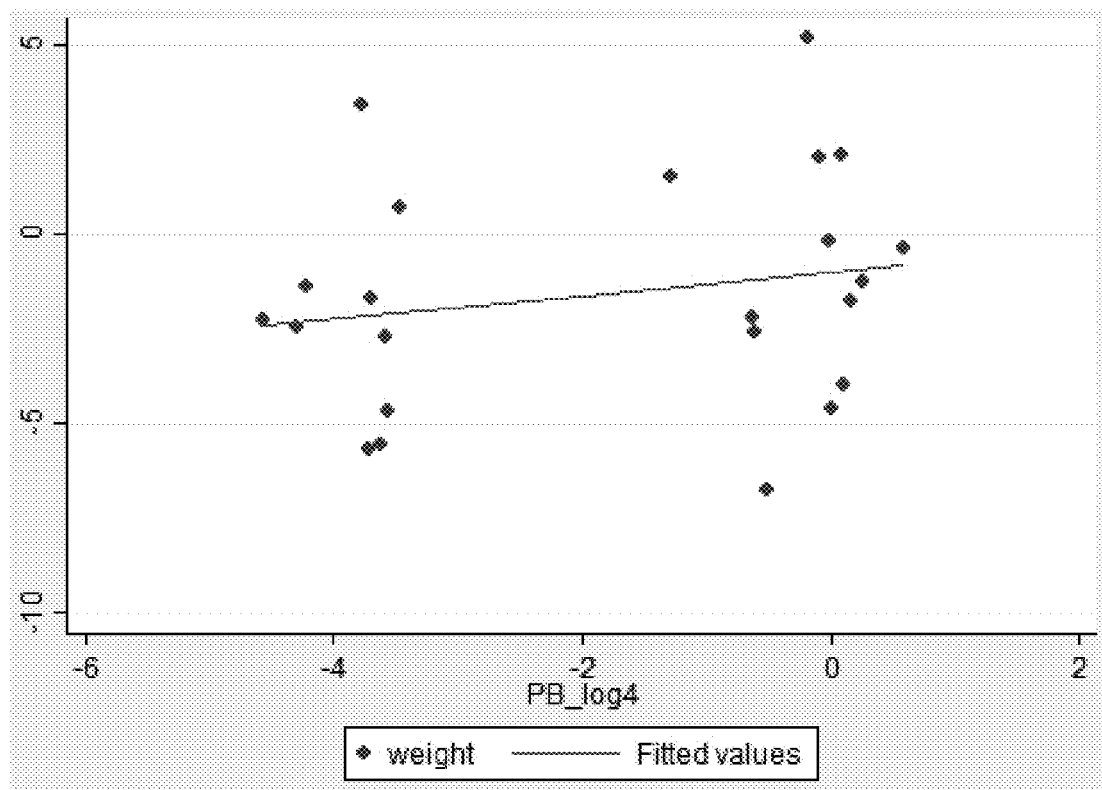
FIG. 8 is line graph showing the correlation between the relative abundance of log 10(*Prevotella* spp./*Bacteroides* spp.) and weight loss of patients on the ADD (r=0.20, P=0.37).
Figure 9:
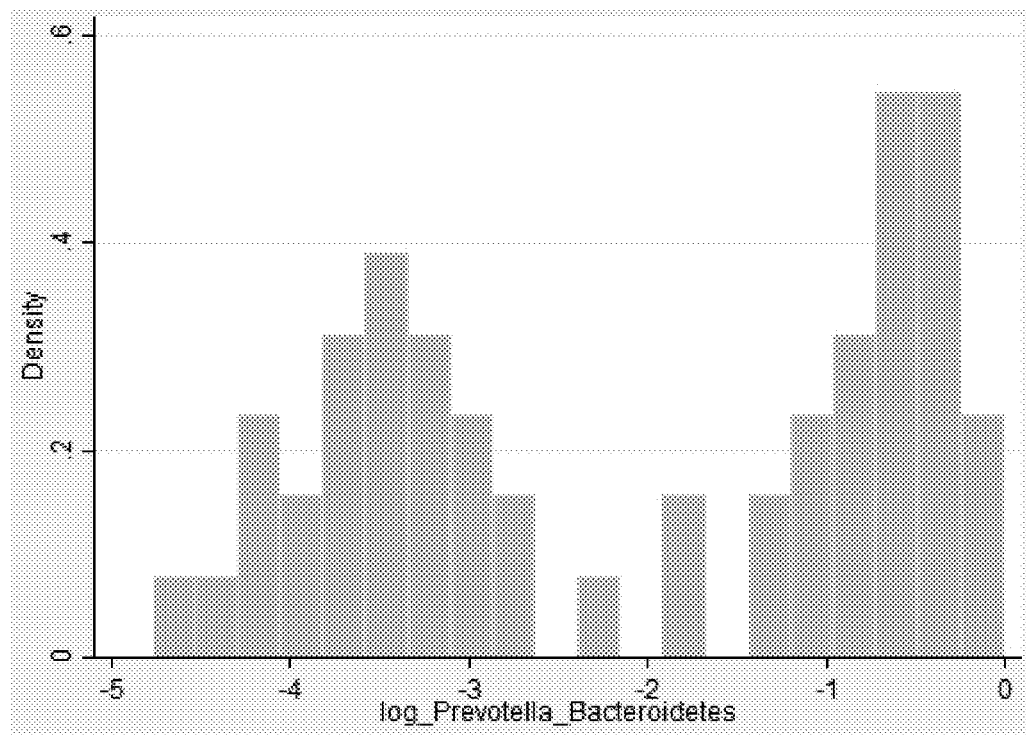
FIG. 9 is a bar graph showing the relative abundance of log 10(*Prevotella* spp./*Bacteroidetes* all) using a cutoff of −2.
Figure 10:
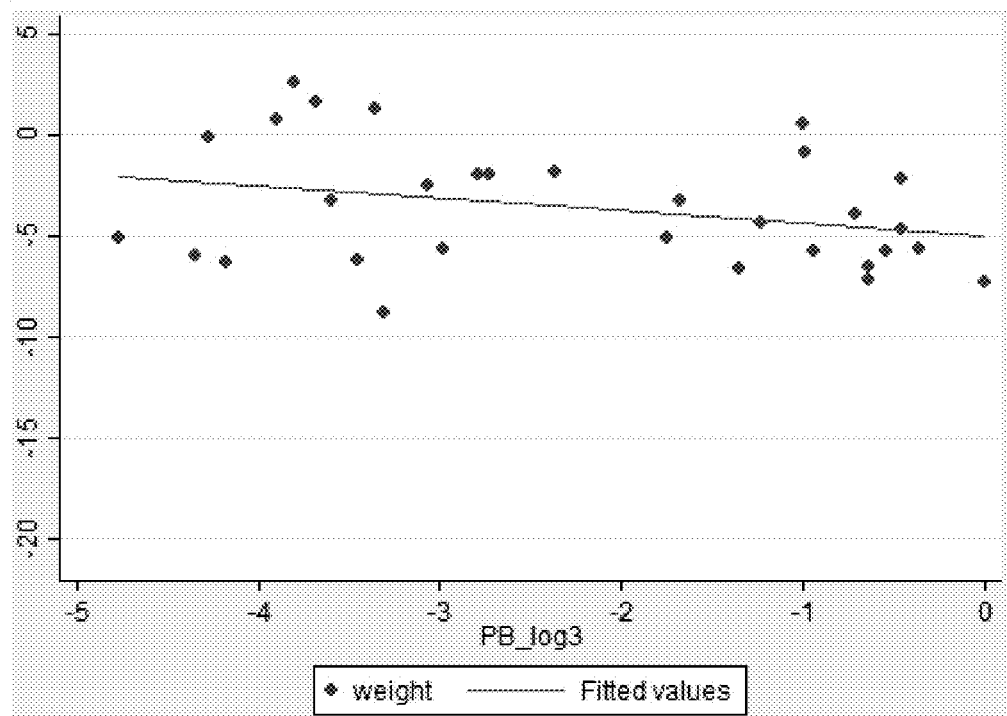
FIG. 10 is line graph showing the correlation between the relative abundance of log 10(*Prevotella* spp./*Bacteroidetes* all) and weight loss of patients on the NND (r=−0.30, P=0.099).
Figure 11:
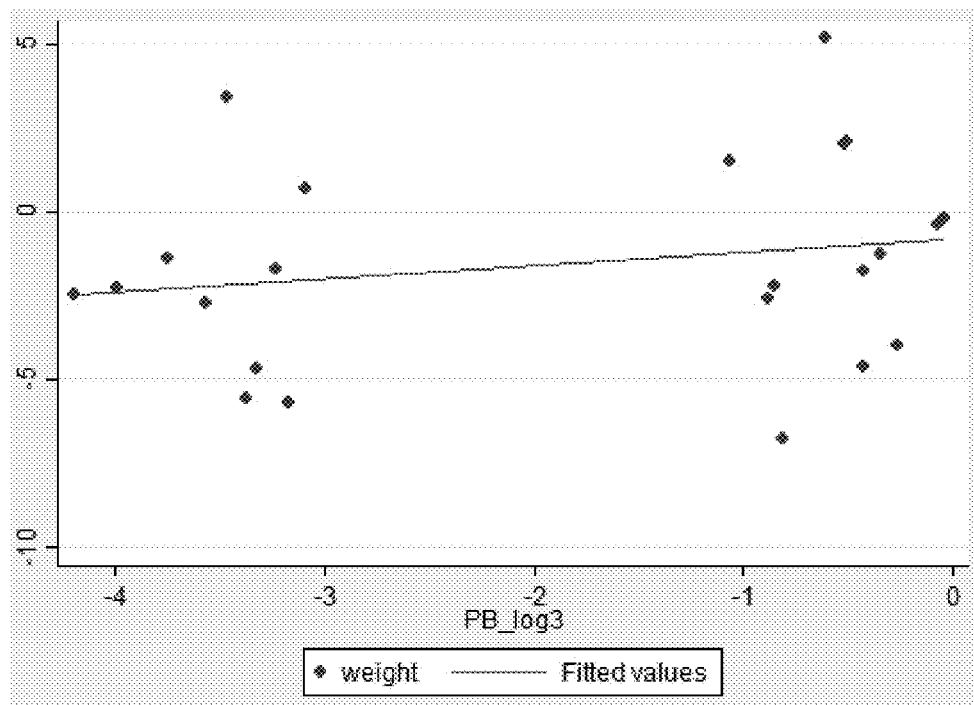
FIG. 11 is line graph showing the correlation between the relative abundance of log 10(*Prevotella* spp./*Bacteroidetes* all) and weight loss of patients on the ADD (r=0.20, P=0.36).

The abundance of Log 10(*Prevotella* spp/*Bacteroides* spp) is characterized by two distinct groups using a cutoff of −2 (FIGS. 6, 7 and 8.)

A. Log 10(*Prevotella* spp/*Bacteroides* spp)>−2 & ADD: −1.07 (−2-29;0.15), P=0.085 (n=13)
    B. Log 10(*Prevotella* spp/*Bacteroides* spp)>−2 & NND: −4.57 (−5.70;−3.45), P<0.001 (n=15)
    C. Log 10(*Prevotella* spp/*Bacteroides* spp)<−2 & ADD: −2.56 (−3.93;−1.18), P<0.001 (n=10)
    D. Log 10(*Prevotella* spp/*Bacteroides* spp)<−2 & NND: −2.52 (−3.64;−1.40), P<0.001 (n=16)
    A vs. B: −3.50 (−5.14;−1.85), P<0.001
    C vs. D: 0.03 (−1.73; 1.80), P=0.97
    AB vs CD: −3.53 (−5.92;−1.14), P=0.004

Option 2a

Option 2a is the same as Option 2 but with the 8 subjects where no *Prevotella* spp. was detected being classified as having Log 10(*Prevotella* spp/*Bacteroides* spp)<−2

A. Log 10(*Prevotella* spp/*Bacteroides* spp)>−2 & ADD: −1.09 (−2.43;0.25), P=0.11 (n=13)
    B. Log 10(*Prevotella* spp/*Bacteroides* spp)>−2 & NND: −4.58 (−5.82;−3.34), P<0.001 (n=15)
    C. Log 10(*Prevotella* spp/*Bacteroides* spp)<−2 & ADD: −2.11 (−3.43;−0.79), P=0.002 (n=13)
    D. Log 10(*Prevotella* spp/*Bacteroides* spp)<−2 & NND: −3.27 (−4.33;−2.22), P<0.001 (n=21)
    A vs. B: −3.49 (−5.31;−1.67), P<0.001
    C vs. D: −1.16 (−2.85; 0.53), P=0.18
    AB vs CD: −2.33 (−4.80;0.15), P=0.065

Option 2b

Option 2b is the same as Option 2 but with the 8 subjects where no *Prevotella* spp. was detected being classified as having Log 10(*Prevotella* spp/*Bacteroides* spp)>−2

A. Log 10(*Prevotella* spp/*Bacteroides* spp.)>−2 & ADD: −1.08 (−2.25;0.08), P=0.069 (n=16)
    B. Log 10(*Prevotella* spp/*Bacteroides* spp.)>−2 & NND: −4.84 (−5.88;−3.80), P<0.001 (n=20)
    C. Log 10(*Prevotella* spp/*Bacteroides* spp.)<−2 & ADD: −2.50 (−3.98;−1.03), P=0.001 (n=10)
    D. Log 10(*Prevotella* spp/*Bacteroides* spp.)<−2 & NND: −2.49 (−3.69;−1.29), P<0.001 (n=16)
    A vs. B: −3.76 (−5.30;−2.21), P<0.001
    C vs. D: 0.01 (−1.88; 1.90), P=0.99
    AB vs CD: −3.77 (−6.21;−1.33), P=0.002

Option 3:

Log 10(*Prevotella* spp./*Bacteroidetes* all) using −2 as cutoff will divide the population in the exact same way as Option 2 and the results is therefore the same.

Figure 12:
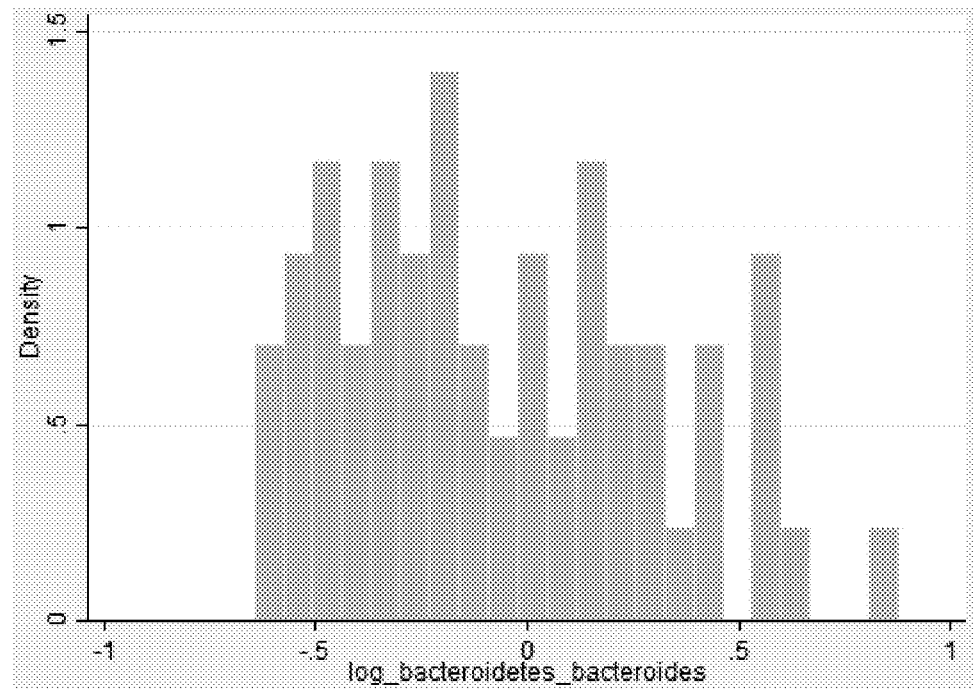
FIG. 12 is a bar graph showing the relative abundance of log 10(*Bacteroidetes* all/*Bacteroides* spp.) using a cut off of 0.
Figure 13:
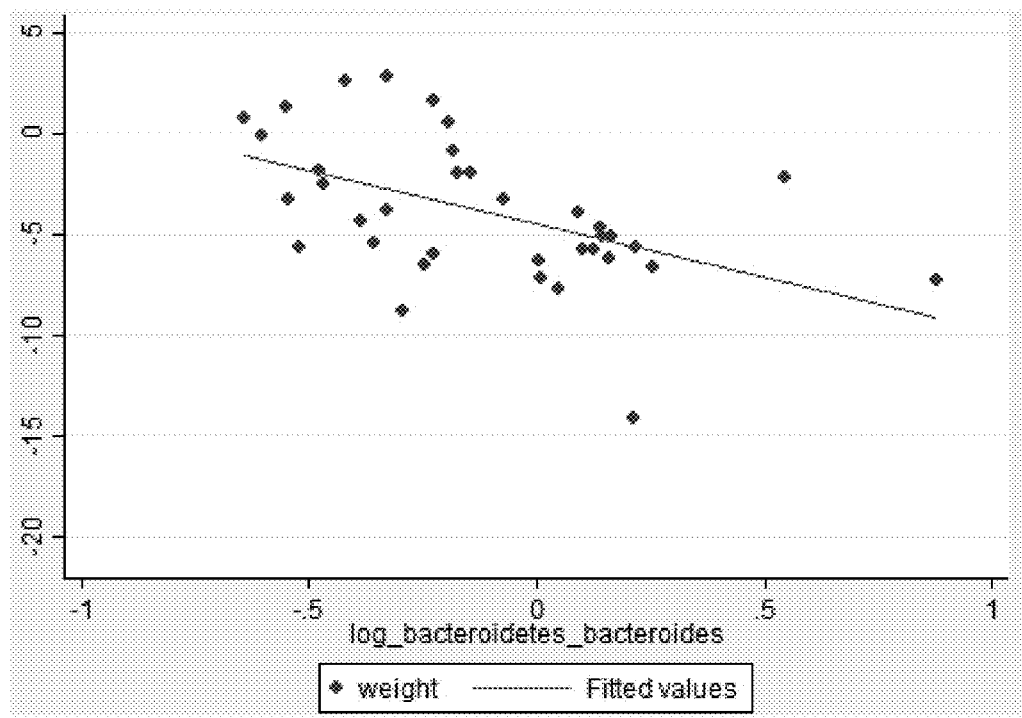
FIG. 13 is a line graph showing the correlation between the relative abundance of log 10(*Bacteroidetes* all/*Bacteroides* spp.) and weight loss of patients on NND NND (r=−0.50, P=0.002).
Figure 14:
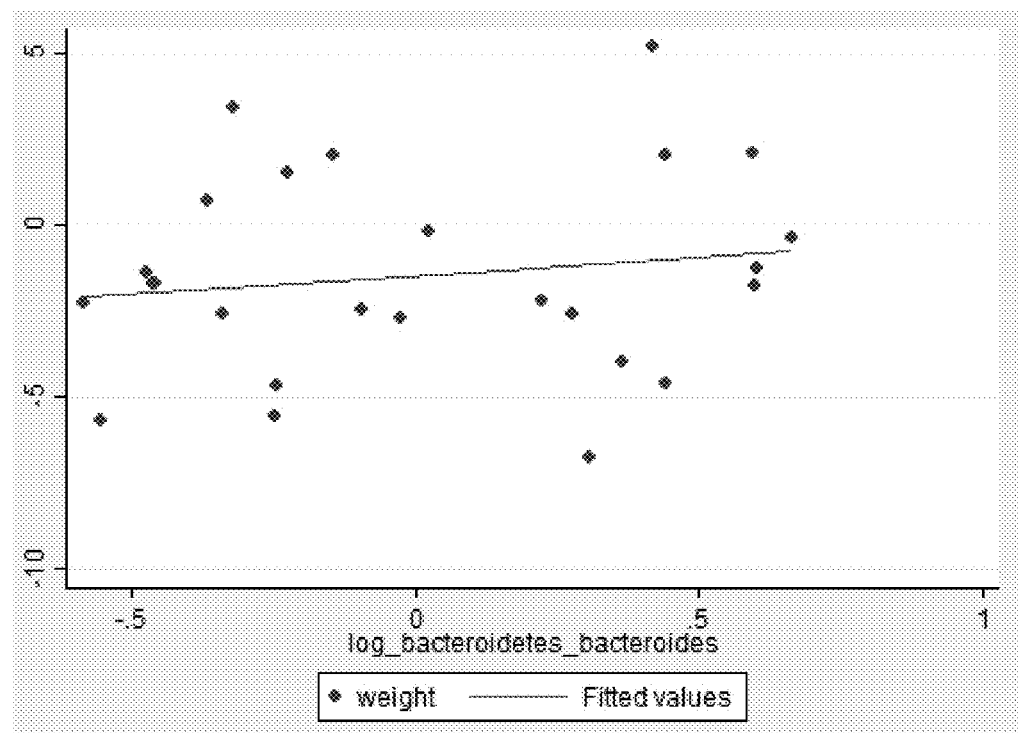
FIG. 14 is the line graph showing the correlation between the relative abundance of log 10(*Bacteroidetes* all/*Bacteroides* spp.) and weight loss of patients on ADD (r=0.15, P=0.48).

Option 4:

The relative abundance of log 10(*Bacteroidetes* all/*Bacteroides* spp.) is not characterized by two distinct groups but cutoff 0 has been used. These results include all 62 subjects as this ratio did not include *Prevotella* spp. (FIGS. 12, 13, and 14).

A. Log 10(*Bacteroidetes* all/*Bacteroides* spp.)<0 and NND: −2.23 (−3.20;−1.27) kg (P<0.001) (n=21)
    B. Log 10(*Bacteroidetes* all/*Bacteroides* spp.)<0 and ADD: −1.81 (−2.98;−0.63) kg (P=0.003) (n=14)
    C. Log 10(*Bacteroidetes* all/*Bacteroides* spp.)>0 and NND: −6.05 (−7.18;−4.91) kg (P<0.001) (n=15)
    D. Log 10(*Bacteroidetes* all/*Bacteroides* spp.)>0 and ADD: −1.33 (−2.63;−0.03) kg (P=0.044) (n=12)
    A vs. B: −0.43 (−1.93;1.08), P=0.58
    C vs. D: −4.72 (−6.44;−3.00), P<0.0.01
    AB vs CD: −4.29 (−6.57;−2.02), P<0.001

Correlation between Log 10(*Bacteroidetes* all/*Bacteroides* spp) and *Prevotella* spp. (r=0.70, P<0.001, n=54).

Example 3: Pre-Treatment Fasting Plasma Glucose Modifies Dietary Weight Loss Maintenance Success: Results from a Stratified RCT The purpose of this study was to investigate fasting plasma glucose (FPG) and fasting insulin (FI) as prognostic markers for weight loss maintenance when allocated to three different diets varying in macronutrient composition and fibre content.

Methods

A total of 125 participants in the MUFOBES study fulfilled the inclusion criteria and qualified for the 26-week weight loss maintenance period as they lost >8% of their initial body weight during the initial 8-week low-calorie diet. In this parallel-group block (gender and initial BMI) randomized trial participants were assigned to one of three ad libitum diets: 1) The new Healthy Eating Pyramid being moderate in fat (35-45E %), high in mono-unsaturated fatty acids (>20E %), high in fiber (>30 g/10 MJ), and high in energy density [MUFA; n=52], 2) the official Nordic Dietary Guidelines (similar to the USDA Food Pyramid) being low in fat (20-30E %), high in fiber (>30 g/10 MJ), and low in energy density [NNR; n=48] or 3) the average Danish diet (similar to the Western diet) being high in saturated fatty acids (>15E %), lower in fiber (<30 g/10 MJ), and high in energy density [ADD; n=25]. Alcohol (<5 E %) and protein (10-20 E %) were kept constant between the three diets.

The study participants collected all foods free of charge from a supermarket established at the department during the 6-month dietary intervention. At each shopping session barcodes were scanned to ensure that the foods meet the prescribed macronutrient composition.

Weight, height, age and gender were registered prior to the low-calorie diet (LCD). Weight was furthermore registered at the end of the LCD-period (to calculate weight loss during the LCD) and monthly during the 6-month dietary weight maintenance period. Blood samples were drawn after an overnight fast immediately prior to the 6-month dietary weight maintenance period and samples were stored and analyzed for fasting glucose and fasting insulin as previously reported (6). More information about the study can be found elsewhere (6).

Participants were stratified into glycemic categories by pre-treatment FPG (<90 mg/dL and 90-105 mg/dL) after having lost ≥8% of bodyweight during an 8 weeks LCD-period (no subjects had FPG>105 mg/dL [FPG>5.8 mmol/L]). Insulinemic categories was based on the median fasting insulin value (FI≤50 pmol/L; FI>50 pmol/L) among participants with high FPG (90-105 mg/dL). No glucose and insulin measures exist prior to the 8-week weight loss period as was used in a prior study (8); hence, the FPG cut-off was lowered from 100 mg/dL inspired by the American Diabetes Association (7) to 90 mg/dL in the present study.

Baseline characteristics were summarized as mean±standard deviation (SD), median (interquartile range [IQR]), or as proportions. Differences in baseline characteristics between glycaemic groups were assessed using two-sample t-tests (variables possibly transformed before analysis) or Pearson's chi-squared tests. Pearson correlations were carried out between 6 months weight change and FPG as well as FI at each of the three diets. Differences in weight change between glycaemic and insulinemic groups (and the combination of the two) were analyzed by means of linear mixed models using completers. The linear mixed models comprised fixed effects including age, gender, baseline BMI, and LCD weight loss, as well as random effects for subjects. Results are shown as mean weight change with 95% confidence interval (CI). Differences in weight change between diets were compared within and between each blood marker group through pairwise comparisons using post hoc t-tests. The level of significance was set at P<0.05 and statistical analyses were conducted using STATA/SE 14.1 (Houston, USA).

Results

The 104 completers [(MUFA, n=38) (NNR, n=42), (ADD, n=24)] were 28.2±4.7 years old, had a median (IQR) baseline BMI of 31 (29.3;33.0), consisted of 45% men, and lost a median (IQR) of 12.3 (9.7;15.2) kg during the LCD period. Participants categorized as having high FPG (n=38) lost 2.0 kg (95% CI 0.5;3.5, P=0.011) more on the LCD compared to the participants categorized as having low FPG (n=66). Proportionally more males compared to females was categorized as having high FPG (57% vs. 19%, P<0.001) whereas no age (P=0.10) or BMI (P=0.52) difference was observed between glycemic groups. The actual dietary composition was within the prescribed ranges and is reported elsewhere (6).

The correlation between baseline FPG and weight change after 6-month was r=−0.02 (P=0.90) on MUFA, r=−0.27 (P=0.088) on NNR, and r=0.41 (P=0.046) on ADD. The correlation between baseline FI and weight change after 6-month was r=−0.06 (P=0.72) on MUFA, r=0.06 (P=0.71) on NNR, and r=0.25 (P=0.25) on ADD.

Figure 15:
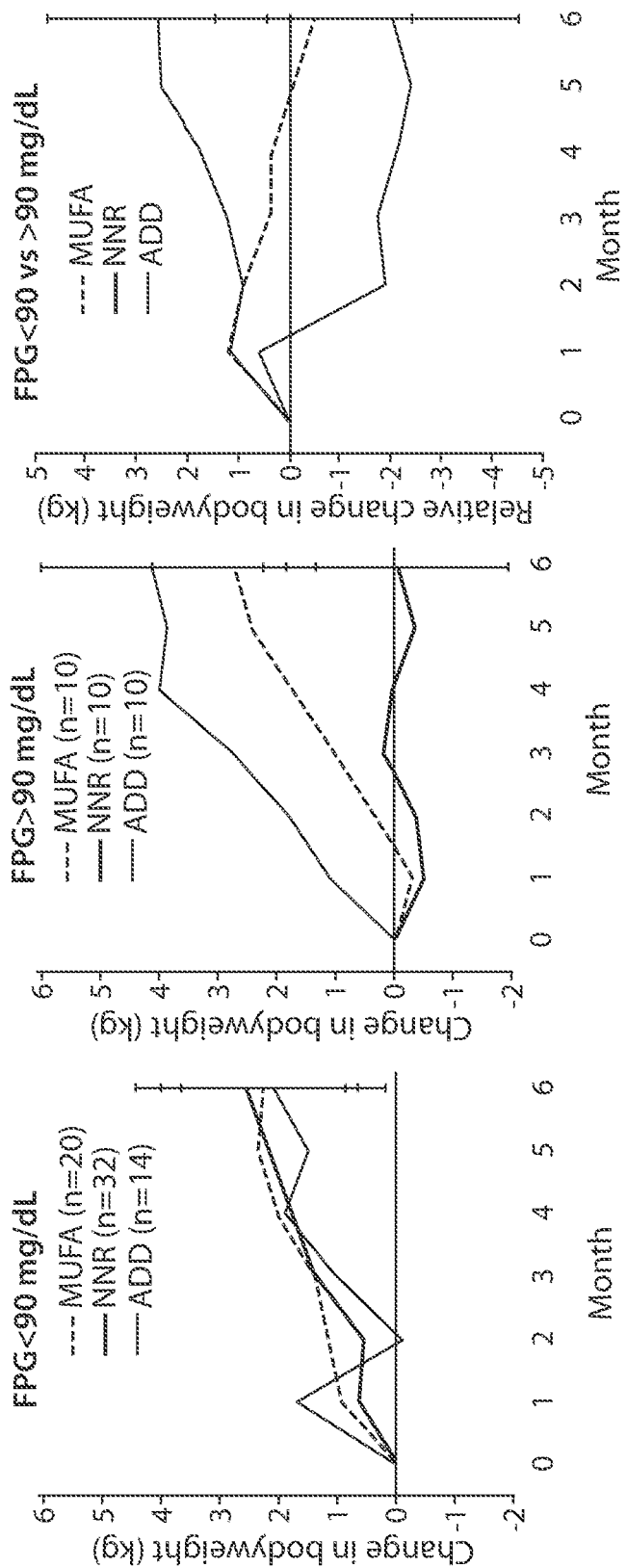
FIG. 15 shows change in body weight among participants <90 mg/dL, >90 mg/dL and the relative difference between these two phenotypes on MUFA, NNR and ADD. Abbreviations: FPG, Fasting plasma glucose. Data are presented as estimated mean weight change from baseline and 95% confidence intervals for each combination of the diet-time-FPG strata interaction in the linear mixed models, which were additionally adjusted for age, gender, BMI, and LCD weight loss, and subjects. ¥ indicate significant difference between the diets (P<0.05); § indicate significant difference from zero (P<0.05).

Participants with low FPG and randomized to MUFA, NNR and ADD regained 2.26 kg (0.92;3.59, P=0.001), 2.54 kg (1.50;3.59, P<0.001) and 2.09 kg (0.50;3.69, P=0.010) after 26 weeks, respectively, with no differences between the three diets (all P>0.64) (FIG. 15). Participants with high FPG and randomized to MUFA, NNR and ADD regained 2.73 kg (1.33;4.13, P<0.001), −0.05 kg (−1.95;1.86, P=0.96) and 4.16 kg (2.27;6.06, P<0.001) after 26 weeks, respectively, resulting in lower weight regain on NNR compared to ADD [−4.21 kg (−6.83;−1.59), P=0.002] and MUFA [−2.77 kg (−5.12;−0.43), P=0.020] (no difference between MUFA and ADD; P=0.23) (FIG. 15). Consequently, participants with high compared to low FPG regained more on ADD compared to NNR [4.66 kg (1.43;7.88), P=0.005] and MUFA compared to NNR [3.06 kg (0.18;5.94), P=0.037] (no difference between MUFA and ADD; P=0.31) (FIG. 15).

Figure 16:
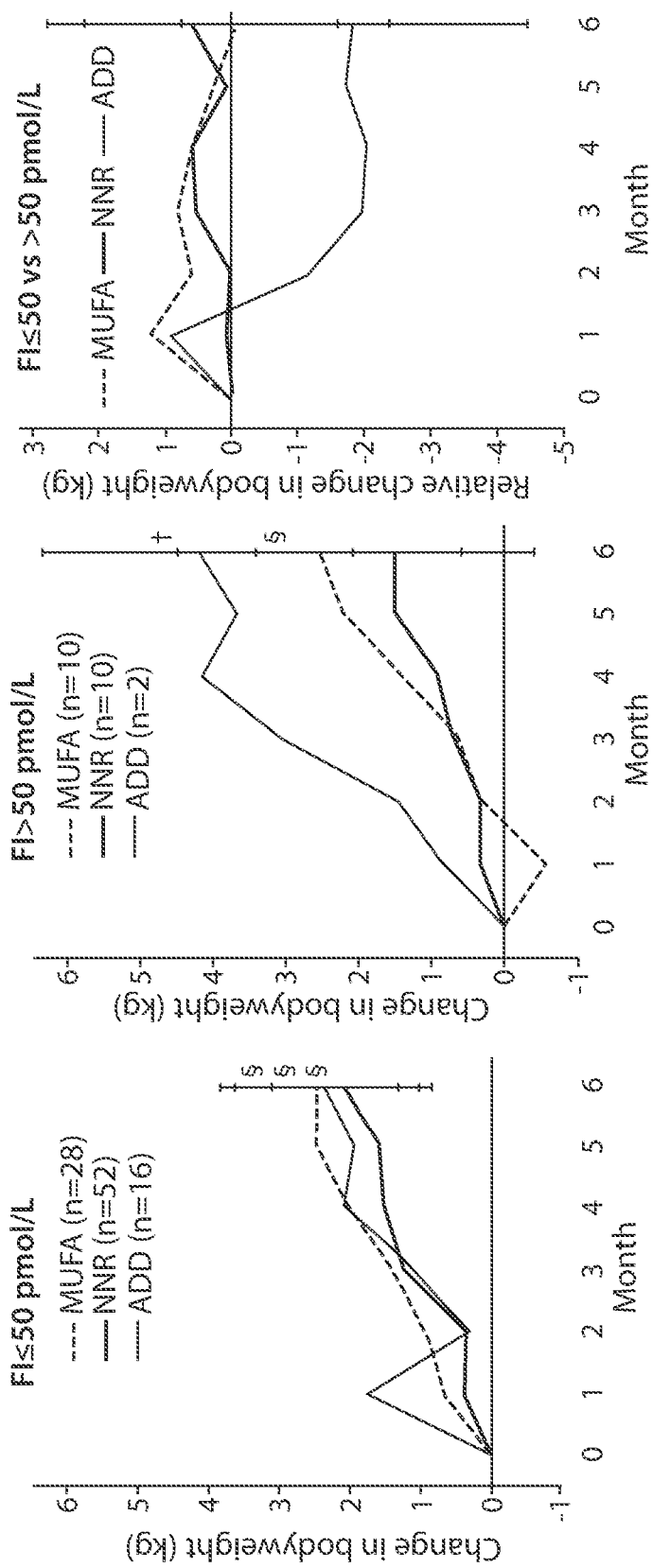
FIG. 16 shows changes in body weight among participants ≤50 pmol/L, >50 pmol/L and the relative difference between these two phenotypes on MUFA, NNR and ADD. Abbreviations: FI, Fasting insulin. Data are presented as estimated mean weight change from baseline and 95% confidence intervals for each combination of the diet-time-FPG strata interaction in the linear mixed models, which were additionally adjusted for age, gender, BMI, and LCD weight loss, and subjects. ¥ indicate significant difference between the diets (P<0.05); § indicate significant difference from zero (P<0.05).

Participants with low FI and randomized to MUFA, NNR and ADD regained 2.46 kg (1.30;3.61, P<0.001), 2.07 kg (1.02;3.12, P<0.001) and 2.35 kg (0.86;3.83, P=0.002) after 26 weeks, respectively, with no differences between the three diets (all P>0.63) (FIG. 16). Participants with high FI and randomized to MUFA, NNR and ADD regained 2.52 kg (0.57;4.46, P=0.011), 1.49 kg (−0.42;3.40, P=0.13) and 4.19 kg (0.86;3.83, P=0.002) after 26 weeks, respectively, with no differences between the three diets (all P>0.061) (FIG. 16). Consequently, no differences in responsiveness to the diets were found between individuals with low and high FI (all P≥0.16) (FIG. 16).

Figure 17:
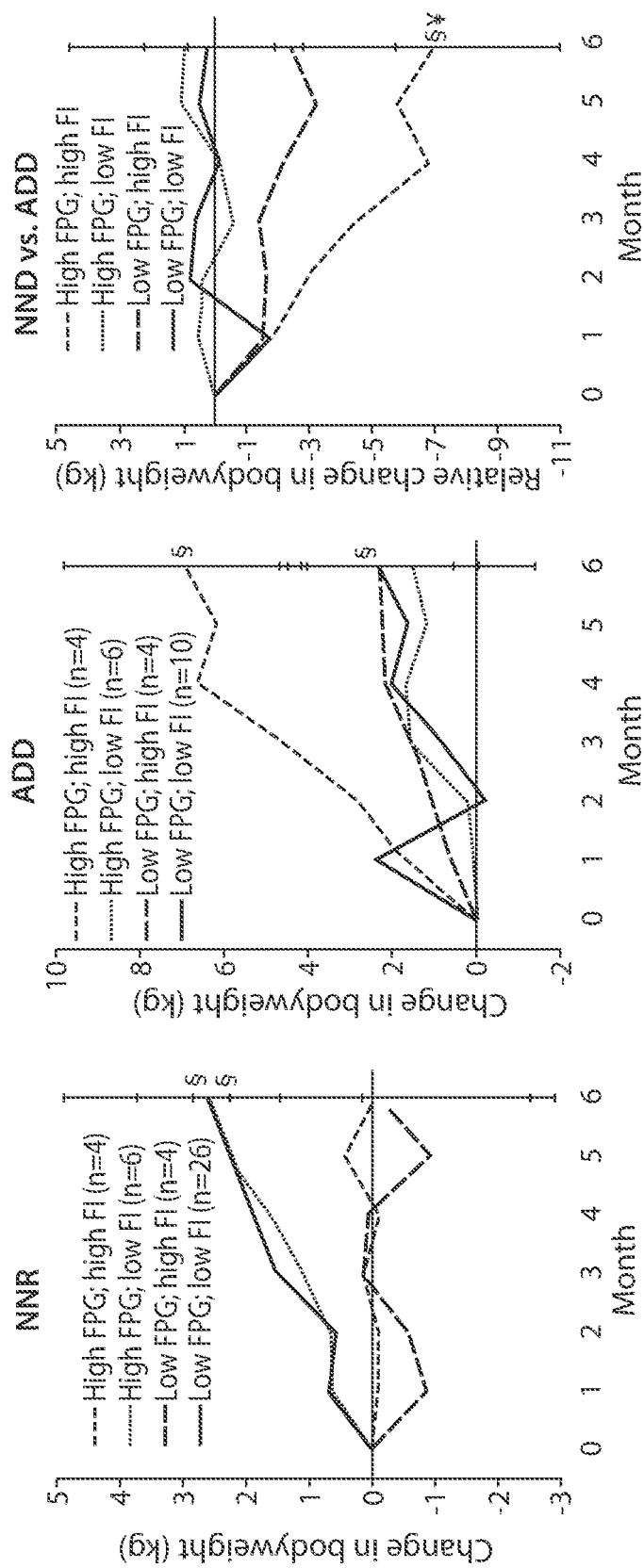
FIG. 17 shows change in body weight among participants with the four phenotypes of FPG and FI on NNR, ADD and the relative difference between NND and ADD. Abbreviations: FI, Fasting insulin; FPG, Fasting plasma glucose. Data are presented as estimated mean weight change from baseline and 95% confidence intervals for each combination of the diet-time-FPG strata interaction in the linear mixed models (except for the MUFA-diet as n=1 in one of the four phenotypes), which were additionally adjusted for age, gender, BMI, and LCD weight loss, and subjects. ¥ indicate significant difference between the diets (P<0.05); § indicate significant difference from zero (P<0.05).
Figure 18A:
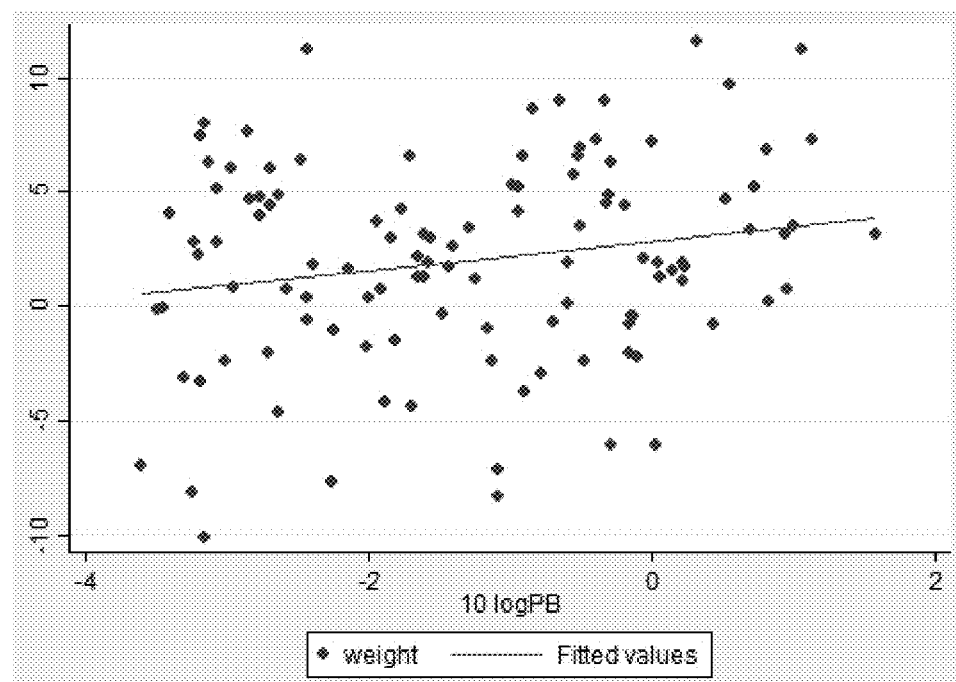
FIG. 18A is a line graph showing the *Prevotella/Bacteroides*-ratio (P/B-ratio) including all subjects wherein x-axis: log (*Prevotella/Bacteroides*), y-axis: 24-week weight change (kg) and r=Pearson correlation coefficient of r=0.195 (P=0.040)].
Figure 18B:
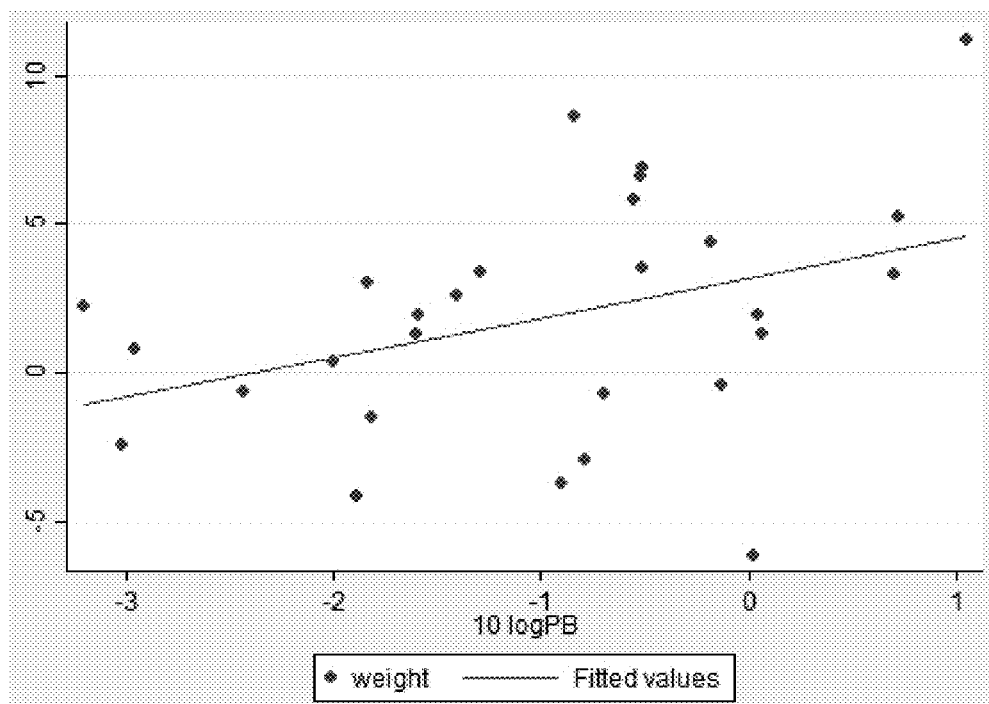
FIG. 18B is a line graph showing the *Prevotella/Bacteroides*-ratio (P/B-ratio) for the maltodextrin group only wherein x-axis: log (*Prevotella/Bacteroides*), y-axis: 24-week weight change (kg) and r=Pearson correlation coefficient of r=0.381 (P=0.045)].
Figure 19A:
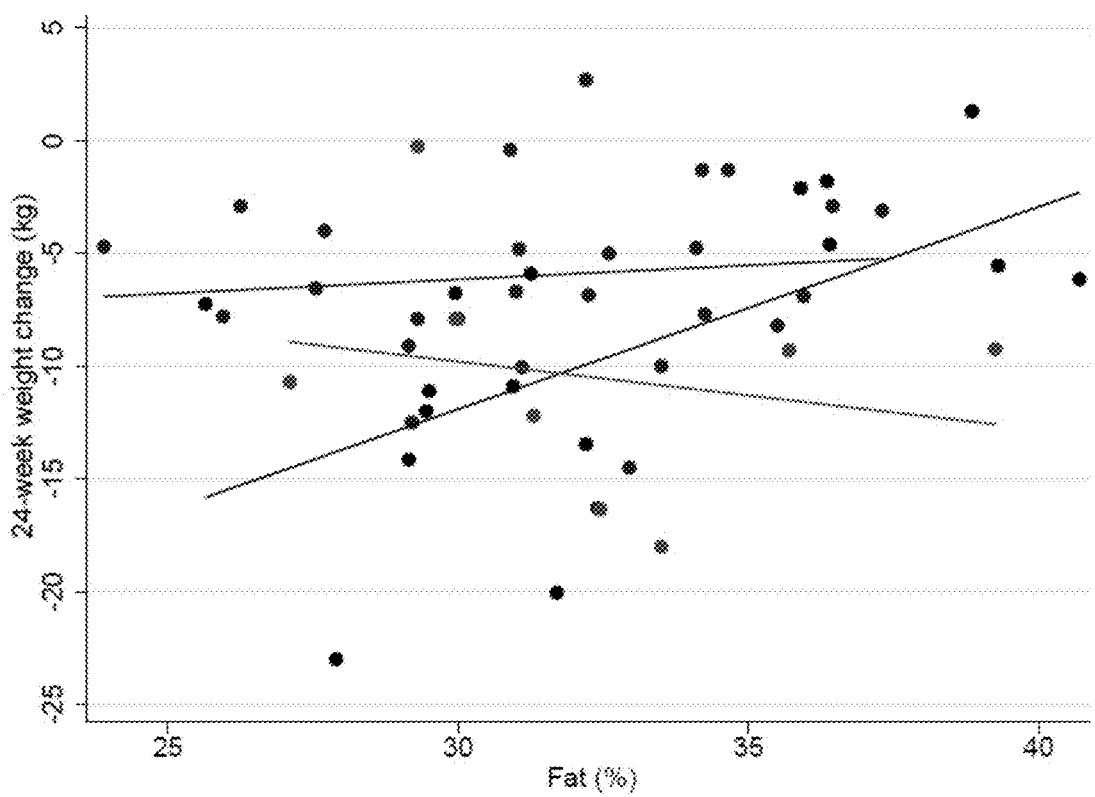
FIG. 19A is a scatter plot showing dietary composition and 24-week weight loss stratified by three *Prevotella/Bacteroides* groups. Blue: Low P/B-ratio (n=26); Black: High P/B-ratio (n=17); Red: 0-*prevotella* (n=8). Pearson's correlation coefficients between energy intake and weight change were 0.01 (P=0.97), 0.32 (P=0.20), and 0.08 (P=0.86) among subjects with low P/B-ratio, high P/B-ratio and 0-*Prevotella*, respectively. The remaining correlation coefficients are listed in Table S2.
Figure 19B:
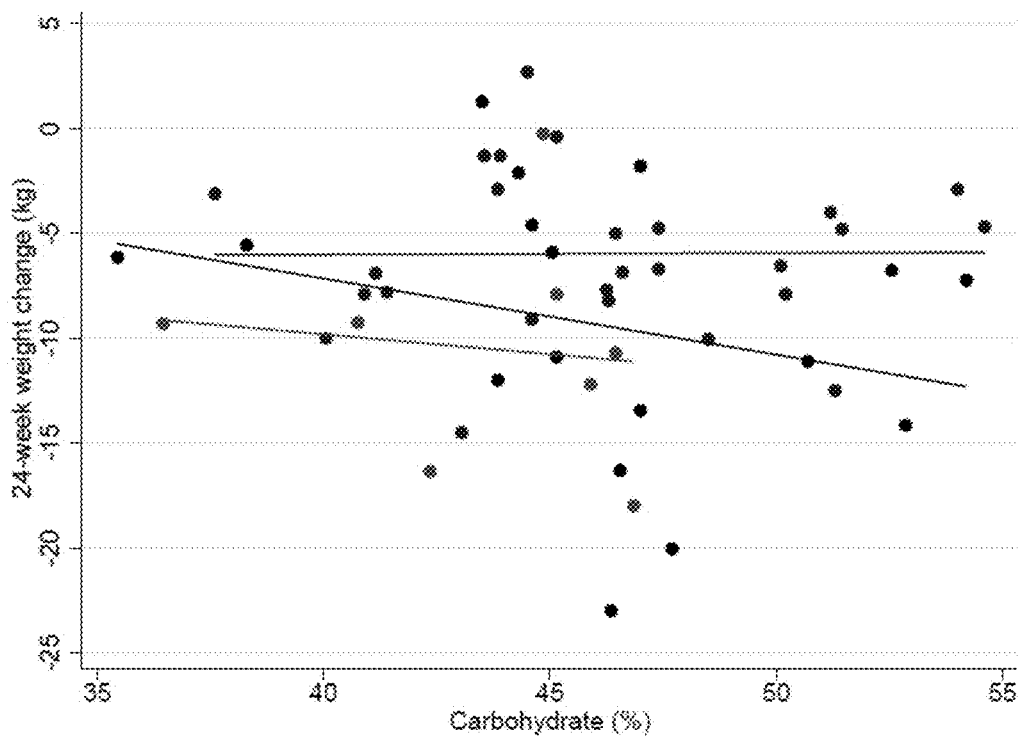
FIG. 19B is a scatter plot showing dietary composition and 24-week weight loss stratified by three *Prevotella/Bacteroides* groups. Blue: Low P/B-ratio (n=26); Black: High P/B-ratio (n=17); Red: 0-*prevotella* (n=8). Pearson's correlation coefficients between energy intake and weight change were 0.01 (P=0.97), 0.32 (P=0.20), and 0.08 (P=0.86) among subjects with low P/B-ratio, high P/B-ratio and 0-*Prevotella*, respectively. The remaining correlation coefficients are listed in Table S2.
Figure 19C:
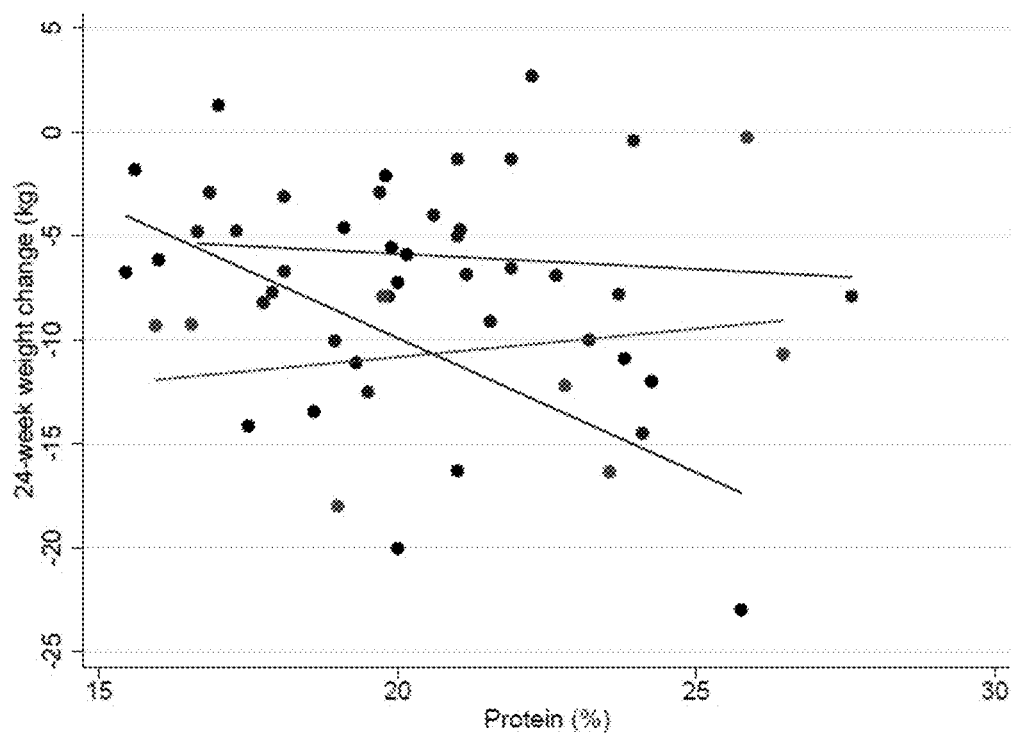
FIG. 19C is a scatter plot showing dietary composition and 24-week weight loss stratified by three *Prevotella/Bacteroides* groups. Blue: Low P/B-ratio (n=26); Black: High P/B-ratio (n=17); Red: 0-*prevotella* (n=8). Pearson's correlation coefficients between energy intake and weight change were 0.01 (P=0.97), 0.32 (P=0.20), and 0.08 (P=0.86) among subjects with low P/B-ratio, high P/B-ratio and 0-*Prevotella*, respectively. The remaining correlation coefficients are listed in Table S2.
Figure 19D:
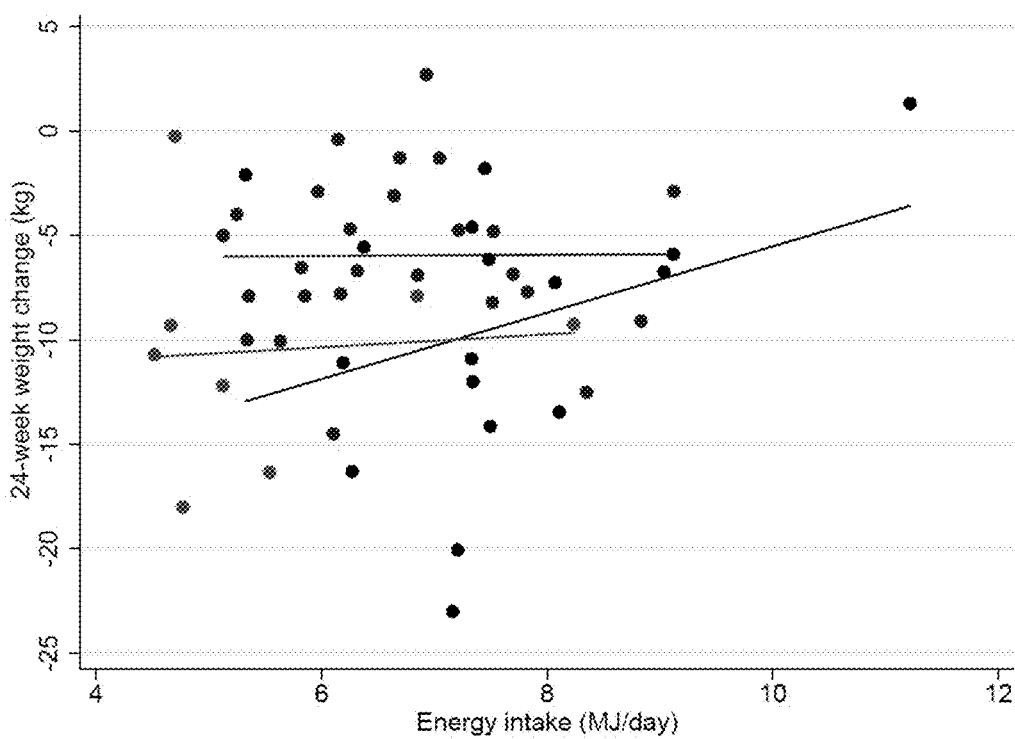
FIG. 19D is a scatter plot showing dietary composition and 24-week weight loss stratified by three *Prevotella/Bacteroides* groups. Blue: Low P/B-ratio (n=26); Black: High P/B-ratio (n=17); Red: 0-*prevotella* (n=8). Pearson's correlation coefficients between energy intake and weight change were 0.01 (P=0.97), 0.32 (P=0.20), and 0.08 (P=0.86) among subjects with low P/B-ratio, high P/B-ratio and 0-*Prevotella*, respectively. The remaining correlation coefficients are listed in Table S2.

Participants with high FPG and high FI regained 6.95 kg (2.92;10.98, P=0.001) less on the NNR than the ADD, whereas no difference was observed for the other three phenotypes (P≥0.15) (FIG. 17).

Discussion

We confirmed FPG—with and without the presence of FI—to be an important biomarker that is associated with dietary weight loss maintenance success on ad libitum diets varying in macronutrient and fiber composition. Again, we show that overweight and obese participants with slightly elevated fasting blood glucose are extremely susceptible to weight regain on a western diet, but can, on the other hand refrain from weight regain on a diet lower in fat, added sugar, and energy density as well as higher in fiber even without prescribing calorie restriction per se.

We have previously reported no overall difference in weight maintenance between the three diets with a weight regain in MUFA, NNR and ADD of 2.5, 2.2, and 3.8 kg (P for difference between groups 0.31) (6). However, we now report that this insignificant overall 1.6 kg difference between NNR and ADD was due to a more than four kg difference in participants with high FPG and absolutely no difference among participants with low FPG. Further stratifying on FI revealed that the difference between these two diets was driven by an almost 7 kg difference among participants with high FPG and high FI. Recently, the New Nordic Diet, closely resembling the NNR diet of the present study, was also found to be superior among subjects with higher FPG when compared to the ADD (8). Contrary to the present study the subjects with high FPG and either low or high FI, was found to benefit equally (≈6 kg) of the New Nordic Diet compared to the ADD. Possible explanations that make the direct comparison between the two studies somewhat difficult and possibly could explain the slight deviations between the results could, besides the low numbers in each group when stratified on both FPG and FI, be the lower age, larger proportion of males, and the presence of a LCD-period in the MUFOBES study that could affect the actual level and the cut-offs for the two biomarkers, FPG and FI. Finally, according to our recently published study (8) the moderate fat diet high in fiber (MUFA) is likely to be superior among participants with FPG>115 mg/dL. However, no subjects in the current analysis had FPG>105 mg/dL and this MUFA diet warrant further investigation among participants with higher FPG.

In conclusion, slightly elevated pre-treatment FPG predicts success in dietary weight loss maintenance among overweight patients on ad libitum diets differing in fat, carbohydrate, energy density, added sugar and fiber. This easily accessible biomarker could potentially help stratifying patients in personalize dietary guidance for overweight and obesity in order to magnify weight loss and optimize weight maintenance.

REFERENCES

1. Cornier M, Donahoo W T, Pereira R, Gurevich I, Westergren R, Enerback S, et al. Insulin sensitivity determines the effectiveness of dietary macronutrient composition on weight loss in obese women. Obes Res. 2005; 13(4):703-9.

2. McClain A D, tten J J, Hekler E B, Gardner C D. Adherence to a low-fat vs. low-carbohydrate diet differs by insulin resistance status. Diabetes, Obesity and Metabolism. 2013; 15(1):87-90.

3. Gardner C D, Offringa L C, Hartle J C, Kapphahn K, Cherin R. Weight loss on low-fat vs. low-carbohydrate diets by insulin resistance status among overweight adults and adults with obesity: A randomized pilot trial. Obesity. 2016; 24(1):79-86.

4. Pittas A G, Das S K, Hajduk C L, Golden J, Saltzman E, Stark P C, et al. A low-glycemic load diet facilitates greater weight loss in overweight adults with high insulin secretion but not in overweight adults with low insulin secretion in the CALERIE Trial. Diabetes Care. 2005 December; 28(12):2939-41.

5. Ebbeling C B, Leidig M M, Feldman H A, Lovesky M M, Ludwig D S. Effects of a low-glycemic load vs low-fat diet in obese young adults: a randomized trial. JAMA. 2007; 297(19):2092-102.

6. Due A, Larsen T M, Mu H, Hermansen K, Stender S, Astrup A. Comparison of 3 ad libitum diets for weight-loss maintenance, risk of cardiovascular disease, and diabetes: a 6-mo randomized, controlled trial. Am J Clin Nutr. 2008 November; 88(5):1232-41.

7. American Diabetes Association. 2. Classification and Diagnosis of Diabetes. Diabetes Care. 2016 January; 39 Suppl 1:S13-22.

8. Hjorth M F, Ritz C, Blaak E E, Saris W H M, Langin D, Poulsen S K, Larsen T M, Sorensen T I A, Zohar Y, Astrup A (2017) Pre-treatment fasting plasma glucose and insulin modify dietary weight loss success: results from three randomized clinical trials. Am. J. Clin. Nutr. (Accepted).

Example 4: Combining Evidence from DiOGenes and MUFOBES Studies

DiOGenes Study

We reanalyzed a randomized clinical trial referred to as the Diet, Obesity, and Genes (DiOGenes) conducted in eight European countries. As part of the larger dietary weight maintenance trial DiOGenes, a total of 316 overweight and obese participants following successful loss of ≥8% body mass during an 8-week low-calorie weight-loss phase, were randomly assigned to an ad libitum low glycemic-load (low carbohydrate and low glycemic index) or high glycemic-load (high carbohydrate and high glycemic index) weight maintenance diet for 26 weeks. Dietary fat content was held constant (~30 Energy %) between the two diets. Before the initial weight loss phase blood samples were drawn fasted from where FPG and FI were analyzed.

During the 8-week weight-loss phase, participants received a low-calorie diet that provided 3.3 MJ (800 kcal) per day with the use of Modifast products (Nutrition et Santé). Participants could also eat up to 400 g of vegetables (providing a maximum of approximately 200 kcal), providing a total, including the low-calorie diet, of 3.3 to 4.2 MJ (800 to 1000 kcal) per day. The macronutrient composition of the 800 kcal LCD diet was proximally 51E % Carbohydrate, 27E % protein, 18E % fat, and 4E % Fiber.

Subjects were classified as high FPG/low FPG (high/low FPG) before they started the low-calorie diet (LCD). Weight loss during the 8-week low calorie diet was lower among prediabetics compared to non-diabetic obese subjects [−0.76 (−1.20;−0.31) kg; P=0.001] and fat loss tended to be lower [−0.98 (−2.00;0.03) P=0.058]. These analyses have been adjusted for potential differences in age, gender and baseline BMI between the FPG groups.

MUFOBES Study

During the 8-week weight-loss phase of the MUFOBES study of Example 3, participants received a low-calorie diet that provided 3.3 to 4.2 MJ (800 to 1000 kcal) per day. The macronutrient composition of the LCD diet was proximally 40E % Carbohydrate, 40E % protein, and 20E % fat.

Subjects were classified as high f-BG (>90 mg/dL as measured after the LCD-period corresponding to approximately >95 if measured before LCD-period) and low f-BG (<90 mg/dL as measured after the LCD-period corresponding to approximately <95 if measured before LCD-period). Weight loss during the 8-week low calorie diet was 12.0 kg (95% CI 11.2;12.9) among subjects with low FPG and 14.0 kg (95% CI 12.6;15.4) among those with high FPG corresponding to a 2.0 kg (95% CI 0.5;3.5) weight loss among subjects with high compared to low FPG. After adjusting this analysis for potential differences in age, gender and baseline BMI between the FPG groups this difference attenuated to an insignificant 0.3 kg (95% CI −1.0;1.6) higher weight loss among subjects with high compared to low FPG.

Combining Evidence from DiOGenes and MUFOBES:

We therefore have evidence to support the importance of low carb/high protein LCD for individuals with prediabetes or with FPG>approximately 95 mg/dL (measured before the LCD-period).

Example 5: Pre-Treatment Microbial Prevotella-to-Bacteroides Ratio Determines Body Weight and Fat Loss Success on Diets Varying in Macronutrient Composition and Dietary Fiber Introduction Current interventions and policies have failed to stop the rise in the global obesity epidemic. Numerous randomized controlled trials have compared a myriad of diets for the treatment of obesity based on the assumption that one diet fits all without being able to provide strong evidence in favor of one or the other (1-5).

Accumulating evidence is linking gut microbiota to obesity. Overall, individuals with obesity show decreased bacterial diversity (6) and gene richness (7, 8) and fecal transplantation even suggest a causal relationship between the microbiome and obesity (9-11). The composition of the gut microbiota has the potential to affect the efficacy of energy harvest (12) particularly though the fiber-utilization capacity (13), to influence the secretion of gastrointestinal hormones affecting appetite (14, 15), and potentially to affect human behaviour through the gut-brain-axis (16). Of note, the metabolic responses to different diets were recently shown to vary between individuals depending on the composition of their gut microbiota (17, 18). Therefore, the human gut microbiota has the potential to play a pivotal role in obesity management through personalized nutrition.

Studies have suggested that the microbiota of individuals can be clustered into so-called enterotypes based on the genus composition (19) suggesting that such compositional differences may reflect dietary intake and determine the individual responses to different diets. The Bacteroides-driven enterotype is reported to be predominant in individuals with a high intake of protein and animal fat (Western diet), whereas the Prevotella-driven enterotype appears predominant in individuals that consume diets rich in carbohydrate and fiber (20-22). The intestinal microbial communities are resilient and difficult to change through dietary interventions (20, 21, 23, 24), unless extreme changes, such as complete removal of carbohydrates from the diet, are introduced (25). However, only a limited number of studies have related microbial enterotypes to health markers, such as cholesterol and LDL (14, 22-24). In a randomized clinical study we recently reported that participants with high Prevotella-to-Bacteriodes (P/B) ratio were more susceptible to lose body fat on diets high in fiber than subjects with a low P/B ratio (24). Furthermore, participants with no detectable Prevotella spp. had a weight loss response similar to that of participants with high P/B ratio, suggesting that other bacterial genera might also be involved.

The aim of the present study was to validate this recent finding (24) by re-analyzing an independent 24-week dietary intervention study (26) for potential differences in weight loss response between participants with no detectable Prevotella spp., low P/B ratio, and high P/B ratio independently of the allocated diets and stratified by macronutrient and fiber intake from the 7-day dietary records. As previously reported (26) no difference in macronutrient composition, dietary fiber, or 24 week weight loss response was observed between the two allocated diets (high and low dairy). Therefore, it was hypothesized that participants stratified into the low- and high P/B ratio group would not respond differently to the two allocated diets. However, as both the allocated diets were relatively low in fat and high in protein, carbohydrate and dietary fiber, it was hypothesized that participants with high P/B ratio (and possibly also participants with no detectable Prevotella spp.) would lose more body weight and body fat compared to participants with low P/B ratio, especially when consuming a diet high in dietary fiber evaluated by 7-day dietary records.

Materials and Methods

As previously reported (26), potential participants were invited for an information meeting and a physical examination at a screening visit after signing the informed consent. Inclusion criteria were: 1) Habitual calcium intake <800 mg/d, 2) No dairy food allergies, 3) No infectious or metabolic diseases, 4) No use of dietary supplements during the study or 6 months prior to the study, 5) No use of cholesterol lowering medicine or other medication that would be expected to affect the study outcomes, 6) No gastrointestinal diseases, 7) No participation in other clinical studies, and 8) Women could not be pregnant or lactating. A total of 96 overweight or obese (BMI 28-36 kg/m$^2$) men and women aged 18-60 years met the inclusion criteria of whom 80 participants were included in the study, which 52 completed all 24 weeks. In this randomized, controlled, parallel design, participants were allocated to a 500 kcal (2100 kJ)/d energy deficit diet with a macronutrient composition of 30 energy percentage (E %) fat, 52 E % carbohydrate and 18 E % protein that was either high (≈1500 mg calcium/day of which 1200 mg calcium/day should be consumed in the form of dairy products) or low (<600 mg calcium/day) in dairy products during a 24 week period. Energy requirements were determined at the dietary counselling visit at baseline and adjusted after 12 weeks based on body weight, gender, age (27), and physical activity level assessed by Baeckes questionnaire (28). Randomization was performed by staff not involved in screening of the participants and performed according to four strata: 1) women with BMI≤31 kg/m$^2$, 2) women with BMI>31 kg/m$^2$, 3) men with BMI≤31 kg/m$^2$, 4) men with BMI>31 kg/m$^2$. The participants attended seven individual dietary counselling visits and one group session scheduled at week 0, 2, 4, 8, 12, 16, 20 and 24 where body weight was also recorded to the nearest 0.1 kg (Lindeltronic 8000S, Lindell's, Malmo, Sweden). At baseline and after 24 weeks, a fecal sample was collected at home, immediately cooled, transported to the Department as soon as possible, and aliquots were stored immediately at −80° C. Bacterial DNA was extracted from frozen fecal samples using the NUCLEOSPIN® soil kit (Macherey-Nagel, Düren, Germany), 5 ng DNA was used to amplify the V3+V4 region of 16S rDNA genes, and operational taxonomic unit (OTU) picking was performed with 97% sequence similarity as previously described (26). The relative abundances of sequences assigned to the Prevotella and Bacteroides genera were summarized. Furthermore, fasting blood samples were drawn at baseline, from where the concentrations of plasma glucose and serum insulin were analyzed as described elsewhere (26). At baseline and week 24, body composition was determined by DXA (Lunar Prodigy DXA, Madison, USA) during standardized conditions. Finally, 7-day dietary records were obtained at both week 12 and 24, of which the mean value was calculated. From these mean values the intake of carbohydrate, protein, fat, and dietary fiber were categorized as being low or high based on the median split. Participants were instructed not to alter their habitual lifestyle throughout the study period beyond the instructions regarding the intervention and furthermore to refrain from physical activity, medicine and alcohol 48 hours prior to the visits. More information about the study can be found elsewhere (26).

The study was conducted according to the guidelines laid down in the Declaration of Helsinki and all procedures involving human subjects were approved by the Danish National Committee on Health Research Ethics. Written informed consent was obtained from the participants after receiving oral and written information about study procedures. The study was registered on clinicaltrials.gov with the identifier: NCT01199835.

Statistics

Two pre-treatment P/B groups were identified by plotting, for each sample, the log-transformed-relative abundance of *Bacteroides* spp. versus the log-transformed-relative abundance of *Prevotella* spp. as well as creating a histogram plotting frequency of the log-transformed-relative abundance of *Prevotella* spp./*Bacteroides* spp. As indicated by a recent study (24), subjects with no detectable *Prevotella* bacteria constituted a third group (named 0-*Prevotella*).

Baseline characteristics were summarized as mean±standard deviation, median (interquartile range) or proportions (%). Differences between the three P/B groups were tested using one-way ANOVA (some variables transformed before analysis) with Bonferroni post-hoc test or Pearson's chi-squared test.

Correlations between mean carbohydrate, fat, protein and fiber intake during the 24 weeks were analyzed by means of Pearson's correlation coefficients and partial correlation coefficients (mutual adjustment of dietary components).

Differences in body weight change from baseline between P/B groups on the two allocated diets were analyzed by means of linear mixed models using all available measurements. The linear mixed models included the three-way interaction between diet×time×P/B group strata as well as all nested two-way interactions and main effects and comprised additional fixed effects including age, gender, baseline BMI, baseline fasting glucose and insulin as well as random effects for subjects. Secondly, a similar analysis was carried out only removing the allocated diet from the interaction term and instead including it as a covariate (same analysis was done for body fat as outcome). Finally, a similar analysis was carried out but only replacing the two allocated diets with median split of self-reported dietary intake (fat E %, protein E %, carbohydrate E %, and fiber g/10 MJ) one at a time (Model 2) while including the allocated diet as a covariate. Model 3 additionally include fat, protein, carbohydrate, and fiber as continues variables (except when included as exposure). Model 1 included no covariates.

Results are shown as correlations and mean weight change from baseline with 95% confidence interval (CI), and differences in weight change from baseline to end of study (week 24) were compared between allocated diets as well as median split of self-reported diets within each P/B group and between P/B groups (irrespective of diets) through pairwise comparisons using post hoc t-tests. All data were checked for normality and variance homogeneity. The level of significance was set at P<0.05 and statistical analyses were conducted using STATA/SE 14.1 (Houston, USA).

Results

Median (IQR) dietary distribution during the 24-weeks was 45.9 (43.6;47.7) E % carbohydrates, 31.7 (29.3;34.7) E % fats, 20.0 (18.1;22.7) E % proteins, and 30.8 (26.1;36.0) g/10 MJ dietary fibers.

Figure 1B:
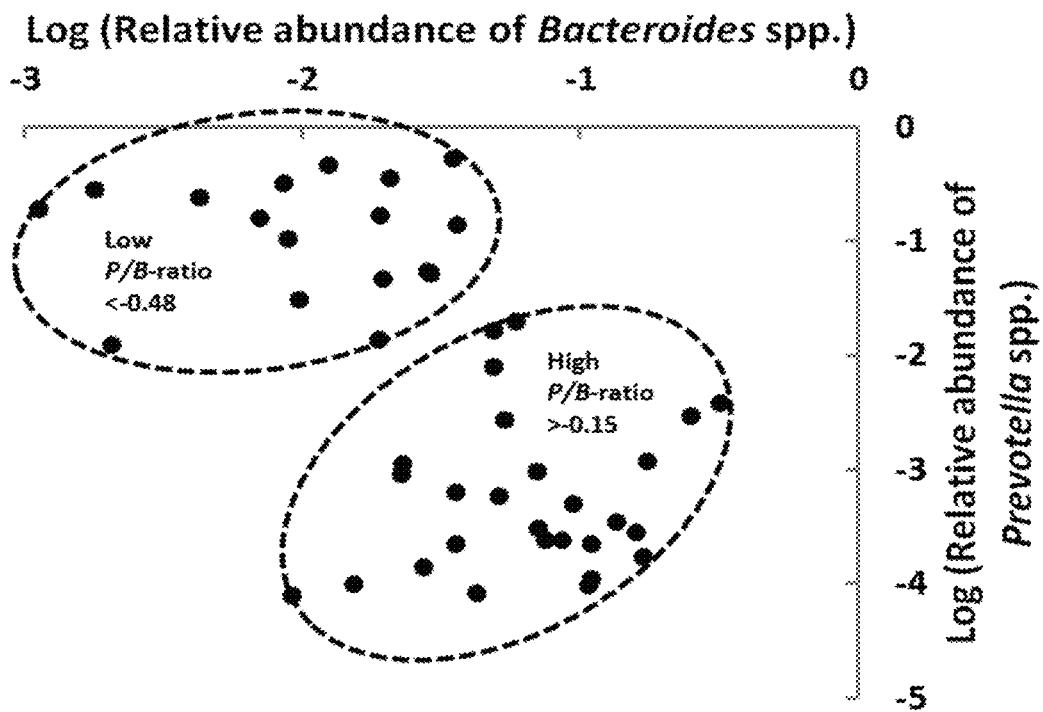
FIG. 1B is a scatter plot showing two distinct groups of participants that were observed prior to intervention based on the log-transformed relative abundance of *Bacteroides* spp. and the log-transformed relative abundance of *Prevotella* spp.—indicated with dotted lines and referred to as low (n=27) and high (n=17) *Prevotella*-to-*Bacteriodes* (P/B) groups. Participants with no detectable *Prevotella* spp., referred to as the 0-*Prevotella* group, constitute the third group (n=8) but was excluded from this figure.

The low and high P/B groups are indicated with dotted lines in FIG. 1B. A third group (n=8) had no detectable *Prevotella* spp. and constitute a third group named 0-*Prevotella*.

Overall, body weight, BMI, and the relative abundance of *Bacteroides* spp. and *Prevotella* spp. differed between the three P/B groups (P≤0.017), with the high P/B group having higher body weight, BMI, relative abundance of *Prevotella* spp. and lower relative abundance of *Bacteroides* spp. compared to the low P/B group (P<0.05) (Table 6).

TABLE 6

Baseline characteristics of the study participants stratified into three groups according to *Prevotella*-to-*Bacteroides* (P/B) ratio

|  | 0-Prevotella[1] (n = 8) | Low P/B group (n = 27) | High P/B group (n = 17) | P-value |
| --- | --- | --- | --- | --- |
| Age (year) | 47.9 ± 6.8 | 43.4 ± 8.7 | 41.8 ± 11.5 | 0.33 |
| Gender (% female/male) | 100/0 | 88.9/11.1 | 76.5/23.5 | 0.24 |
| Body weight (kg) | 82.6 ± 4.6[a] | 84.5 ± 11.4[a] | 95.1 ± 12.0[b] | 0.005 |
| Body mass index (kg/m$^2$) | 30.7 ± 1.1[ab] | 29.7 ± 2.2[a] | 31.9 ± 2.8[b] | 0.017 |
| Body fat (%) | 48.7 ± 3.9 | 44.9 ± 4.1 | 44.4 ± 5.0[2] | 0.069 |
| Fasting glucose (mmol/L) | 5.42 ± 0.46 | 5.55 ± 0.37 | 5.70 ± 0.55 | 0.33 |
| Fasting insulin (pmol/L) | 63.4 (47.0; 88.1) | 38.5 (23.7; 69.3)[3] | 47.8 (28.8; 54.6) | 0.17 |
| *Prevotella* (relative abundance) | 0 (0; 0)[a] | 0.0003 (0.0002; 0.001)[b] | 0.155 (0.052; 0.278)[c] | <0.001 |
| *Bacteroides* (relative abundance) | 0.097 (0.032; 0.139)[a] | 0.071 (0.036; 0.111)[a] | 0.012 (0.007; 0.021)[b] | <0.001 |
| *Prevotella*-to-*Bacteroides* ratio | — | 0.004 (0.001; 0.012) | 11.67 (3.11; 36.03) |  |

Abbreviation:
P/B, *Prevotella*-to-*Bacteroides*.
Data are presented as mean ± standard deviation, median (interquartile range) or proportions (%) and differences between the three P/B groups were tested using one-way ANOVA with Bonferroni post-hoc tests (some variables transformed before analysis) or Pearson's chi-squared test. Different alphabets within a row (a, b, c) indicate significant differences (P < 0.05).
[1]0-*Prevotella* refers to the group of individuals with no detectable *Prevotella* spp. before intervention.
[2]n = 16 (missing data for one individual)
[3]n = 26 (missing data for one individual)

Figure 2:
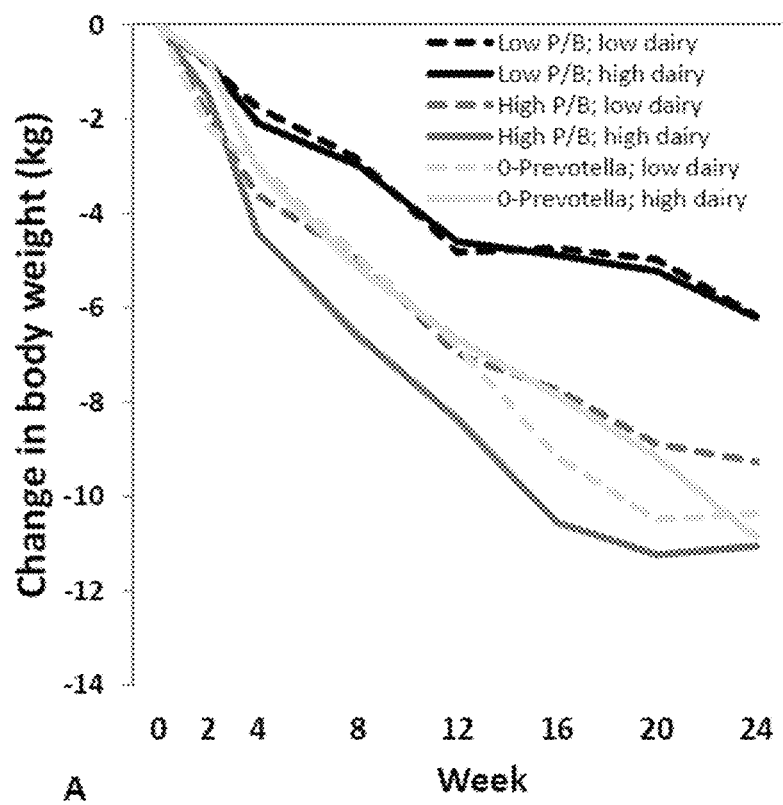
FIG. 2 shows line graphs illustrating the change in body weight between (panel A) and within (panel B) diets when stratified into three groups according to *Prevotella*-to-*Bacteroides* (P/B) ratio. Data are presented as estimated mean weight change from baseline for each combination of the A) diet-time-P/B strata interaction or B) time-P/B strata interaction in the linear mixed models, which were additionally adjusted for age, gender, baseline BMI, fasting glucose, fasting insulin, (also diet allocation in panel B), and subjects. Differences in weight change from baseline were compared after 24 weeks through pairwise comparisons using post hoc t-tests and presented as mean weight change from baseline with 95% confidence intervals. Panel A: No difference in weight change was observed between the two diets (low and high dairy) within any of the three P/B groups (all P≤0.23). For clarity, confidence intervals were omitted from panel A. Panel B: The two different diets were collapsed and differences in weight change between the three P/B groups were compared after 24 weeks. § indicate significant difference between the low P/B group and each of the high P/B and 0-*Prevotella* group (both P<0.001).
Figure 2:
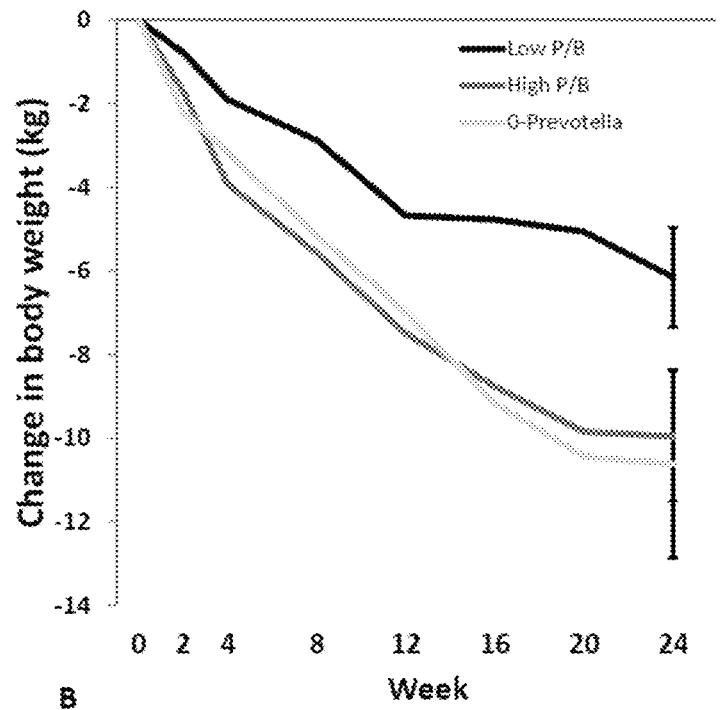

After the 24-week caloric restricted diet, no difference in 24 week body weight change was observed between the two allocated diets within the 0-*Prevotella* group [0.50 kg (95% CI, −5.84, 6.83; P=0.88)], low P/B group [0.03 kg (95% CI, −2.28, 2.34; P=0.98)], or high P/B group [1.79 kg (95% CI, −1.12, 4.70; P=0.23)] (FIG. 2, Panel A).

Irrespective of the allocated diets, participants with a low P/B ratio lost 3.80 kg (95% CI, 1.77, 5.84; P<0.001) and 4.47 kg (95% CI, 1.90, 7.04; P<0.001) less body weight compared to participants with high P/B ratio and 0-*Prevotella*, respectively. No difference was observed between participants with high P/B ratio and 0-*Prevotella* [0.66 kg (95% CI, −2.16, 3.49; P=0.65)] (FIG. 2, Panel B; Table 7). Likewise, participants with a low P/B ratio lost 3.80 kg (95% CI, 1.13, 6.48; P=0.005) and 3.41 kg (95% CI, 0.11, 6.71; P=0.043) less body fat compared to participants with high P/B ratio and 0-*Prevotella*, respectively. There was no difference in fat loss between participants with high P/B ratio and 0-*Prevotella* [0.40 kg (95% CI, −3.35, 4.14; P=0.84)] (Table 7).

TABLE 7

Changes in body weight and body fat after 24 weeks when stratified into three groups according to *Prevotella*-to-*Bacteroides* ratio (n = 51)

|  | 0-Prevotella (n = 8) | Low P/B (n = 26) | High P/B (n = 17) |
|---|---|---|---|
| ΔBody weight (kg) | −10.62 (−12.86; −8.38)$^a$ | −6.15 (−7.34; −4.96)$^b$ | −9.96 (−11.50; −8.41)$^a$ |
| ΔBody fat (kg) | −8.58 (−12.29; −4.87)$^a$ | −5.18 (−6.71; −3.66)$^b$ | −8.98 (−11.03; −6.95)$^{1a}$ |

Abbreviations:
P/B, *Prevotella*-to-*Bacteroides*.
Data are presented as estimated mean body weight and body fat change from baseline and 95% confidence intervals for three *Prevotella*-to-*Bacteroides* groups after 24 weeks in the linear mixed models, which were additionally adjusted for age, gender, baseline BMI, fasting glucose, fasting insulin, diet allocation and random effects for subjects (only when analyzing body weight).
Different alphabets within a row (a, b) indicate significant differences (P < 0.05).
$^1$n = 16 (missing data for one individual)

Macronutrient and fiber intake from the self-reported dietary intake during the 24 week was correlated as seen in Table S1.

TABLE S1

Correlation and partial correlation coefficients between mean carbohydrate, fat, protein and fiber intake during the 24 weeks (n = 51).

|  | Carbohydrate (%) | Fat (%) | Protein (%) |
|---|---|---|---|
| Fat (%) | −0.68**/−0.85** |  |  |
| Protein (%) | −0.11/−0.64** | −0.46**/−0.71** |  |
| Fiber (g/10 MJ) | −0.05/−0.33* | −0.31*/−0.37* | 0.32*/−0.06 |

TABLE S1-continued

Correlation and partial correlation coefficients between mean carbohydrate, fat, protein and fiber intake during the 24 weeks (n = 51).

| Carbohydrate (%) | Fat (%) | Protein (%) |
|---|---|---|

First number is Pearson's correlation coefficients between two dietary components. Second number is the partial correlation coefficients between two dietary components (adjusting for the remaining two dietary components).
*P < 0.05,
**P < 0.001.

In the fully adjusted model, participants with low P/B ratio lost more body weight when consuming a diet above the median in carbohydrate (%) and dietary fiber (g/10 MJ) (both P<0.008) whereas the high P/B ratio lost more body weight when consuming a diet above the median in carbohydrate (%), dietary fiber (g/10 MJ), and protein (%) (all P<0.001) (Table 8) [Mean difference: Fat: 4.0 kg (0.6;7.3, P=0.02); Carbohydrate: 4.3 kg (1.3;7.2, P=0.004); Protein: 6.6 kg (3.0;10.3, P<0.001); Dietary fiber: 5.1 (1.7;8.6, P=0.003)]. Furthermore, participants in the 0-*Prevotella* group lost more body weight when consuming a diet above the median in carbohydrate (%) and fat (%) (both P<0.001).

TABLE 8

Change in body weight among the three *Prevotella*-to-*Bacteriodes* (P/B) groups stratified by median of self-reported dietary intake (n = 51)

|  |  | 0-*Prevotella* (n = 8) | | Low P/B (n = 26) | | High P/B (n = 17) | |
|---|---|---|---|---|---|---|---|
|  |  | Lower median | Higher median | Lower median | Higher median | Lower median | Higher median |
|  |  | (n = 3) | (n = 5) | (n = 11) | (n = 15) | (n = 7) | (n = 10) |
| Fat (E %)$^1$ | M1 | −6.3 | −13.0 | −6.4 | −5.6 | −12.2 | −7.5 |
|  |  | (−9.8; −2.8) | (−15.7; −10.3)$^2$ | (−8.2; −4.6) | (−7.2; −4.1) | (−14.4; −9.9) | (−9.4; −5.6)$^2$ |
|  | M2 | −6.0 | −13.0 | −6.0 | −5.9 | −12.8 | −8.1 |
|  |  | (−9.5; −2.4) | (−15.5; −10.5)$^2$ | (−7.7; −4.3) | (−7.5; −4.4) | (−15.1; −10.6) | (−10.0; −6.3)$^2$ |
|  | M3 | −3.0 | −13.8 | −4.9 | −6.9 | −11.6 | −9.6 |
|  |  | (−6.2; 0.3) | (−16.1; −11.6)$^2$ | (−6.5; −3.4) | (−8.3; −5.5) | (−13.7; −9.4) | (−11.3; −7.8) |
|  |  | (n = 4) | (n = 4) | (n = 11) | (n = 15) | (n = 12) | (n = 5) |
| Protein (E %)$^1$ | M1 | −11.1 | −9.9 | −6.5 | −5.6 | −7.6 | −13.6 |
|  |  | (−14.1; −8.2) | (−12.8; −6.9) | (−8.3; −4.7) | (−7.1; −4.1) | (−9.3; −5.9) | (−16.3; −11.0)$^2$ |
|  | M2 | −10.8 | −8.9 | −6.1 | −5.9 | −8.4 | −14.8 |

TABLE 8-continued

Change in body weight among the three *Prevotella*-to-*Bacteriodes* (P/B) groups stratified by median of self-reported dietary intake (n = 51)

|  |  | 0-*Prevotella* (n = 8) | | Low P/B (n = 26) | | High P/B (n = 17) | |
|---|---|---|---|---|---|---|---|
|  |  | Lower median | Higher median | Lower median | Higher median | Lower median | Higher median |
|  | M3 | (−13.7; −8.0) −10.4 (−13.1; −7.6) | (−11.8; −6.0) −9.3 (−12.1; −6.4) | (−7.7; −4.5) −6.1 (−7.8; −4.5) | (−7.4; −4.3) −5.7 (−7.2; −4.2) | (−10.1; −6.8) −8.6 (−10.3; −7.0) | (−17.6; −12.0)[2] −14.8 (−17.5; −12.1)[2] |
| Carbohydrate (E %)[1] | M1 | (n = 6) −9.2 (−11.5; −6.9) | (n = 2) −14.4 (−18.3; −10.4)[2] | (n = 12) −5.2 (−6.8; −3.6) | (n = 14) −6.6 (−8.1; −5.1) | (n = 8) −5.7 (−7.7; −3.7) | (n = 9) −12.7 (−14.5; −10.8)[2] |
|  | M2 | −9.1 (−11.3; −6.9) | −15.0 (−18.7; −11.3)[2] | −5.4 (−7.0; −3.8) | −6.4 (−7.9; −5.0) | −6.4 (−8.4; −4.4) | −13.1 (−14.9; −11.3)[2] |
|  | M3 | −8.3 (−10.3; −6.3) (n = 2) | −14.8 (−18.1; −11.4)[2] (n = 6) | −4.2 (−5.7; −2.8) (n = 12) | −7.7 (−9.1; −6.3)[2] (n = 14) | −6.0 (−8.0; −4.1) (n = 8) | −13.8 (−15.4; −12.1)[2] (n = 9) |
| Dietary fiber (g/10 MJ)[1] | M1 | −10.8 (−14.5; −7.0) | −10.4 (−12.6; −8.2) | −4.4 (−5.9; −2.8) | −7.3 (−8.8; −5.9)[2] | −4.7 (−6.6; −2.9) | −13.5 (−15.3; −11.8)[2] |
|  | M2 | −9.8 (−13.3; −6.2) | −11.1 (−13.2; −8.9) | −4.1 (−5.7; −2.5) | −7.2 (−8.5; −5.9)[2] | −5.7 (−7.5; −3.8) | −13.9 (−15.6; −12.3)[2] |
|  | M3 | −10.0 (−13.7; −6.3) | −11.0 (−13.2; −8.8) | −4.1 (−5.8; −2.4) | −7.3 (−8.7; −5.9)[2] | −5.6 (−7.6; −3.6) | −13.9 (−15.6; −12.2)[2] |

Abbreviations: P/B, *Prevotella*-to-*Bacteroides*. Data are presented as estimated mean weight change from baseline and 95% confidence intervals for each combination of the dietary intake-time-P/B strata interaction after 24 weeks in the linear mixed models, which were adjusted for subject as random effects (M1). In model 2 (M2) additional adjustments for age, gender, baseline BMI, fasting glucose, fasting insulin, and diet allocation as fixed factors were performed. Model 3 (M3) include M2 + additional adjustments of fat E %, protein E %, carbohydrate E %, and fiber g/10 MJ as continues variables (except when included as exposure). The displayed n is from M1 at week 24.
[1]The approximate median value among the 49 participants having self-reported dietary intake was used as cut-off and was as following: Fat (31 E %), Protein (20 E %), Carbohydrate (46 E %), Fiber (30 g/10 MJ).
[2]Significant different (P < 0.05) within P/B-group between lower and higher median of dietary component.

Among individuals with high P/B ratio, fat (%) (r=0.59), protein (%) (r=−0.58), and fiber (g/10 MJ) (r=−0.84) were significantly correlated with 24-week weight change (P<0.015) (FIG. 3 & FIGS. 19A-D), but only fiber intake remained significant after adjusting for multiple covariates (r=0.90, P<0.001) (Table S2). No significant correlations was found between dietary components and weight loss among subjects with low P/B or 0-*Prevotella*.

TABLE S2

Correlation and partial correlation coefficients between 24-week weight change and each of mean carbohydrate, fat, protein and fiber intake during the 24 weeks (n = 51).

|  | Carbohydrate (%) | Fat (%) | Protein (%) | Fiber (g/10 MJ) |
|---|---|---|---|---|
| All | −0.08/−0.06/−0.11 | 0.22/0.16/−0.07 | −0.19/−0.16/−0.12 | −0.37*/−0.37*/−0.32* |
| 0-*Prevotella* (n = 8) | −0.12/−0.26/−0.50 | −0.21/−0.27/0.08 | 0.20/0.20/0.27 | 0.04/0.04/0.21 |
| Low P/B group (n = 26) | 0.01/0.19/−0.02 | 0.11/−0.04/−0.09 | −0.10/−0.09/0.02 | −0.33/−0.29/−0.25 |
| High P/B group (n = 17) | −0.27/−0.34/0.60 | 0.59*/0.52/0.57 | −0.58*/−0.54*/0.39 | −0.84**/−0.90**/−0.90** |

First number is Pearson's correlation coefficients between 24-week weight change and one dietary component. Second number is the partial correlation coefficients between 24-week weight change and one dietary component adjusted for age, gender, baseline BMI. Third number is additionally adjusting for the remaining three dietary components.
*P < 0.05,
**P < 0.001.

Figure 20:
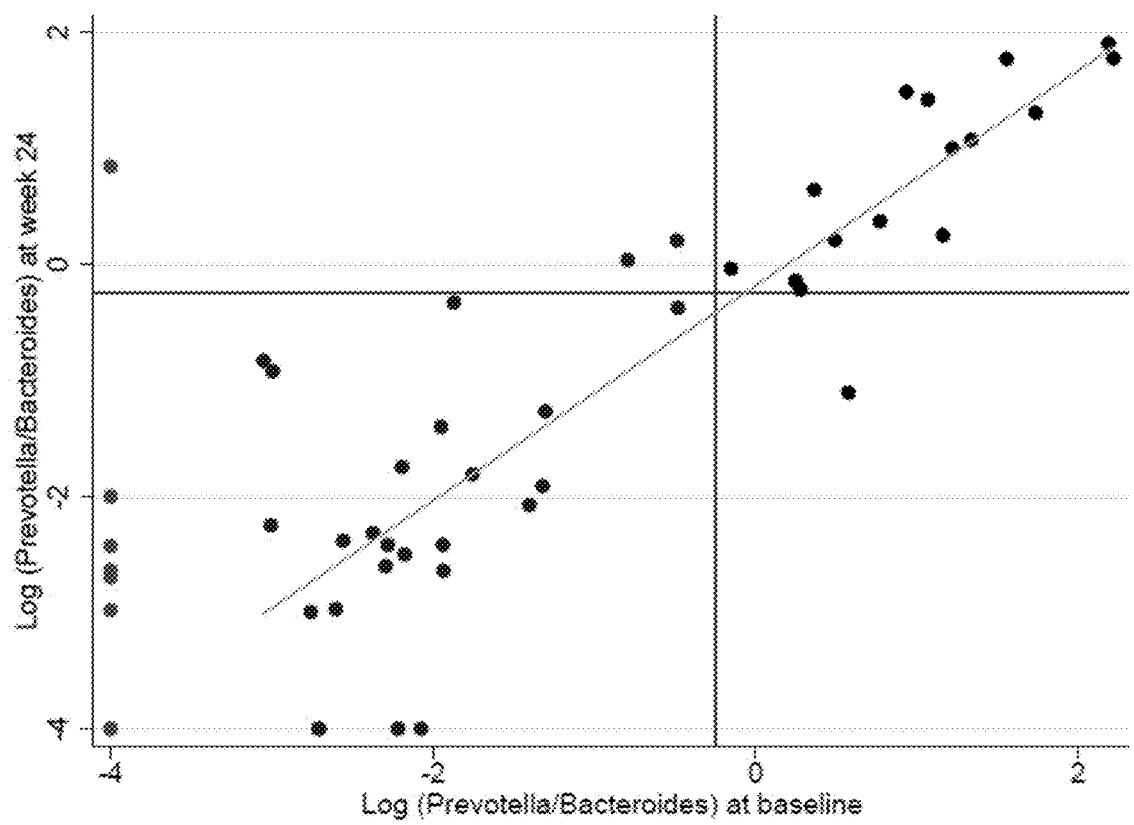
FIG. 20 is a scatterplot between baseline and 24-week post-intervention log(*Prevotella*/Bacteriodes). Lines (x=−0.25; y=−0.25) separate low and high *Prevotella*/Bacteriodes-ratio. Subjects with no detectable *Prevotella* have the value "−4" on the figure. Pearson's correlation coefficient (not including subjects with 0-*Prevotella*) is 0.87 (P<0.001; n=42). Two microbiota samples are missing at 26 weeks (total n=50).

The correlation coefficient between baseline and post-interventional log(P/B-ratio) was 0.87 (P<0.001) as illustrated in FIG. 20 emphasizing that the P/B-ratio overall remained stable during 24 weeks despite the observed weight loss.

Discussion

As hypothesized, participants with no detectable *Prevotella* spp. and high P/B ratio lost approximately 4 kg more during 24 weeks compared to participants with low P/B ratio. Furthermore, this increased weight loss response among participants with no detectable *Prevotella* spp. and high P/B ratio was associated with individual macronutrient composition and dietary fiber intake estimated from 7-day dietary records. Specifically, among participants with high P/B ratio fiber intake above the median resulted in weight loss being more than twice as large, thereby explaining the entire weight loss difference between the low and high P/B groups. Finally, no differences in weight loss between the two allocated diets, differing in calcium, were observed for any of our three P/B groups. The present study serves as a validation of our recent observation showing an interaction between P/B ratio and dietary intake on weight and fat loss response in a dietary intervention studies (24).

Recently, the distinction of enterotypes as discrete clusters was challenged by studies suggesting that enterotype distribution is continuous and that information may be masked within these enterotype clusters (29, 30). The three P/B groups in the present study were not as discrete as in our previous study (24); however, the population could be divided with only few individuals possibly being intermediate. Furthermore, a comparison of the pre- and post interventional P/B-ratio shows good correlation and classification agreement, emphasizing that these ratios are very stable as previously reported (23). From these results we cannot conclude if the P/B ratio is causally related to the different effects of the diets or simply a marker of something else that we did not measure. However, the study highlights the relative abundance of *Prevotella* spp. as important in the classification of microbiota profiles. In agreement herewith, we recently observed that subjects with no detectable *Prevotella* spp. responded differently than subjects in the low P/B group following a dietary intervention (24). Although these findings were confirmed here, as the 0-*Prevotella* group lost more body weight compared to the low P/B group and supposedly lost more weight when consuming diets higher in carbohydrates and/or fat, this 0-*Prevotella* group only consisted of 8 participants. Therefore, these observations need further investigations to make solid conclusions.

Administration of short chain fatty acids (SCFA) have been reported to result wide range of health benefits including improvements in blood lipid profiles, glucose homeostasis, body composition, and reduced body weight (31). However, studies tend to investigate all SCFA as a whole and neglect to report the specific effects associated with the individual SCFA with the most abundant being acetate, propionate, and butyrate (31). Members of the phylum *Bacteroidetes* are known to be efficient degraders of dietary fiber and include the genera *Bacteroides* and *Prevotella* (32). In vitro the *Prevotella*-driven and Bacteriodes-driven microbiota have been shown to produce different amounts and profiles of SCFA from the same carbohydrate substrates (13). Therefore, the differences in P/B ratio in the present study, observed to affect the weight loss responsiveness to a fiber rich diet, could potentially be explained by the efficacy of energy harvest primarily as SCFA (12) or that the production of SCFA affects appetite either directly in the brain or through different signaling pathway influencing the secretion of gastrointestinal hormones (15, 31). Improvements in post-prandial blood glucose and insulin after dietary fiber intake were recently found to be positively associated with the abundance of *Prevotella* (33). Therefore, the importance of pre-treatment fasting glucose and insulin to determine the optimal diet for weight management (34-36), might also be linked to gut microbiota profiles, and we adjusted for fasting glucose and fasting insulin. However, independent of the mechanisms, the three P/B ratio groups may serve as a biomarker to predict future weight loss success on specific diets.

Limitations of the study include that the study was not designed to examine for differences in responsiveness according to P/B ratio, and it is a matter of chance that we had enough participants in each group to provide statistical power for analyses. However, the post-hoc approach can also be looked upon as a strength as the study was double-blinded with respect to the P/B ratio of the participants, and the identified difference in dietary responsiveness cannot have been influenced by knowledge of the participants or investigators. Furthermore, when stratifying on P/B ratio, the randomized study design that should balance out known and unknown confounders are weakened, which is why we adjusted for a number of baseline characteristics, including age, gender, and BMI. Although some of the analyses, especially those for individuals with 0-*Prevotella*, are based on relatively small numbers and the validity therefore could be questioned, these findings are consistent with our previous findings (24), suggesting robustness of our findings. On the other hand, the individuals in the present study with no detectable *Prevotella* bacteria at baseline primarily belonged to the low P/B group after the 24-week intervention (see FIG. 20). Furthermore, the present results are partly based on self-reported dietary data during a controlled dietary intervention study with regular dietetic counseling of the participants. As the individual differences in macronutrient and dietary fiber consumption during the trial were found to influence weight loss responsiveness among the high P/B group, we speculate that free-living dietary intake, when not counseled by dieticians, would have an even bigger effect. In the current study, as well as our recently published study (24), we observed that individuals characterized with a high P/B-ratio tended to have a higher baseline BMI. However, as only the individuals with high P/B-ratio that consumed more fibers lost more weight, regression towards the mean is not likely to play a major role. Furthermore, baseline BMI was recently found to be identical whether dominated by *Prevotella* or *Bacteriodes* among >100 diabetic patients (37). At present time, the main limitation when using the P/B ratio as a pre-treatment determinant of dietary weight loss among individual is the slightly deviating cut-offs compared to previously reported (24). These differences in cut-off between studies could reflect population specific P/B ratios; however, more likely they reflect differences in the methodology of the bacterial profiling of *Prevotella* spp. and *Bacteroides* spp., where the present study applied 16S rRNA gene sequencing whereas the previous study applied quantitative polymerase chain reaction (qPCR) (23, 24). Therefore, future use of the P/B ratio to determine individual dietary weight loss response on different diets would need a specific reference methodology or at least take the specific methodology used into consideration. It should furthermore be noted that the fecal microbiota primarily reflects the microbiota of the distal part of the colon. Therefore, it remains unknown how the fecal P/B ratio relates to the bacterial composition in the proximal part of the colon as well as the small intestine.

Finally, industrialized populations consuming a Western diet have microbiotas that are dominated by the family Bacteroidaceae (composed of four genera including *Bacteroides*) whereas traditional populations across Africa, Asia, and South America have microbiotas that are dominated by the family *Prevotella* ceae (composed of four genera including *Prevotella*) that has been found to fluctuate according to foods available during different seasons (38). Although we know that it is difficult to change the P/B ratio though dietary interventions (20, 21, 23, 24), we know that short term diets without carbohydrates (25) and seasonal difference (38) affect these genera and thereby provide evidence that we might be able to manipulate the P/B ratio.

In summary, we successfully validated the pre-treatment P/B ratio to be an important biomarker associated with dietary weight loss. Specifically, we found that participants having high P/B ratio had a larger 24 week weight loss compared to participants with low P/B ratio when advised to eat a healthy energy restricted diet (carbohydrate: 52E %, fat: 30 E % and protein: 18E %). This kg differences in weight loss between high and low P/B ratio groups was explained by interaction with the actual diet consumed. Thus, individuals with a high P/B ratio were more susceptible to body weight loss, compared to individuals with a low P/B ratio, specifically on a diet rich in fiber and possibly also high in carbohydrates, high in protein and low in fat.

REFERENCES

1. Sacks F M, Bray G A, Carey V J, Smith S R, Ryan D H, Anton S D, et al. Comparison of weight-loss diets with different compositions of fat, protein, and carbohydrates. N Engl J Med 2009; 360:859-73.
2. Foster G D, Wyatt H R, Hill J O, Makris A P, Rosenbaum D L, Brill C, et al. Weight and metabolic outcomes after 2. years on a low-carbohydrate versus low-fat diet: a randomized trial. Ann Intern Med. 2010; 153:147-57.
3. Poulsen S K, Due A, Jordy A B, Kiens B, Stark K D, Stender S, et al. Health effect of the New Nordic Diet in adults with increased waist circumference: a 6-mo randomized controlled trial. Am J Clin Nutr. 2014; 99:35-45.
4. Larsen T M, Dalskov S, van Baak M, Jebb S A, Papadaki A, Pfeiffer A F, et al. Diets with high or low protein content and glycemic index for weight-loss maintenance. N Engl J Med 2010; 363:2102-13.
5. Petersen M, Taylor M, Saris W, Verdich C, Toubro S, Macdonald I, et al. Randomized, multi-center trial of two hypo-energetic diets in obese subjects: high-versus low-fat content. Int J Obes 2006; 30:552-60.
6. Turnbaugh P J, Hamady M, Yatsunenko T, Cantarel B L, Duncan A, Ley R E, et al. A core gut microbiome in obese and lean twins. Nature 2009; 457;480-4.
7. Le Chatelier E, Nielsen T, Qin J, Prifti E, Hildebrand F, Falony G, et al. Richness of human gut microbiome correlates with metabolic markers. Nature 2013; 500:541-6.
8. Cotillard A, Kennedy S P, Kong L C, Prifti E, Pons N, Le Chatelier E, et al. Dietary intervention impact on gut microbial gene richness. Nature 2013; 500:585.
9. Ridaura V K, Faith J J, Rey F E, Cheng J, Duncan A E, Kau A L, et al. Gut microbiota from twins discordant for obesity modulate metabolism in mice. Science 2013; 341:1241214.
10. Liu R, Hong J, Xu X, Feng Q, Zhang D, Gu Y, et al. Gut microbiome and serum metabolome alterations in obesity and after weight-loss intervention. Nat Med 2017; 23:859-68.
11. Vrieze A, Van Nood E, Holleman F, Salojärvi J, Kootte R S, Bartelsman J F, et al. Transfer of intestinal microbiota from lean donors increases insulin sensitivity in individuals with metabolic syndrome. Gastroenterology 2012; 143:913-916.
12. Turnbaugh P J, Ley R E, Mahowald M A, Magrini V, Mardis E R, Gordon J I. An obesity-associated gut microbiome with increased capacity for energy harvest. Nature 2006; 444:1027-131.
13. Chen T, Long W, Zhang C, Liu S, Zhao L, Hamaker B R. Fiber-utilizing capacity varies in *Prevotella*- versus *Bacteroides*-dominated gut microbiota. Sci Rep 2017; 7:2594.
14. Kang C, Zhang Y, Zhu X, Liu K, Wang X, Chen M, et al. Healthy subjects differentially respond to dietary capsaicin correlating with specific gut enterotypes. The Journal of Clinical Endocrinology & Metabolism 2016; 101: 4681-9.
15. Tolhurst G, Heffron H, Lam Y S, Parker H E, Habib A M, Diakogiannaki E, et al. Short-chain fatty acids stimulate glucagon-like peptide-1 secretion via the G-protein-coupled receptor FFAR2. Diabetes. 2012; 61:364-71.
16. Mayer E A, Tillisch K, Gupta A. Gut/brain axis and the microbiota. J Clin Invest 2015;125:926-38.
17. Zeevi D, Korem T, Zmora N, Israeli D, Rothschild D, Weinberger A, et al. Personalized nutrition by prediction of glycemic responses. Cell 2015; 163:1079-94.
18. Korem T, Zeevi D, Zmora N, Weissbrod O, Bar N, Lotan-Pompan M, et al. Bread Affects Clinical Parameters and Induces Gut Microbiome-Associated Personal Glycemic Responses. Cell Metabolism 2017; 25:1243-1253.
19. Arumugam M, Raes J, Pelletier E, Le Paslier D, Yamada T, Mende D R, et al. Enterotypes of the human gut microbiome. Nature 2011; 473:174-80.
20. Wu G D, Chen J, Hoffmann C, Bittinger K, Chen Y Y, Keilbaugh S A, et al. Linking long-term dietary patterns with gut microbial enterotypes. Science 2011; 334:105-8.
21. Lim M Y, Rho M, Song Y, Lee K, Sung J, Ko G. Stability of gut enterotypes in Korean monozygotic twins and their association with biomarkers and diet. Scientific reports 2014; 4:7348.
22. de Moraes A C, Fernandes G R, da Silva I T, Almeida-Pititto B, Gomes E P, da Costa Pereira A, et al. Enterotype may drive the dietary-associated cardiometabolic risk factors. Frontiers in Cellular and Infection Microbiology 2017; 7.
23. Roager H M, Licht T R, Poulsen S K, Larsen T M, Bahl M I. Microbial enterotypes, inferred by the prevotella-to-bacteroides ratio, remained stable during a 6-month randomized controlled diet intervention with the new nordic diet. Appl Environ Microbiol 2014; 80:1142-9.
24. Hjorth M F, Roager H M, Larsen T M, Poulsen S K, Licht T R, Bahl M I, et al. Pre-treatment microbial *Prevotella*-to-*Bacteroides* ratio, determines body fat loss success during a 6-month randomized controlled diet intervention. Int J Obes 2017 (doi:10.1038/ijo.2017.220).
25. Andrés M, Ana D, Juan José A, Amparo L. Effect of dietary carbohydrate restriction on an obesity-related *Prevotella*-dominated human faecal microbiota. Metagenomics 2013; 2.
26. Bendtsen L Q, T, Holm J B, Lorenzen J K, Mark A B, Kiilerich P, et al. High intake of dairy during energy restriction does not affect energy balance or the intestinal microflora compared to low dairy intake in overweight individuals in a Randomized Controlled Trial. Appl Physiol Nutr Metab 2018; 43:1-10.
27. Nordic Nutrition Recommendations 2004: Integrating nutrition and physical activity. Available from: http://urn.kb.se/resolve?urn=urn:nbn:se:norden:org:diva-1487.
28. Baecke J A, Burema J, Frijters J E. A short questionnaire for the measurement of habitual physical activity in epidemiological studies. Am J Clin Nutr 1982; 36:936-42.
29. Knights D, Ward T L, McKinlay C E, Miller H, Gonzalez A, McDonald D, et al. Rethinking "enterotypes". Cell host & microbe 2014; 16:433-7.
30. Gorvitovskaia A, Holmes S P, Huse S M. Interpreting *Prevotella* and *Bacteroides* as biomarkers of diet and lifestyle. Microbiome 2016; 4:15.
31. Byrne C S, Chambers E S, Morrison D J, Frost G. The role of short chain fatty acids in appetite regulation and energy homeostasis. Int J Obes 2015; 39:1331-8.
32. Schroeder B O, Bäckhed F. Signals from the gut microbiota to distant organs in physiology and disease. Nat Med 2016; 22:1079-89.
33. Kovatcheva-Datchary P, Nilsson A, Akrami R, Lee Y S, De Vadder F, Arora T, et al. Dietary fiber-induced improvement in glucose metabolism is associated with increased abundance of *Prevotella*. Cell metabolism 2015; 22:971-82.
34. Hjorth M F, Due A, Larsen T M, Astrup A. Pre-treatment fasting plasma glucose modifies dietary weight loss maintenance success: results from a stratified RCT. Obesity 2017; 25:2045-2048.
35. Astrup A, Hjorth M F. Low-Fat or Low Carb for Weight Loss? It Depends on Your Glucose Metabolism. EBioMedicine 2017; 22:20-21.
36. Hjorth M F, Ritz C, Blaak E E, Saris W H, Langin D, Poulsen S K, et al. Pretreatment fasting plasma glucose and insulin modify dietary weight loss success: results from 3 randomized clinical trials. Am J Clin Nutr 2017; 106:499-505.

37. Gu Y, Wang X, Li J, Zhang Y, Zhong H, Liu R, et al. Analyses of gut microbiota and plasma bile acids enable stratification of patients for antidiabetic treatment. Nature communications 2017; 8:1785.

38. Smits S A, Leach J, Sonnenburg E D, Gonzalez C G, Lichtman J S, Reid G, et al. Seasonal cycling in the gut microbiome of the Hadza hunter-gatherers of Tanzania. Science 2017; 357:802-6.

Example 6: Pretreatment Microbial *Prevotella* to *Bacteriodes* Ratio (P/B Ratio) in Combination with Fasting Insulin (FI) Predict Weight Maintenance Depending Upon Diet Overview of Study.

The study on which these analyses are based is referred to herein as PROKA. The protocol for this study is found at ClinicalTrials.gov Identifier: NCT01561131 and the study has been described in details in Kjølbæk et al. (2017) Am J Clin Nutr 106:684-697. Briefly, the study starts with a low calorie diet (LCD) similar to the DioGenes study of Example 4 herein. The patients are then randomized to 4 different diets for 24 weeks. The diets consist of ≈90% habitual diet (average Danish diet [ADD]; fat≈35E %, carb≈45E %, protein≈20E %) with randomization to four different supplements (three with different proteins and one with Maltodextrin). The following analyses are for body weight during the 24-week weight maintenance (WM) period. We show weight development in two separate analyses: 1) All individuals regardless of diets, 2) Only individuals on Maltodextrin.

Establishing the P/B Ratio.

Microbiota from before the initial 8-week LCD phase was used. There was no bi-polar distribution in P/B-ratio as was observed in previous studies described in Hjorth M, Roager H, Larsen T, Poulsen S, Licht T, Bahl M, et al. Pre-treatment microbial *Prevotella*-to-*Bacteroides* ratio, determines body fat loss success during a 6-month randomized controlled diet intervention. Int J Obes (Lond). 2017 September 8. doi: 10.1038/ijo.2017.220 (the SHOPUS study) and the study described in Example 5 (the MEPEB study). Therefore, the median value was used to establish P/B ratio for this analysis. Individuals with no detected *Prevotella* spp. were categorized as having low P/B-ratio which gave the best prediction. There was no difference in baseline characteristics (age, BMI, FI, FPG, FM, gender) between P/B-ratio groups.

Establishing Fasting Plasma Glucose (FPG) and Fasting Insulin (FI).

Fasting plasma glucose groups represent normoglycemics (<100 mg/dL) and prediabetics (100-125 mg/dL). No diabetics were included in the study. The median was used as the cutoff for fasting insulin (low FI: below median; high FI: above median).

Analysis of Weight Gain on Each of Four Diets Alone and in Combination during Weight Maintenance (WM) Period of 24 Weeks.

Weight gain on individual and combined diets and maltodextrin diets stratified on low or high P/B ratio were analyzed and the results are shown in Table 9.

TABLE 9

Weight regain on each of the four diets (and combined) stratified on low or high P/B-ratio

| Randomization | P/B-ratio | 24 w weight change (kg) | Lower 95% CI | Upper 95% CI | n | P-value |
|---|---|---|---|---|---|---|
| All | low | 1.13 | 0.38 | 1.88 | 67 | 0.003 |
| All | High | 2.70 | 1.94 | 3.45 | 68 | <0.001 |
| All | Difference | -1.56 | -2.64 | -0.49 | | 0.004 |
| Maltodextrin | low | 0.44 | -1.21 | 2.10 | 13 | 0.60 |
| Maltodextrin | High | 2.95 | 1.50 | 4.40 | 18 | <0.001 |
| Maltodextrin | Difference | -2.51 | -4.71 | -0.31 | | 0.026 |

Adjusted for person analyzing the sample (1 or 2), baseline age, baseline BMI, LCD weight loss, and gender (and randomization when analyzing all) as fixed effects and id as random effect.

As shown in Table 9, overall, those individuals having a higher P/B ratio were associated with a 1.56 kg (P=0.004) larger weight gain when consuming the Average Danish Diet (ADD) with minor supplements. This was slightly higher (2.51 kg, P=0.026) in the Maltodextrin group. Weight gain on individual and combined diets and maltodextrin diets stratified on low or high fasting insulin were analyzed and the results are shown in Table 10.

TABLE 10

Weight regain on each of the four diets (and combined) stratified on low or high fasting insulin

| Randomization | FI | 24 w weight change (kg) | Lower 95% CI | Upper 95% CI | n | P-value |
|---|---|---|---|---|---|---|
| All | low | 1.59 | 0.92 | 2.25 | 98 | <0.001 |
| All | High | 2.54 | 1.85 | 3.23 | 94 | <0.001 |
| All | Difference | -0.95 | -1.94 | 0.03 | | 0.058 |
| Maltodextrin | low | 1.34 | 0.02 | 2.65 | 24 | 0.046 |
| Maltodextrin | High | 3.40 | 2.07 | 4.73 | 24 | <0.001 |
| Maltodextrin | Difference | -2.07 | -3.93 | -0.20 | | 0.030 |

Adjusted for person analyzing the sample (1 or 2), baseline age, baseline BMI, LCD weight loss, and gender (and randomization when analyzing all) as fixed effects and id as random effect.

As shown in Table 10, overall, subjects with higher fasting insulin gained 0.95 kg more (P=0.058) than subjects with low FI. This was particularly true for the Maltodextrin group (2.07 kg, P=0.030).

Weight gain on individual and combined diets and maltodextrin diets stratified on low or high fasting plasma glucose were analyzed and the results are shown in Table 11.

TABLE 11

Weight regain on each of the four diets (and combined) stratified on low or high fasting plasma glucose

| Randomization | FPG | 24 w weight change (kg) | Lower 95% CI | Upper 95% CI | n | P-value |
|---|---|---|---|---|---|---|
| All | low | 2.06 | 1.39 | 2.73 | 102 | <0.001 |
| All | High | 2.09 | 1.38 | 2.81 | 87 | <0.001 |
| All | Difference | -0.03 | -1.04 | 0.98 | | 0.96 |
| Maltodextrin | low | 2.23 | 1.05 | 3.42 | 31 | <0.001 |
| Maltodextrin | High | 2.45 | 0.87 | 4.02 | 17 | 0.002 |

TABLE 11-continued

Weight regain on each of the four diets (and combined) stratified on low or high fasting plasma glucose

| Randomization | FPG | 24 w weight change (kg) | Lower 95% CI | Upper 95% CI | n | P-value |
|---|---|---|---|---|---|---|
| Maltodextrin | Difference | −0.21 | −2.19 | 1.77 | | 0.83 |

Adjusted for person analyzing the sample (1 or 2), baseline age, baseline BMI, LCD weight loss, and gender (and randomization when analyzing all) as fixed effects and id as random effect.

As shown in Table 11, no overall or supplement specific differences in weight maintenance success were found based on FPG.

Weight gain during the 24-week WM period stratified by the combination of PB ratio and FI was analyzed and the results are shown in Table 12.

TABLE 12

Weight regain stratified on FI-groups and P/B-ratio

| Randomization | P/B-ratio | Fasting insulin | 24 w weight change (kg) | Lower 95% CI | Upper 95% CI | n | P-value |
|---|---|---|---|---|---|---|---|
| All | low | low | 1.28$^a$ | 0.28 | 2.29 | 38 | 0.012 |
| All | low | High | 0.81$^a$ | −0.34 | 1.97 | 29 | 0.17 |
| All | high | low | 1.36$^a$ | 0.20 | 2.51 | 29 | 0.021 |
| All | high | High | 3.94$^b$ | 2.89 | 4.99 | 36 | <0.001 |
| Maltodextrin (control) | low | low | −0.41$^a$ | −2.62 | 1.79 | 7 | 0.71 |
| Maltodextrin (control) | low | High | 1.33$^a$ | −1.06 | 3.72 | 6 | 0.28 |
| Maltodextrin (control) | high | low | 0.42$^a$ | −1.70 | 2.54 | 8 | 0.70 |
| Maltodextrin (control) | high | High | 5.11$^b$ | 3.14 | 7.08 | 9 | <0.001 |

Adjusted for person analyzing the sample (1 or 2), baseline age, baseline BMI, baseline fasting glucose, LCD weight loss, and gender (and randomization when analyzing all) as fixed effects and id as random effect.

As shown in Table 12, the observed 1.56 kg difference in Table 9 is driven by the participants with high P/B-ratio and high fasting insulin regained 2.66-3.13 kg more compared to those with low P/B-ratio while no difference was observed for those participants with high P/B-ratio and low fasting insulin (0.08-0.55 kg). This difference was even more pronounced in the Maltodextrin group (that resemble ADD the most).

Weight gain during the 24-week WM period stratified by the combination of P/B ratio and FPG glucose was analyzed and the results are shown in Table 13.

TABLE 13

Weight regain stratified on FPG-groups and P/B-ratio

| Randomization | P/B-ratio | Fasting glucose | 24 w weight change (kg) | Lower 95% CI | Upper 95% CI | n | P-value |
|---|---|---|---|---|---|---|---|
| All | low | low | 2.13$^a$ | 1.10 | 3.16 | 35 | <0.001 |
| All | low | High | 0.10$^b$ | −0.98 | 1.18 | 32 | 0.858 |
| All | high | low | 2.21$^a$ | 1.16 | 3.27 | 35 | <0.001 |
| All | high | High | 3.44$^a$ | 2.28 | 4.61 | 28 | <0.001 |
| Maltodextrin (control) | low | low | 1.90$^a$ | −0.02 | 3.82 | 9 | 0.053 |
| Maltodextrin (control) | low | High | −2.90$^b$ | −5.81 | 0.004 | 4 | 0.050 |
| Maltodextrin (control) | high | low | 1.70$^a$ | −0.12 | 3.51 | 11 | 0.067 |
| Maltodextrin (control) | high | High | 5.24$^c$ | 2.86 | 7.62 | 6 | <0.001 |

Adjusted for person analyzing the sample (1 or 2), baseline age, baseline BMI, baseline fasting insulin, LCD weight loss, and gender (and randomization when analyzing all) as fixed effects and id as random effect.

As shown in Table 13, the observed 1.56 kg difference in Table 9 is driven by the participants with high fasting glucose. Individuals having high FPG and low P/B ratio have the best weight development whereas individuals with high FPG and high P/B ratio have the worst weight development. This is even more pronounced in the Maltodextrin group alone (that resembles ADD the most).

Overall Conclusions

Overall, subjects with high compared to low P/B regained 1.56 kg more during the 24 weeks weight maintenance period. In support of this finding, we also found in previous studies, that participants with low compared to high P/B ratio lost an insignificant 1.02 kg (1.49 kg in the sensitivity analysis) more on the ADD diet. An average Danish diet (ADD) (with supplementation of protein and especially with supplementation of maltodextrin) therefore seems to best among participants with low P/B-ratio whereas the New Nordic Diet (NND) (and the fiber diet in MEPEB study of Example 5) is best among participants with high P/B-ratio. This supports the personalized nutrition.

Overall, participants with low compared to high FI tended to regain less. However, we found no difference according to FPG. Therefore, it appears that the P/B-ratio and FI/FPG are additive predictors for weight maintenance on various diets.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

We is claimed is:

1. A method of promoting weight loss in a patient wherein the patient has been identified as having at least one of: (a) a gut microbiota with a relative abundance of log 10 (*Prevotella* spp.) of greater than −3, (b) a gut microbiota with a relative abundance of log 10 (*Prevotella* spp./*Bacteroides* spp.) of greater than −2, (c) a gut microbiota with a relative abundance of Log 10 (*Prevotella* spp./Bacteroidetes all) of greater than −2, and (d) a gut microbiota with a relative abundance of Log 10(Bacteroidetes all/*Bacteroides* spp.) of greater than 0, comprising the steps of;
  (a) determining the patient's fasting plasma glucose (FPG) and fasting insulin level (FI); and
  (b) administering to the patient a predetermined diet, wherein
  (i) the patient's FPG is less than about 90 mg/dL, the patient's FI is below about 9.5 uU/mL and the predetermined diet is Diet 1;
  (ii) the patient's FPG is less than about 90 mg/dL, the patient's FI is above about 13 uU/mL, and the predetermined diet is Diet 2;
  (iii) the patient's FPG is between about 90 and 100 mg/dL, the patient's FI is above about 13 uU/mL and the predetermined diet is Diet 4;
  (iv) the patient's FPG is between about 100 and 115 mg/dL, the patient's FI is below about 9.5 uU/mL and the predetermined diet is Diet 5;
  (v) the patient's FPG is between about 100 and 115 mg/dL, the patient's FI is above about 13 uU/mL and the predetermined diet is Diet 6;
  (vi) vi the patient's FPG is between about 115 and 125 mg/dL, the patient's FI is below about 9.5 uU/mL and the predetermined diet is Diet 7;
  (vii) vii the patient's FPG is between about 115 and 125 mg/dL, the patient's FI is above about 13 uU/mL and the predetermined diet is Diet 8;
  (viii) the patient's FPG is greater than about 125 mg/dL, the patient's FI is below about 9.5 uU/mL and the predetermined diet is Diet 9;
  (ix) the patient's FPG is greater than about 125 mg/dL, the patient's FI is above about 13 uU/mL and the predetermined diet is Diet 10;
  (x) the patient's FPG is less than about 90 mg/dL, the patient's FI is between about 9.5 to about 13 uU/mL, and the predetermined diet is Diet 1 or Diet 2;
  (xi) the patient's FPG is between about 90 and 100 mg/dL, the patient's FI is between about 9.5 to about 13 uU/mL, and the predetermined diet is Diet 4;
  (xii) the patient's FPG is between about 100 and 115 mg/dL, the patient's FI is between about 9.5 to about 13 uU/mL, and the predetermined diet is Diet 5 or Diet 6;
  (xiii) the patient's FPG is between about 115 and 125 mg/dL, the patient's FI is between about 9.5 to about 13 uU/mL, and the predetermined diet is Diet 7 or Diet 8; or
  (xiv) the patient's FPG is greater than about 125 mg/dL, the patient's FI is between about 9.5 to about 13 uU/mL, and the predetermined diet is Diet 9 or Diet 10;
  wherein diets 1, 2 and 4-10 are defined in the table below:

| | |
|---|---|
| Diet 1 | Carbohydrate: 52-56% |
| | Protein: 19-23% |
| | Fat: 23-27% |
| | Fiber: >30 g/10 MJ |
| | Added sugar: <15E% |
| Diet 2 | Carbohydrate: 28-32% |
| | Protein: 23-27% |
| | Fat: 43-47% |
| | Fiber: >20 g/10 MJ |
| | Added sugar: <5E% |
| Diet 4 | Carbohydrate: 38-42% |
| | Protein: 23-27% |
| | Fat: 33-37% |
| | Fiber: >25 g/10 MJ |
| | Added sugar: <10E% |
| Diet 5 | Carbohydrate: 42-46% |
| | Protein: 19-23% |
| | Fat: 33-37% |
| | Fiber: >30 g/10 MJ |
| | Added sugar: <15E% |
| Diet 6 | Carbohydrate: 35-39% |
| | Protein: 23-27% |
| | Fat: 36-40% |
| | Fiber: >25 g/10 MJ |
| | Added sugar: <10E% |
| Diet 7 | Carbohydrate: 37-41% |
| | Protein: 19-23% |
| | Fat: 38-42% |
| | Fiber: >30 g/10 MJ |
| | Added sugar: <10E% |
| Diet 8 | Carbohydrate: 31-35% |
| | Protein: 23-27% |
| | Fat: 40-44% |
| | Fiber: >20 g/10 MJ |
| | Added sugar: <5E% |
| Diet 9 | Carbohydrate: 32-36% |
| | Protein: 19-23% |
| | Fat: 43-47% |
| | Fiber: >25 g/10 MJ |
| | Added sugar: <5E% |
| Diet 10 | Carbohydrate: 28-32% |
| | Protein: 23-27% |
| | Fat: 43-47% |
| | Fiber: >20 g/10 MJ |
| | Added sugar: <5E% |

2. The method of claim 1, wherein the weight loss is primarily fat loss.

3. The method of claim 1, further comprising the step of changing the predetermined diet based on changes in the patient's FPG and/or FI over time.

* * * * *